US010590159B2

(12) United States Patent
Liu et al.

(10) Patent No.: US 10,590,159 B2
(45) Date of Patent: Mar. 17, 2020

(54) LINCOMYCIN BIOSYNTHETIC INTERMEDIATES, METHOD FOR PREPARATION, AND USE THEREOF

(71) Applicants: SHANGHAI INSTITUTE OF ORGANIC CHEMISTRY, CHINESE ACADEMY OF SCIENCES, Shanghai (CN); HUZHOU CENTER OF BIO-SYNTHETIC INNOVATION, SHANGHAI INSTITUTE OF ORGANIC CHEMISTRY, CHINESE ACADEMY OF SCIENCES, Zhejiang (CN)

(72) Inventors: Wen Liu, Shanghai (CN); Min Wang, Shanghai (CN); Dongxiao Xu, Shanghai (CN); Qunfei Zhao, Zhejiang (CN); Qinglin Zhang, Zhejiang (CN)

(73) Assignees: Shanghai Institute of Organic Chemistry, Chinese Academy of Sciences, Shanghai (CN); Huzhou Center of Bio-Synthetic Innovation, Shanghai Institute of Organic Chemistry, Chinese Academy of Sciences, Huzhou, Zhejiang (CN)

( * ) Notice: Subject to any disclaimer, the term of this patent is extended or adjusted under 35 U.S.C. 154(b) by 183 days.

(21) Appl. No.: 15/575,630

(22) PCT Filed: Nov. 6, 2015

(86) PCT No.: PCT/CN2015/094047
§ 371 (c)(1),
(2) Date: May 2, 2018

(87) PCT Pub. No.: WO2016/070849
PCT Pub. Date: May 12, 2016

(65) Prior Publication Data
US 2018/0251486 A1    Sep. 6, 2018

(30) Foreign Application Priority Data

Nov. 7, 2014   (CN) .......................... 2014 1 0625571

(51) Int. Cl.
*C07H 17/02*    (2006.01)
*C07H 15/14*    (2006.01)
(Continued)

(52) U.S. Cl.
CPC ............... *C07H 17/02* (2013.01); *C07H 1/00* (2013.01); *C07H 5/10* (2013.01); *C07H 13/10* (2013.01); *C07H 15/14* (2013.01); *C07H 15/207* (2013.01)

(58) Field of Classification Search
None
See application file for complete search history.

(56) References Cited

FOREIGN PATENT DOCUMENTS

| CN | 102250991 | 11/2011 |
| WO | 2010127645 | 11/2010 |

OTHER PUBLICATIONS

Q. Zhao et al., "Metabolic coupling of two small-molecule thiols programs the biosynthesis of lincomycin A," Nature, vol. 518, No. 7537 (2015), 19 pages.

(Continued)

*Primary Examiner* — Layla D Berry
(74) *Attorney, Agent, or Firm* — Hamre, Schumann, Mueller & Larson, P.C.

(57) ABSTRACT

Provided in the present invention are a class of Lincomycin biosynthetic intermediates and a preparation method and use thereof. Specifically provided are Lincomycin biosynthetic intermediates obtained from the genetic modification of a (Continued)

Lane 1: ΔlmbE
Lane 2: WT
Lane 4: Marker

Lane 1: ΔlmbE
Lane 2: ΔlmbE-E3457
Lane 3: Marker

Lincomycin producing bacterium, and a method for the production thereof through fermentation and purification through separation.

3 Claims, 47 Drawing Sheets

Specification includes a Sequence Listing.

(51) Int. Cl.
  *C07H 1/00* (2006.01)
  *C07H 5/10* (2006.01)
  *C07H 13/10* (2006.01)
  *C07H 15/207* (2006.01)

(56) References Cited

OTHER PUBLICATIONS

International Search Report for international appl. No. PCT/CN2015/094047, dated Feb. 6, 2016 (6 pages, including English translation).

Lane 1: ΔlmbE
Lane 2: WT
Lane 4: Marker

Lane 1: ΔlmbE
Lane 2: ΔlmbE-E3457
Lane 3: Marker

Lane 1: Marker
Lane 2: WT
Lane 3: ΔlmbV

Lane 1: Marker
Lane 2: ΔmshA
Lane 3: WT

Lane 1: Marker
Lane 2, 3: ΔlmbC
Lane 4: WT

Lane 1: Marker
Lane 2: WT
Lane 3: ΔlmbD

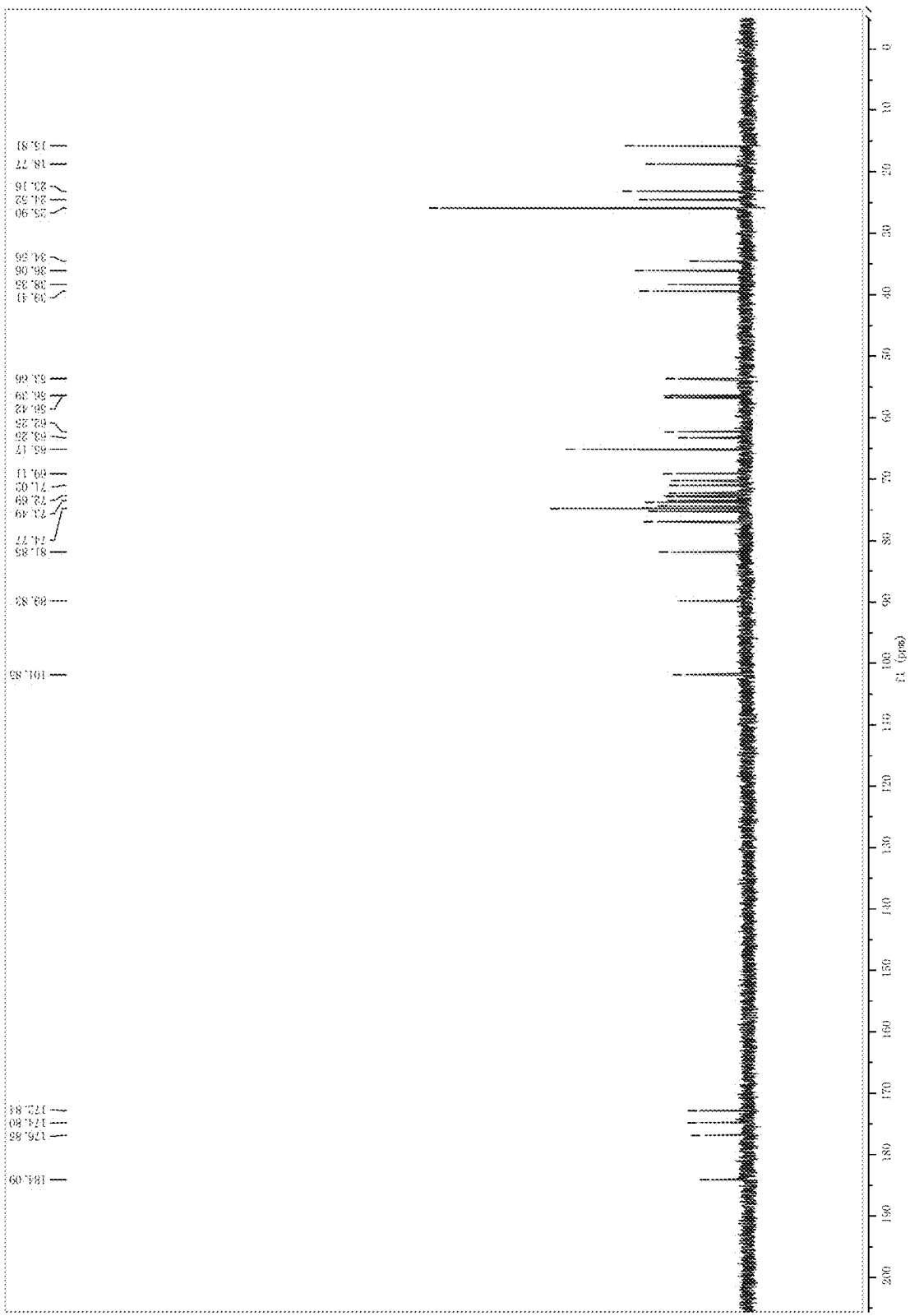

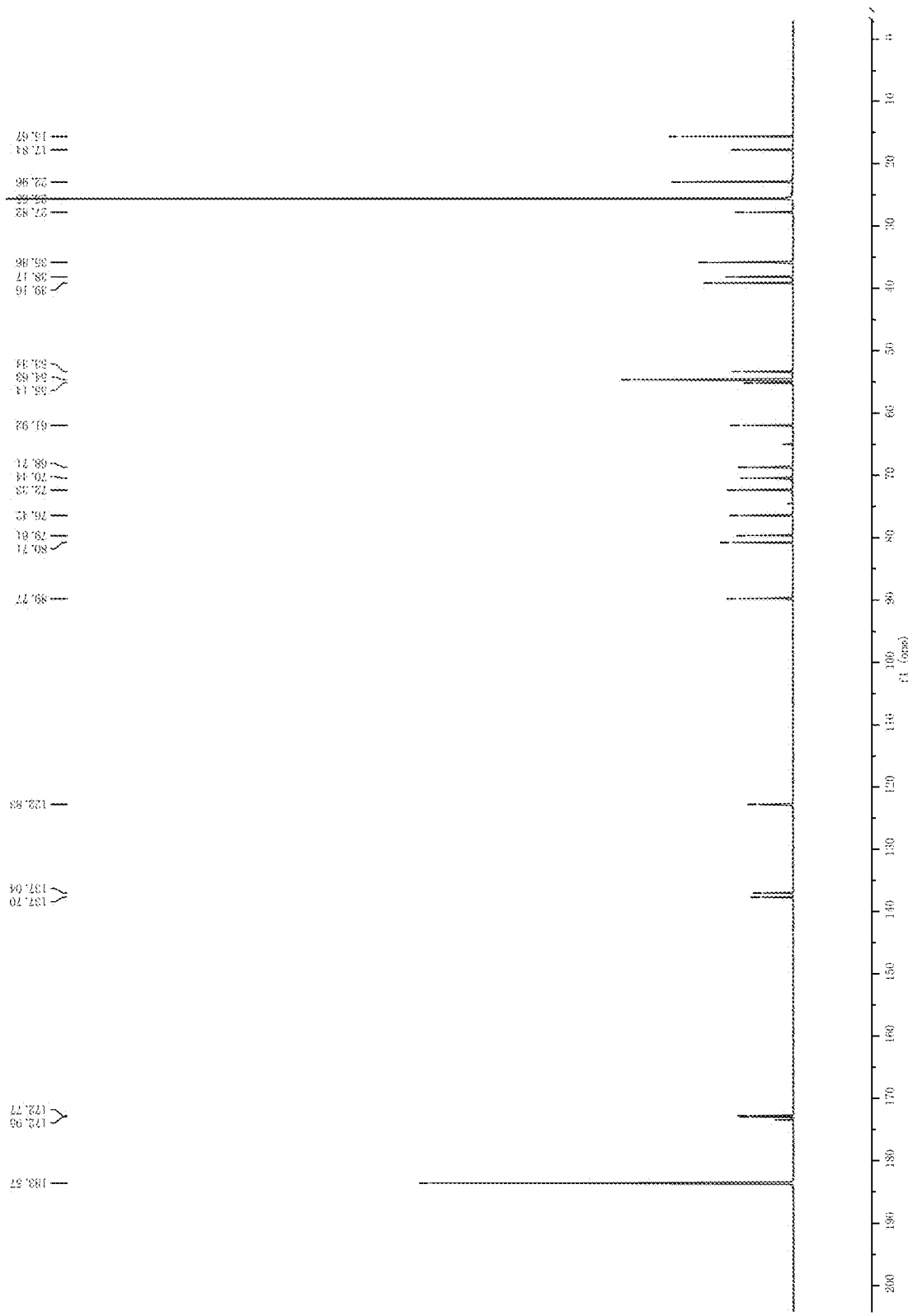

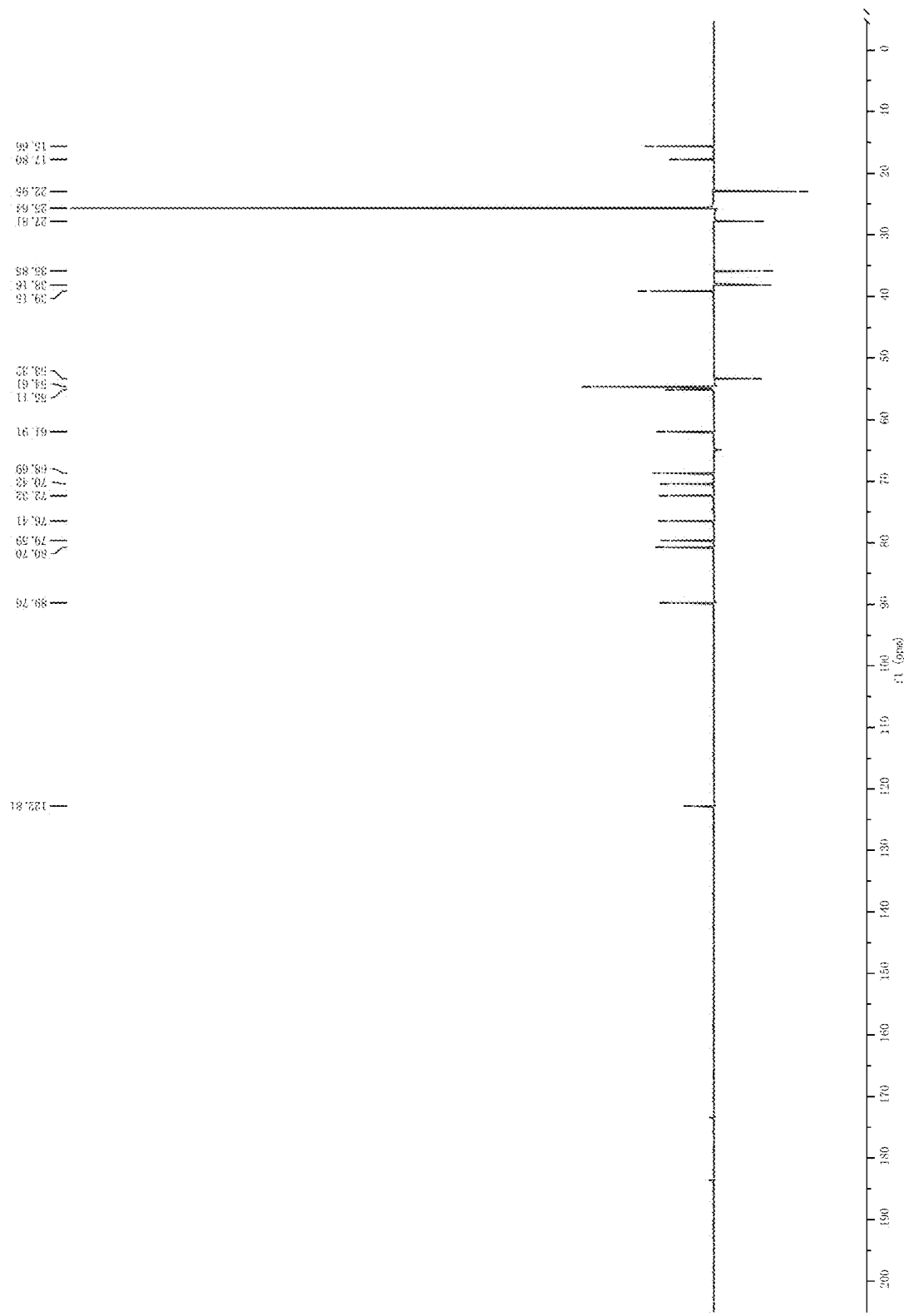

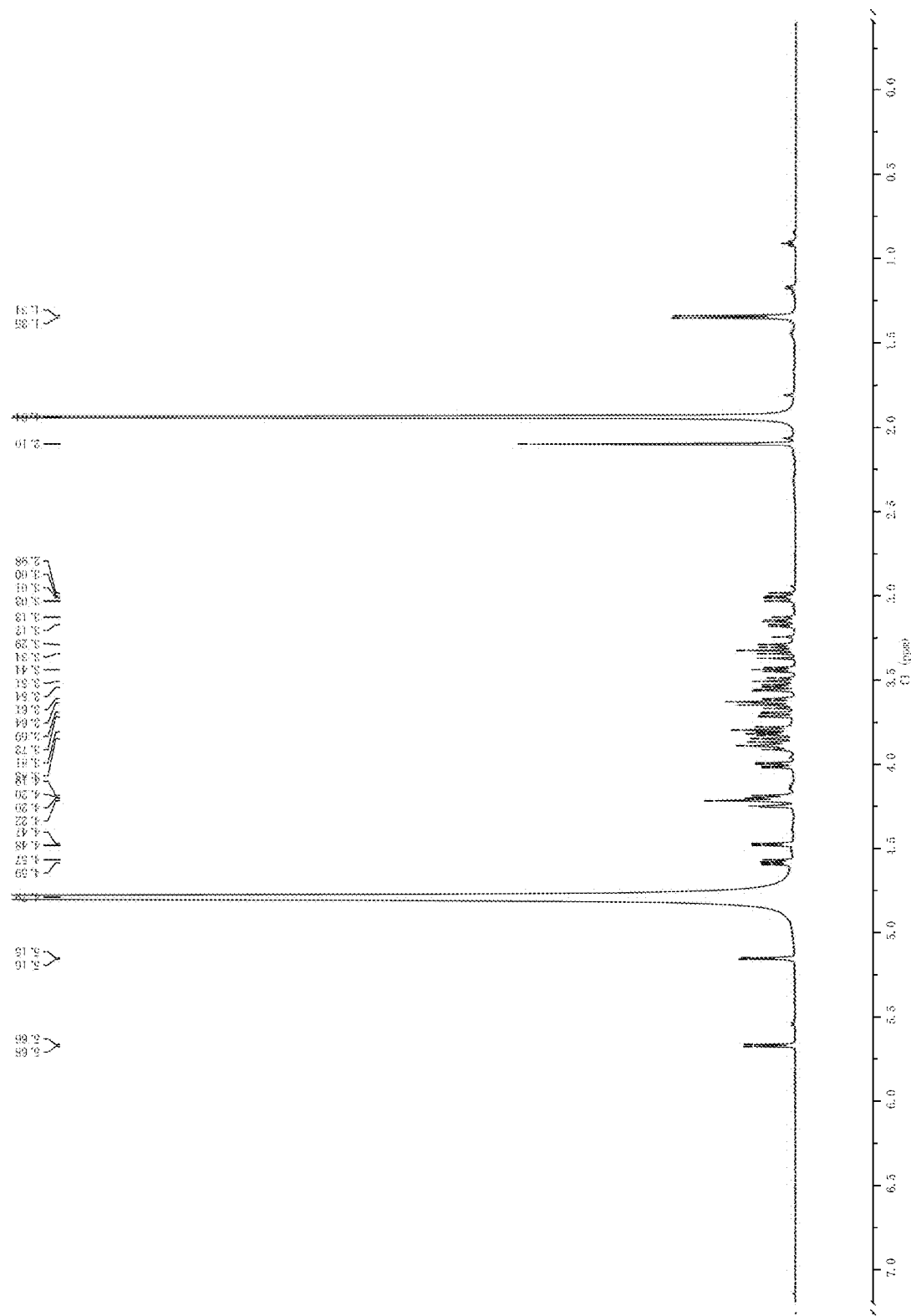

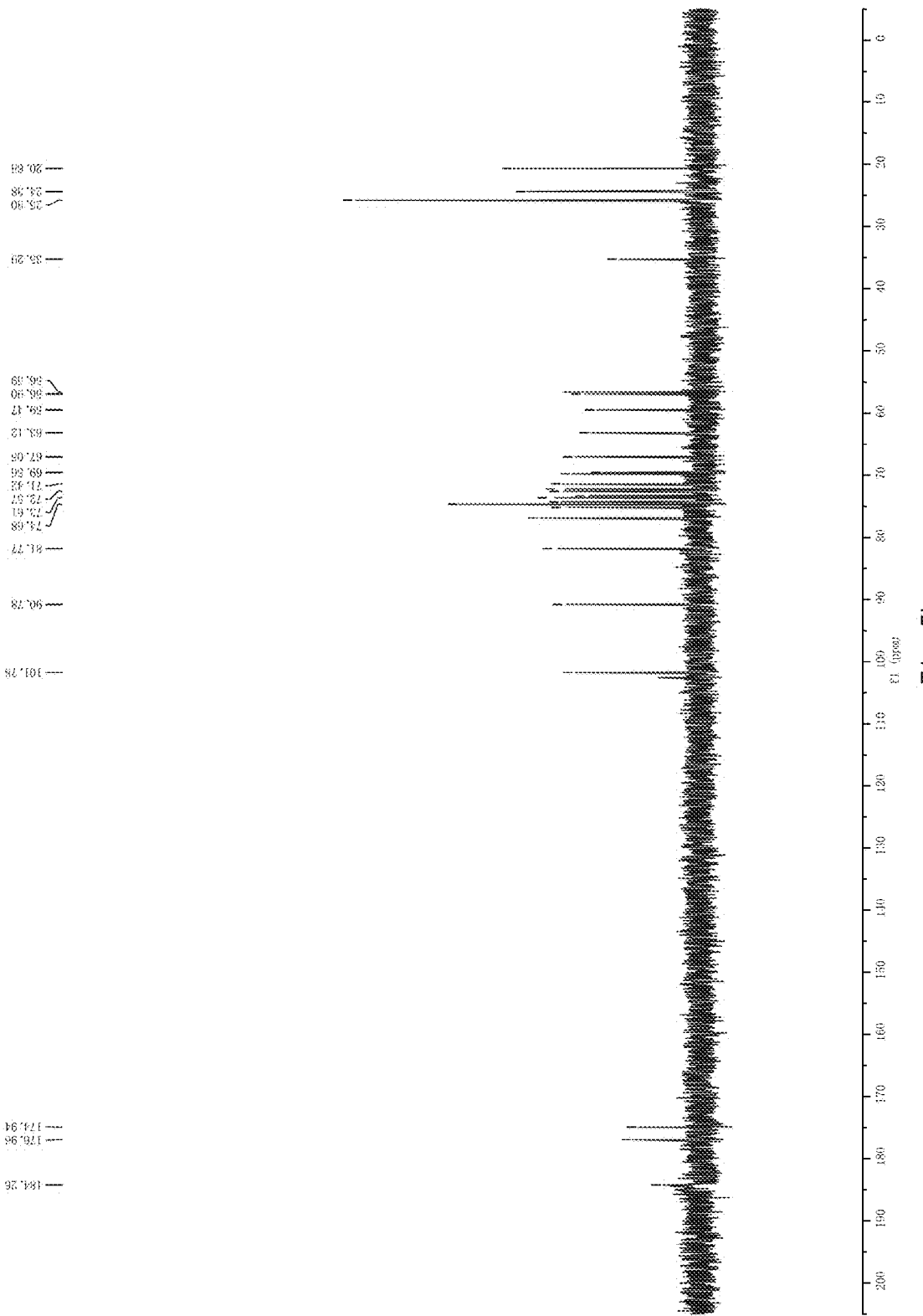

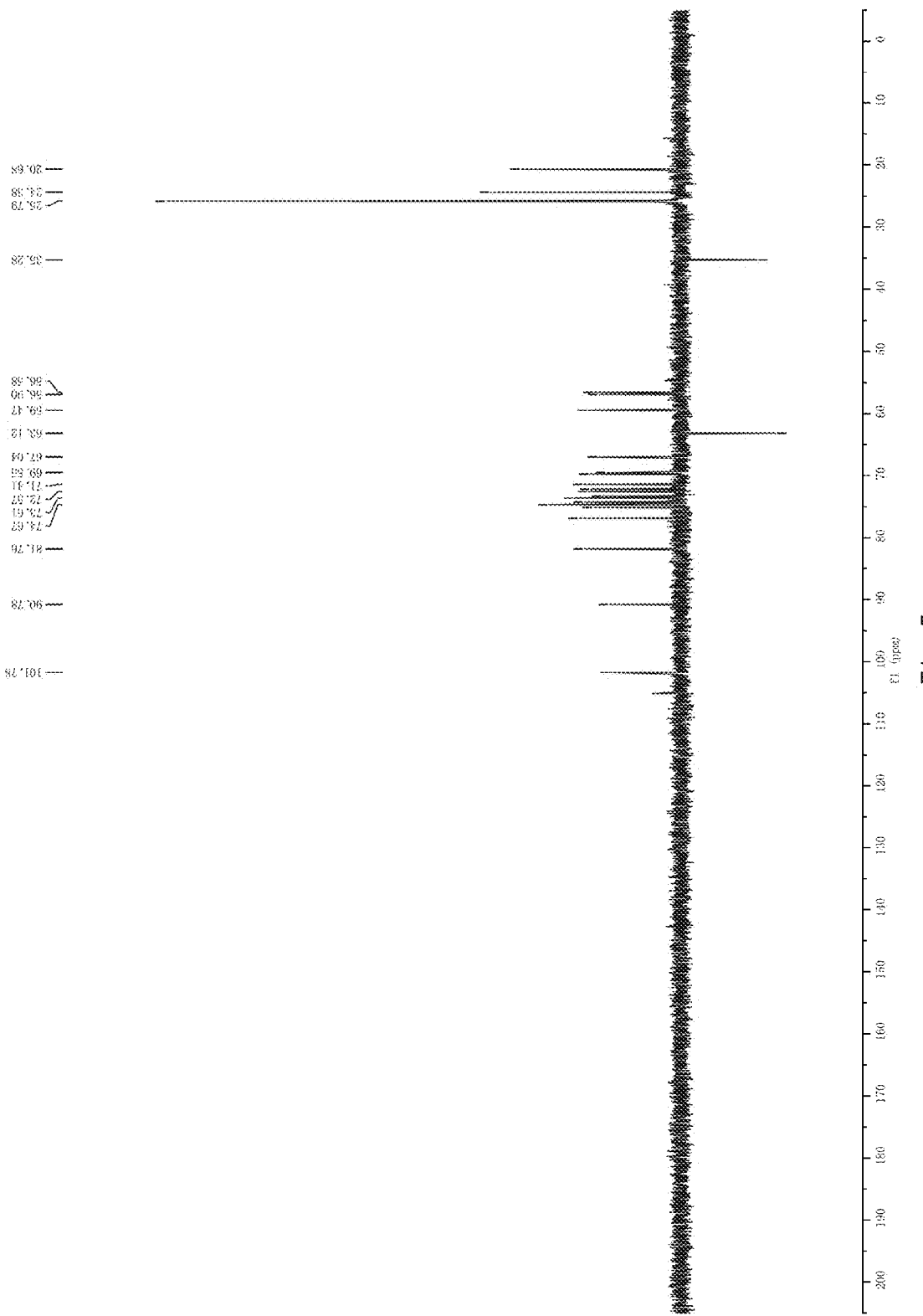

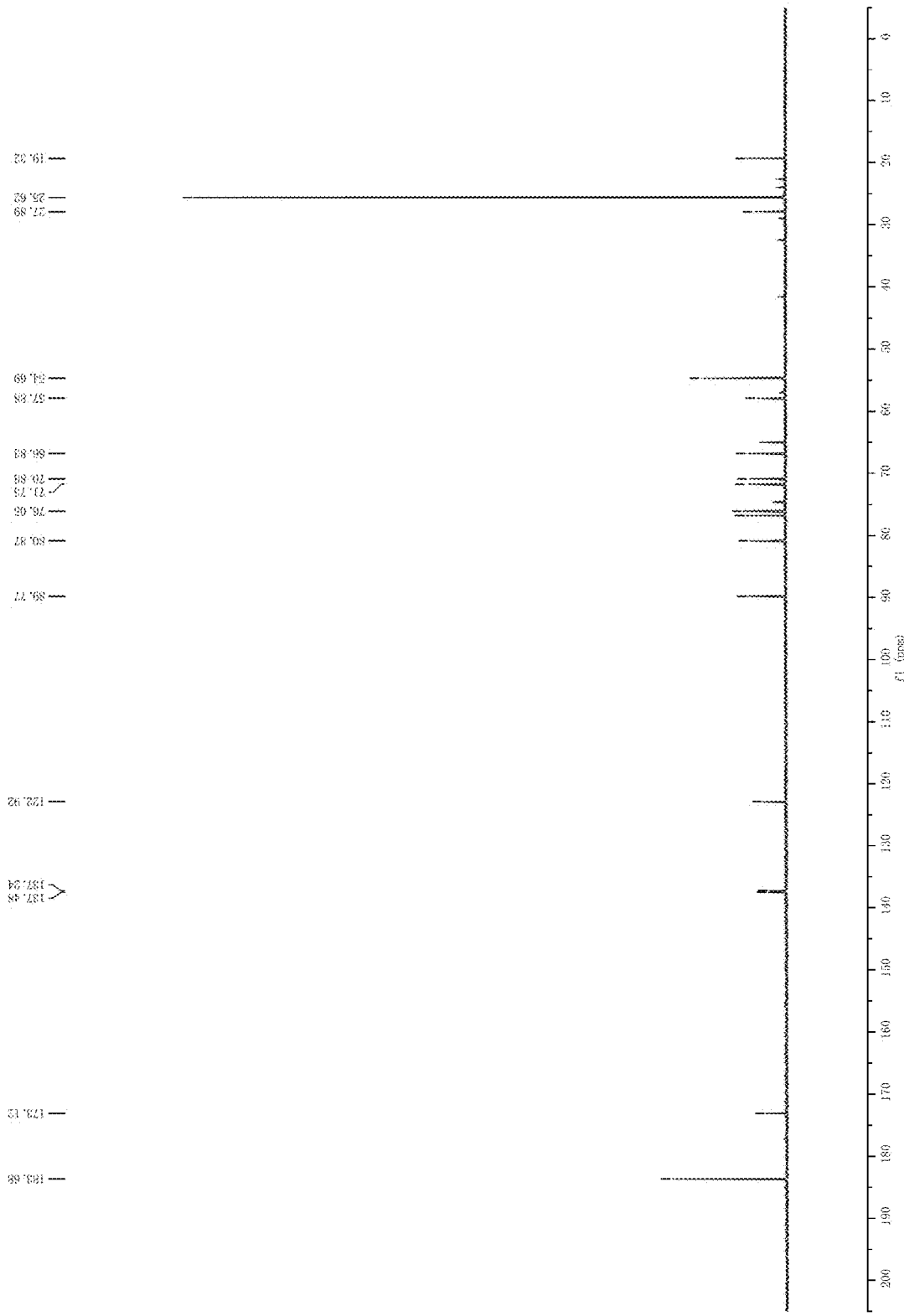

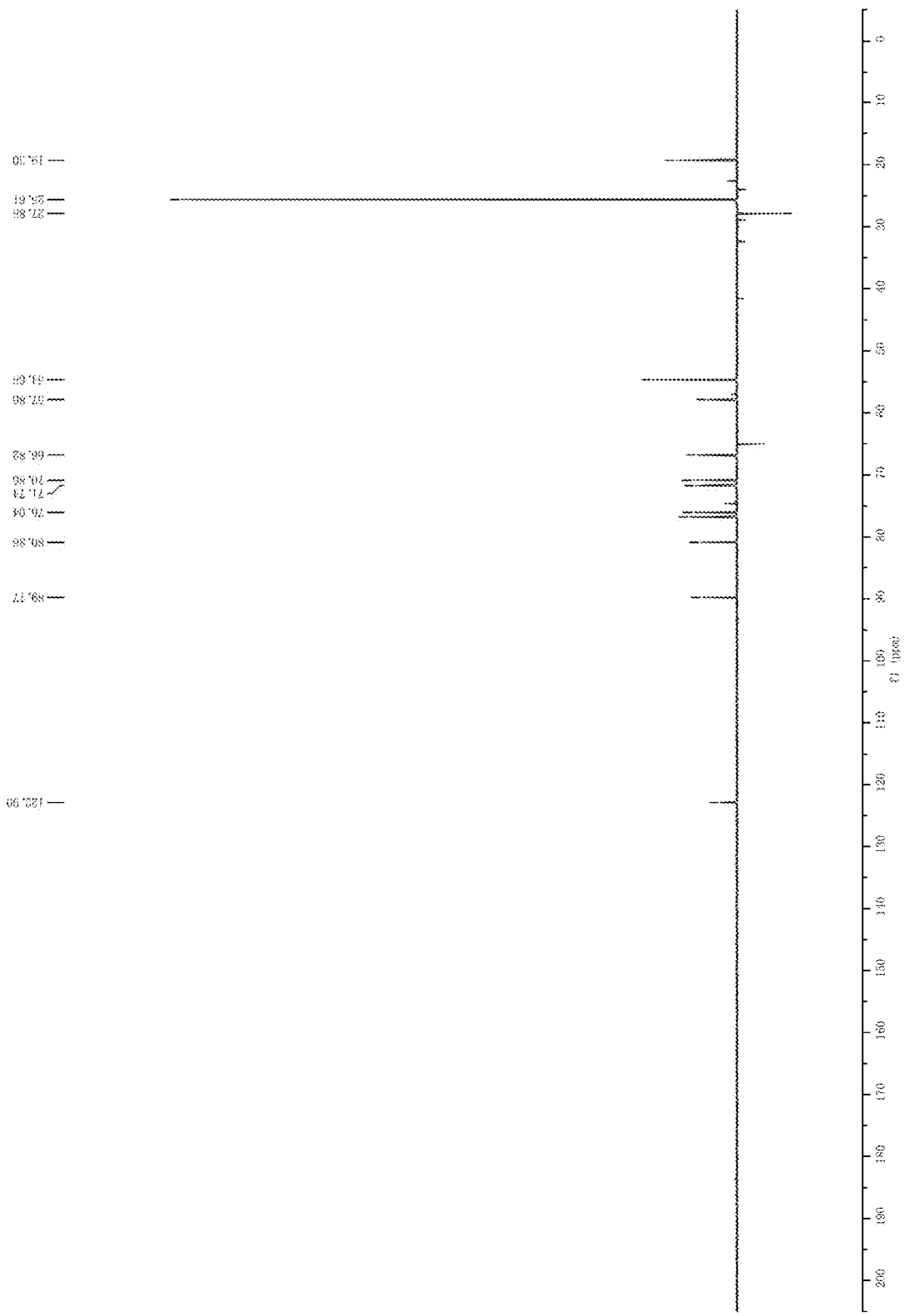

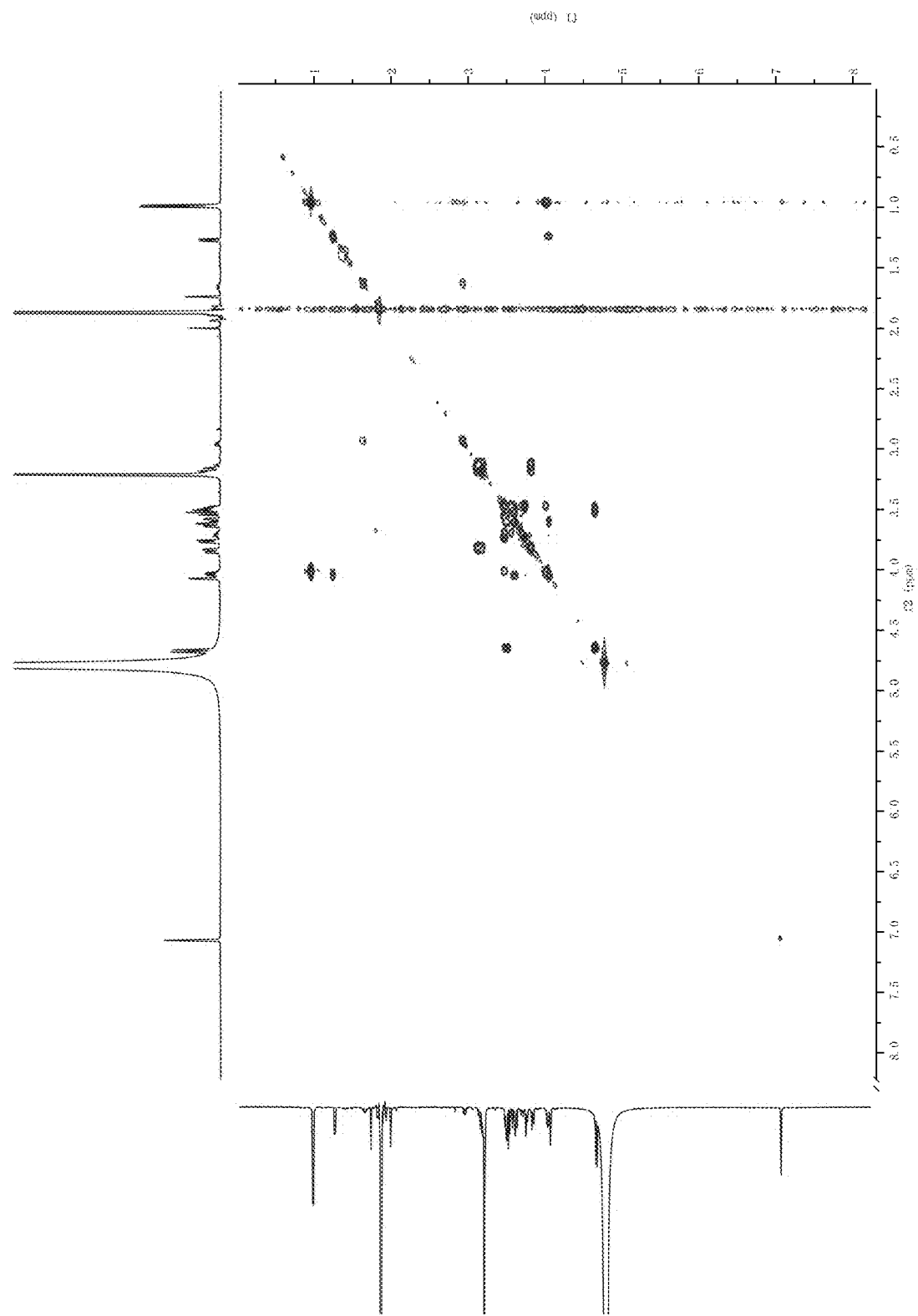

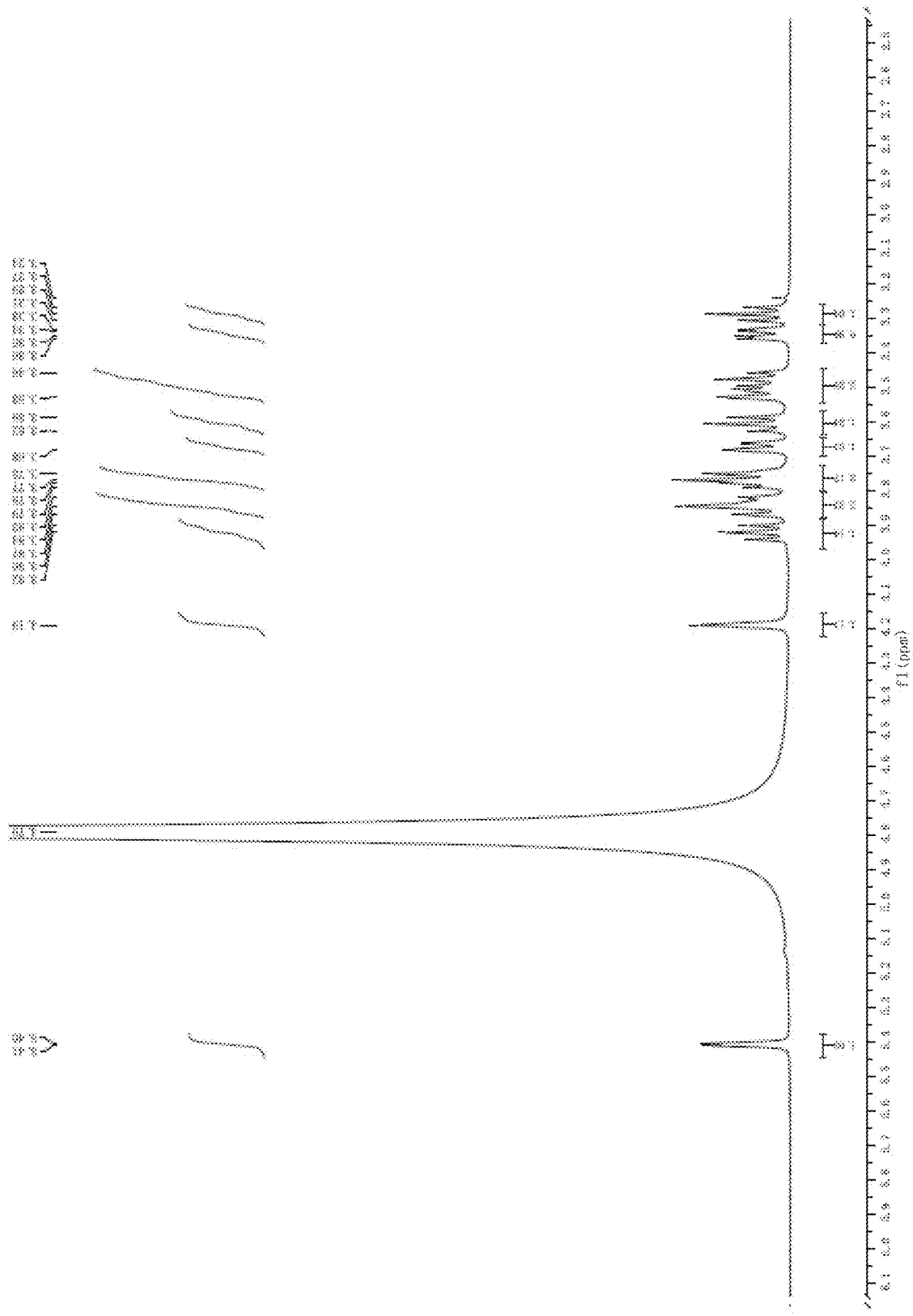

LINCOMYCIN BIOSYNTHETIC INTERMEDIATES, METHOD FOR PREPARATION, AND USE THEREOF

FIELD OF THE INVENTION

The invention belongs to the field of medicine and biotechnology engineering, and specifically, the present invention involves a class of Lincomycin biosynthetic intermediates and a preparation method and use thereof.

BACKGROUND OF THE INVENTION

With the development of molecular biology in the past decade, especially on the basis of the cloning of antibiotic biosynthetic gene clusters and the elucidation of antibiotic biosynthetic pathways, metabolic engineering technology has been proposed and gradually developed to meet the needs of innovative microbial drug research. Currently, in a reasonable, directed and efficient pathway for improving antibiotic strain, principles and techniques of molecular genetics are used to specifically and appropriately modify the synthetic route of natural products in the "Cell Factory" to obtain recombinant strains, thus increasing production or optimize the components of fermentation. The key to the successful use of metabolic engineering is to recognize and understand the biosynthesis and regulatory mechanisms of complex antibiotics at gene and protein function level, which is the molecular and biochemical basis for the genetic manipulation of metabolic pathways in microorganisms. However, due to the lack of understanding of the biosynthesis mechanism of lincomycin, the application of this technology to improve industrial production strains of lincomycin is greatly limited.

Lincomycin and its chemically semi-synthesized downstream product, clindamycin, are widely used clinically for many years. Currently, lincomycin is mainly produced by fermentation of *Streptomyces lincolnensis*. Although Lincomycin has been used clinically for several decades, there are few studies on its biosynthetic pathway.

Chemical syntheses of structural analogues or derivatives of lincomycin have been continuously studied in the art. However, lincosamide antibiotics that have been clinically used so far only include lincomycin and clindamycin which is chemically semi-synthesized based on lincomycin. Production of intermediates or structural analogues of lincomycin biosynthesis by genetically engineered lincomycin-producing bacteria will be conducive to elucidate the biosynthesis pathways of lincomycin, thereby producing new lincosamide antibiotics using combinatorial bio-synthesis method based on the results of biosynthetic mechanism studies.

SUMMARY OF THE INVENTION

The present invention is to provide a type of intermediates of Lincomycin biosynthesis and a preparation method and use thereof.

The present invention is to provide a method for preparing n-propyl proline, disaccharide GlcN-Ins, Mycothiol or ergothioneine.

In a first aspect of the present invention, a compound, the structure of which is shown in formula I, and the pharmaceutically acceptable salts thereof are provided,

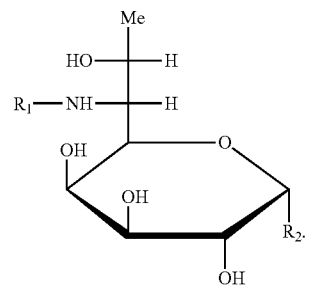

Formula I wherein in the formula I, $R_1$ is selected from a group consisting of H, halogen, $C_{1-8}$ alkyl, $C_{2-8}$ alkenyl, $C_{2-8}$ alkynyl and

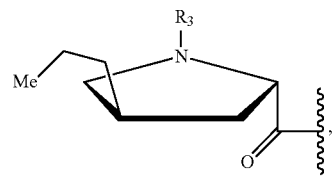

wherein $R_3$ is selected from a group consisting of H, halogen and $C_{1-8}$ s alkyl;

$R_2$ is selected from

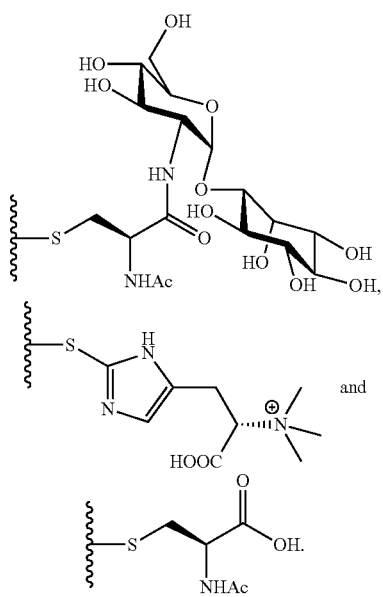

In another preferred embodiment, $R_1$ is selected from a group consisting of H, $C_{1-4}$ alkyl (such as methyl, ethyl, propyl and butyl) and

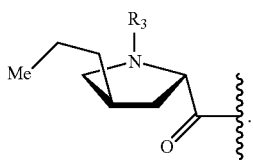

In another preferred embodiment, $R_3$ is selected from a group consisting of H, $C_{1-4}$ alkyl (such as methyl, ethyl, propyl and butyl).

In another preferred embodiment, the structure of the compound is shown in formula Ia:

formula Ia

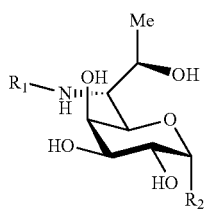

Wherein, in formula Ia, $R_1$ and $R_2$ are described as above.

In another preferred embodiment, the compound has the structure selected from a group consisting of formula I1-I5:

formula I1

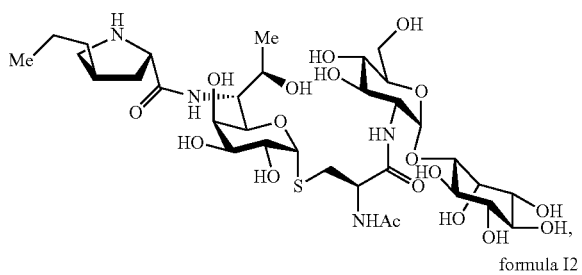

formula I2

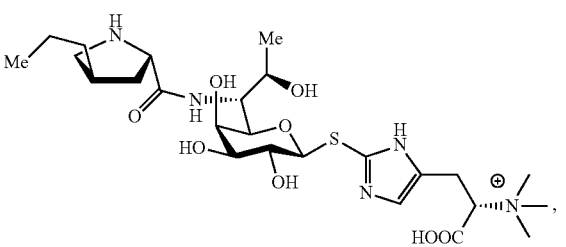

formula I3

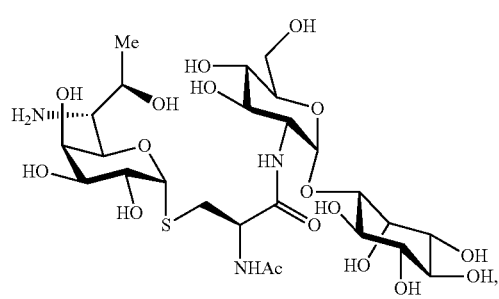

formual I4

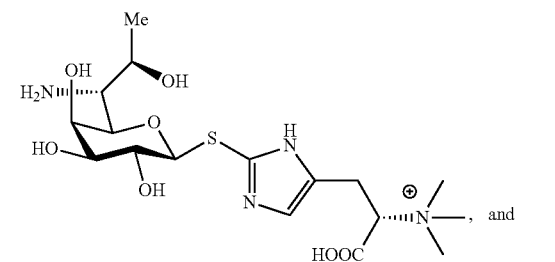

Formual I5

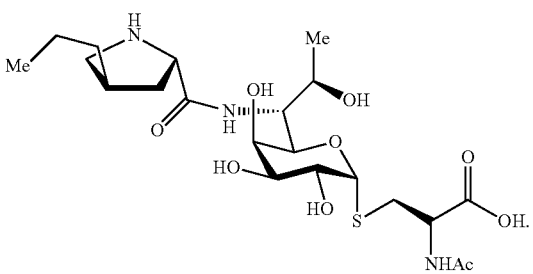

In a second aspect of the present invention, the use of the compound according to the first aspect of the present invention or a pharmaceutically acceptable salt thereof as the raw material for the preparation of n-propyl proline, disaccharide GlcN-Ins, Mycothiol or ergothione is provided.

In another preferred embodiment, the use further comprises: preparation a composition that inhibits the growth of microorganisms using the compound.

In another preferred embodiment, the composition inhibiting the growth of microorganisms includes a drug for treating microbial or bacterial infection.

In a third aspect of the present invention, a composition comprising a compound according to the first aspect of the present invention, or a pharmaceutically acceptable salt thereof, and an optional carrier is provided.

In another preferred example, the carrier includes water and an organic solvent.

In another preferred embodiment, the composition includes a pharmaceutical composition.

In another preferred embodiment, the carrier includes a pharmaceutically acceptable carrier.

In another preferred embodiment, the composition is a raw material composition for preparing n-propyl proline, disaccharide GlcN-Ins, Mycothiol or ergothioneine.

In a fourth aspect of the present invention, a microbial strain is provided, wherein the microbial is *Streptomycin lincolnensis*, and in the strain, one or more genes selected from a group consisting of the following have been inactivated or knocked out:

lmbE, lmbE3457, lmbV, mshA, mshC, lmbC, lmbD, lmbN, and lmbF.

In another preferred embodiment, in the strain, the lmbE and/or lmbE3457 gene have been inactivated or knocked out.

In another preferred embodiment, in the strain, the lmbV, mshA and/or mshC gene have been inactivated or knocked out.

In another preferred embodiment, in the strain, the lmbC, lmbD and/or lmbN gene have been inactivated or knocked out.

In another preferred embodiment, in the strain, the lmbF gene have been inactivated or knocked out.

In another preferred embodiment, the strain is used to prepare the compound of the first aspect of the present invention.

In a fifth aspect of the present invention, a method for the preparation of intermediate compound is provided, comprising:

(a) Using the compound of claim 1 or a pharmaceutically acceptable salt thereof as a raw material for hydrolysis reaction to produce the intermediate compound, wherein the compound or a pharmaceutically acceptable salt thereof is derived from a fermentation product of *Streptomyces lincolnensis*.

In another preferred embodiment, the intermediate compound is selected from a group consisting of n-propyl proline, disaccharide GlcN-Ins, Mycothiol, ergothioneine, or combinations thereof.

In another preferred example, the *Streptomyces lincolnensis* includes any one of the strains described in claim 4.

In another preferred embodiment, the method further comprises: separating the compound of claim 1 or a pharmaceutically acceptable salt thereof from the fermentation product of *Streptomyces lincolnensis* before step (a).

In another preferred example, in the step (a), one or more selected from a group consisting of the compounds of Formula I1, Formula I2, and Formula I5 are subjected to hydrolysis reaction to generate n-propyl proline compound.

In another preferred embodiment, the hydrolysis reaction is carried out under alkaline condition.

In another preferred embodiment, the method further comprises the step: fermenting the microbial strain according to the fourth aspect of the present invention to obtain the compound of Formula I1, Formula I2, and/or Formula I5.

In another preferred embodiment, the method further comprises the step: fermenting a *Streptomyces lincolnensis* mutant strain to obtain a compound of Formula I1, Formula I2, and/or Formula I5, wherein in the *Streptomyces lincolnensis* mutant strain, one or more of the genes selected from a group consisting of lmbE, lmbE3457, lmbV, mshA, mshC and lmbF gene are inactivated or knocked out.

In another preferred example, in the step (a), one or more selected from a group consisting of the compounds of Formula I1 and Formula I3 are subjected to hydrolysis reaction to generate disaccharide compound GlcN-Ins.

In another preferred embodiment, the method comprises the step: fermenting the microbial strain according to the fourth aspect of the present invention to obtain the compound of Formula I1 and/or Formula I3.

In another preferred embodiment, the hydrolysis reaction is carried out under alkaline condition.

In another preferred embodiment, the method further comprises the step: fermenting a *Streptomyces lincolnensis* mutant strain to obtain a compound of Formula I1 and/or Formula I3, wherein in the *Streptomyces lincolnensis* mutant strain, one or more of the genes selected from a group consisting of lmbE, lmbE3457, lmbC, lmbD and lmbN gene are inactivated or knocked out.

In another preferred example, in the step (a), one or more selected from a group consisting of the compounds of Formula I2 and Formula I4 are subjected to hydrolysis reaction to generate ergothioneine.

In another preferred embodiment, the method comprises the step: fermenting the microbial strain according to claim 4 to obtain the compound of Formula I2 and/or Formula I4.

In another preferred embodiment, the hydrolysis reaction is carried out under acidic condition.

In another preferred embodiment, the method further comprises the step: fermenting a *Streptomyces lincolnensis* mutant strain to obtain a compound of Formula I2 and/or Formula I4, wherein in the *Streptomyces lincolnensis* mutant strain, one or more of the genes selected from a group consisting of lmbV, mshA, mshC, lmbC, lmbD and lmbN gene are inactivated or knocked out.

In the sixth aspect of the present invention, a method for the preparation of Mycohiol is provided, comprising:

(1) Preparing Disaccharide Compound GlcN-Ins

Using the compound of claim 1 or a pharmaceutically acceptable salt thereof as a raw material for hydrolysis reaction to produce the disaccharide compound GlcN-Ins;

(2) Chemically Synthesizing Mycothiol from GlcN-Ins.

In the seventh aspect of the present invention, a preparation method for compound 1 of the first aspect of the present invention is provided, which comprises following steps:

(a) fermenting the strain of the fourth aspect of the present invention to produce the compound of the first aspect of the present invention; and (b) isolating the compound of the first aspect of the invention from the fermentation product; and optionally converting the compound into a pharmaceutically acceptable salt thereof.

According to the eighth aspect of the present invention, a method for non-therapeutically inhibiting the growth of microorganisms or killing microorganisms in vitro is provided, comprising the step of using the compound according to the first aspect of the present invention or its pharmaceutically acceptable salt in a place in need thereof.

In the ninth aspect of the present invention, a method of preparing pharmaceutical composition is provided, which comprises the following step: mixing the compound of the first aspect of the present invention and a pharmaceutically acceptable carrier to form the pharmaceutical composition.

It should be understood that, in the present invention, each of the technical features specifically described above and below (such as those in the Examples) can be combined with each other, thereby constituting new or preferred technical solutions which need not be specified again herein.

DESCRIPTION OF THE DRAWINGS

The following figures are intended to illustrate specific embodiments of the present invention and are not intended to limit the scope of the present invention.

FIG. 1 shows the results of electrophoresis of an in frame knockout mutant of a lincomycin-producing strain.

FIG. 3 shows the results of NMR analysis of compound 1, FIG. 3*a*, 1H NMR spectrum; FIG. 3*b*, 13C NMR spectrum.

FIG. 4 shows the results of NMR analysis of compound 2, FIG. 4*a*, 1H NMR spectrum; FIG. 4*b*, 13C NMR spectrum; FIG. 4*c*, DEPT135 NMR spectrum.

FIG. 5 shows the results of NMR analysis of compound 3. FIG. 5a, 1H NMR spectrum; FIG. 5b, 13C NMR spectrum; FIG. 5c, DEPT135 NMR spectrum.

FIG. 6 shows the results of NMR analysis of compound 4. FIG. 6a, 1H NMR spectrum; FIG. 6b, 13C NMR spectrum; FIG. 6c, DEPT135 NMR spectrum; FIG. 6d, COSY NMR spectrum.

FIG. 7 shows the results of NMR analysis of compound 5. FIG. 7a, 1H NMR spectrum; FIG. 7b, 13C NMR spectrum.

FIG. 8 shows the results of NMR analysis of n-propyl proline, FIG. 8a, 1H NMR spectrum; FIG. 8b, 13C NMR spectrum.

FIG. 9 shows the results of NMR analysis of the disaccharide compound GlcN-Ins, FIG. 9a, 1H NMR spectrum; FIG. 9b, 13C NMR spectrum.

EMBODIMENTS FOR CARRYING OUT THE INVENTION

Figure 1A:
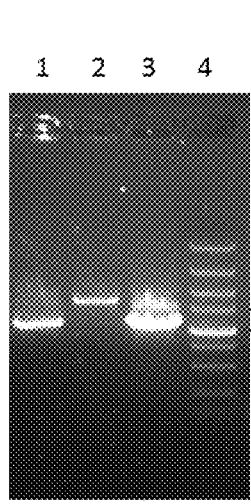
FIG. 1*a*, lmbE knockout mutant.

After extensive and intensive studies, the present inventors obtained a mutant strain of *Streptomycin lincolnensis* by cloning of a lincomycin biosynthetic gene cluster and gene knockout. The in vitro biochemical activity of the proteins related to the biosynthesis of lincomycin was studied. The biosynthesis mechanism of lincomycin was studied in vitro and in vivo. Surprisingly, it was discovered that certain strains of *Streptomycin lincolnensis* mutants produced new compounds, and then the compounds were isolated and identified through extensive fermentation. The present invention is completed on this basis.

Active Ingredients

As used herein, the terms "active ingredient of the present invention", "compound of the present invention" and "lincomycin biosynthesis intermediate of the present invention" are used interchangeably and refer to lincomycin biosynthesis intermediate such as compounds of formula I.

It should be understood that the term also comprises the crystal forms, pharmaceutically acceptable salts, hydrates or solvates of the compound of the present invention.

In a preferred embodiments of the present invention, the term "$C_{1-8}$ alkyl" refers to linear or branched alkyl with 1 to 8 carbon atoms, such as methyl, ethyl, propyl, isopropyl, butyl, isobutyl, sec-butyl, tert-butyl, or similar groups.

In a preferred embodiment of the present invention, the term "$C_{2-8}$ alkenyl" refers to a straight or branched alkenyl group having 2-8 carbon atoms such as ethenyl, propenyl, 1,2-butenyl, 2,3-butenyl, butadienyl, or similar groups.

In a preferred embodiment of the present invention, the term "$C_{2-8}$ alkynyl" refers to an alkynyl group having 2 to 8 carbon atoms, e.g., ethynyl, propynyl, iso-alkynyl group, butynyl group, alkynyl isobutyl, sec-butynyl, t-butynyl group, or the like.

In a preferred embodiment of the present invention, the term "halogen" refers to F, Cl, Br and I.

As used herein, the term "pharmaceutically acceptable salt" refers to a salts suitable for use in pharmaceutics formed by the compound of the present invention with an acid or base. The pharmaceutically acceptable salt includes inorganic and organic salt. A preferred type of salt is a salt formed by the compound of the present invention and acid. A salt can be formed from a cation and a charged group (e.g., an amino group) on a compound of the present invention. Suitable cations include hydrogen ions, sodium ions, 50 potassium ions, magnesium ions, calcium ions, and ammonium ions. Bases suitable for salt formation include, but are not limited to, hydroxides of alkali metal and alkaline earth metal (such as NaOH, KOH), oxides of alkali metal and alkaline earth metal, carbonates of alkali metal and alkaline earth metal (such as $Na_2CO_3$), ammonia, and so on.

In a preferred embodiment of the present invention, the compound structure is as follows:

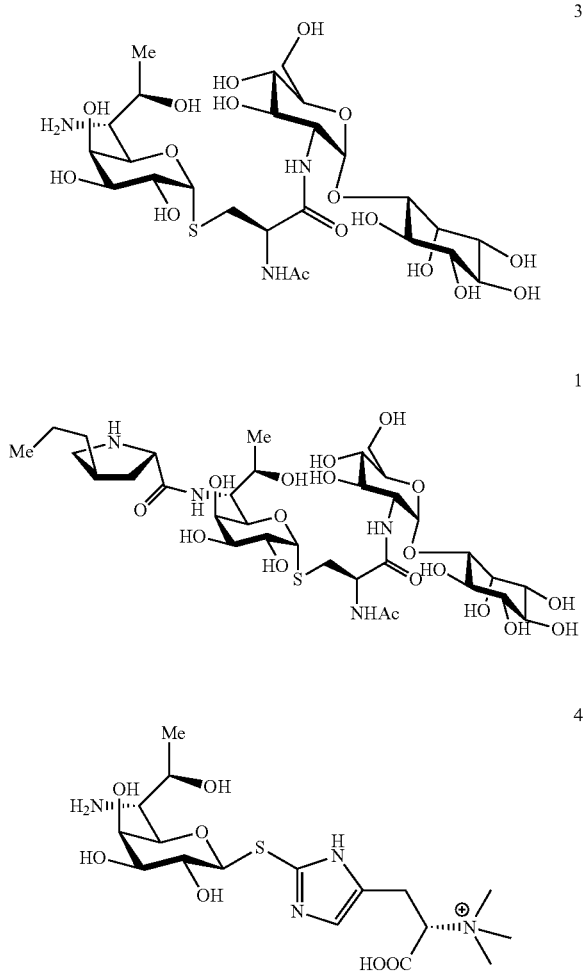

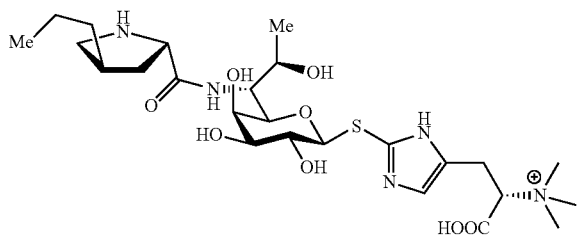

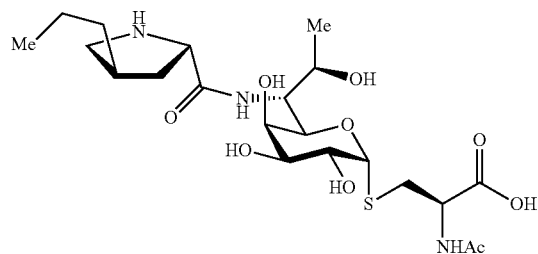

The compound of the present invention can be used as a structural analog for preparing other lincosamide antibiotics and used to produce downstream products such as n-propyl proline, disaccharide compound GlcN-Ins, and/or ergothioneine through hydrolysis.

In a preferred embodiment of the invention, n-propylproline is prepared by hydrolysis of compound 1, 2 or 5.

In a preferred embodiment of the present invention, the process for preparing n-propylproline (PPL) is as follows:

In a preferred embodiment of the present invention, the disaccharide compound GlcN-Ins is prepared by hydrolysis of compound 1 or 3. GlcN-Ins can be used as a raw material to synthesize Mycothiol (the chemical synthesis method refer to: *Org. Lett.* 6, 365-368, 2004; *Org. Lett.* 12, 2630-2633, 2010).

In a preferred embodiment of the present invention, the disaccharide compound GlcN-Ins is prepared by the following steps:

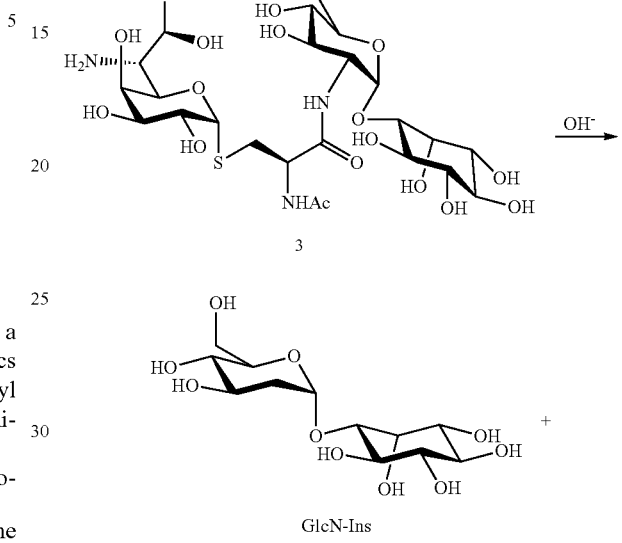

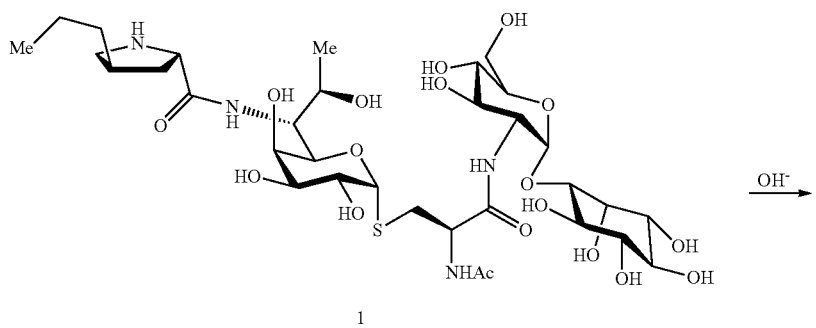

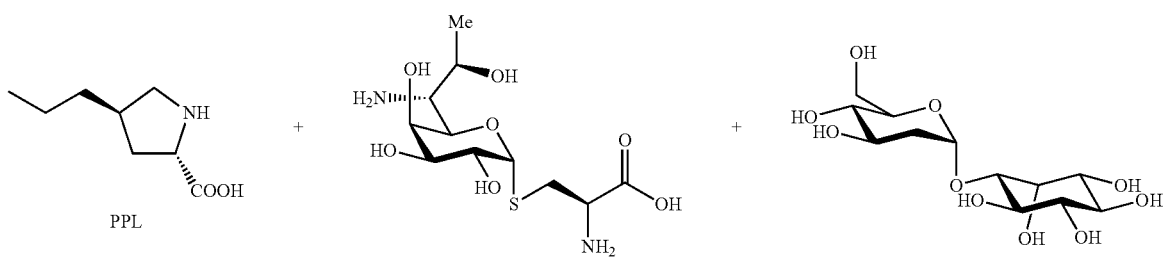

-continued

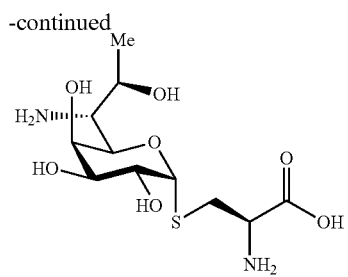

In a preferred embodiment of the invention, erythrothioneine is prepared by hydrolysis of compound 2 or 4.

In a preferred embodiment of the present invention, the erythrothioneine is prepared by the following steps:

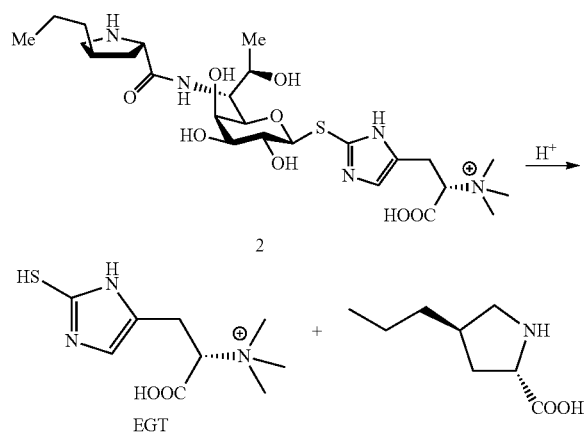

Starting Strain

As used herein, the term "starting strain of the present invention" or "starting microorganism of the present invention" refers to *Streptomycin lincolnensis* with the number NRRL ISP-5355. The starting strain of the present invention is stored in the Agricultural Research Service Culture Collection (NRRL), numbered *Streptomycin lincolnensis* NRRL ISP-5355. It should be understood that the starting strain includes not only the strain numbered *Streptomycin lincolnensis* NRRL ISP-5355 but also its derivative strains.

Engineered Strains

The invention also provides engineered strains that can be used to produce the compounds of the invention.

In a preferred embodiment of the present invention, several mutant strains of *Streptomycin lincolnensis* that produce the lincomycin biosynthesis intermediate of the present invention are provided.

Preparation of Active Ingredients

The present invention provides a method for preparing a compound of formula I, comprising the steps of:

Fermenting the genetically modified strain of *Streptomycin lincolnensis*;

Extracting the compound of formula I from the culture medium.

The strains are discarded by centrifugation, and the supernatant liquid is adsorbed by macroporous resin, washed with distilled water, and then soaked in methanol. The macroporous resin was removed by filtration. The filtrate is concentrated under vacuum and dried, and the obtained paste is firstly roughly separated on a gel column, further purified with HPLC preparation to give the desired product.

Functional Gene

As early as 1995, Peschke et al. obtained a 35 kb lincomycin biosynthesis cluster by chromosome walking in *S. lincolnensis* 78-11 using three lincomycin resistance genes IprA, lprB and llmC [Mol Microbiol. 1995, 16(6): 1137-1156]. The Janata team in Czech also cloned a 38217-bp lincomycin biosynthetic gene cluster in a low-yield strain of lincomycin *S. lincolnensis* ATCC 25466 in 2008. By bioinformatics analysis, the gene cluster contains 30 reading frames (ORF), consisting of 27 putative biosynthetic and regulatory genes (lmb) and 3 resistance-associated genes (lmr). Heterologous expression in *S. coelicolor* M145 and *S. coelicolor* CH 999 confirms that the gene cluster includes a complete gene associated with lincomycin synthesis [Folia Microbiol. 2008, 53(5): 395-401]. However, when aligning each gene product with the known protein sequence by sequence analysis, it is found that for several genes, homologous proteins can not be found at all, thus being impossible to infer the function. Even if the possible functions can be inferred from the homologous protein comparison, the functions of most genes in the biosynthesis of lincomycin are still unknown.

Preferably, the lincomycin biosynthetic gene cluster involved in the present invention can be found in [Folia Microbiol. 2008, 53(5):395-401].

In a preferred embodiment of the present invention, the polynucleotide sequence of lmbE gene is as follows:

(SEQ ID NO.: 1)
ATGACTCAGTGCCTGCTGACCGTCCACGCGCACCCGGACGACGAGGCCTC

CCGCGGCGGCGCCACGGTCGCCCACTACACCGCGCAGGGCGTCCGCGCCG

TCCTGGTCACCTGTACCGACGGCGGCGCCGGCGAGGTGCTCAACCCCGCC

GTCACCGACGACTTCACCCCCGAACGGTTCGTCGCCGTCCGCAGCGCCGA

ACTCGACGCCAGCGCACGGAACCTGGGCTACTCGGCCGTGCACCGGCTCG

GCTACCGCGACTCCGGCATGGACGGCACGGCGGGCGGCGCCGAGGCCTTC

GTACGGGCCCCGCTCGACGAGGCCGCCACCCGCCTCGCCCGGGTGATCGC

GGACGAACGCCCCGACGTGGTGATCGGATACGGCACCAACCACACCCGCG

ACCCGCACCCCGACCACATCCGCGCGAACGAAGTGCTGACGCGCGCCGTC

GACCTCCTCGACCACACACCCGCCGTCTACCACATCGCCTTCTCGCGACG

TCGCCACCGCGCCTTGCACCAGGCCTGCGTCGACAGCGGGGTGCCCAGCC

CGTACGAGGGCGGCCTGAGCGCCCCGCCGGGCGCCTTCGACGACGAGTGG

ATCACCACACTCGTCGACGTGACCAAGGGCGACGCCGTCGAGCGCAGGCT

CGACGCGCTGCGCAGTCACGTGACCCAAGTACCGCCCGCCTCCGGCTGGT

TCGCGCTGTCACCGCAGCAGCTGCGGGACGCCTTCCCGTACGAGGAGTAC

ACCCGCGTCGGCGCCGCGCCCCGGGAAGCCGTGGTGCACGACCTGTTCAC

CGCTCCCGCGTGA

In a preferred embodiment of the present invention, the polynucleotide sequence of lmbE3457 gene is as follows:

(SEQ ID NO.: 2)
ATGGCCGTGCACGCCCACCCCGACGACGAGTCGAGCAAGGGCGCGGCCAC

CATGGCGAAGTACGTGTCCGAGGGGGTGGACGTGCTGGTCGTGACCTGCA

CGGGAGGGGAGCGCGGCTCCATCCTCAACCCCAAGCTCCAGGGGGACGCG

-continued

TATATCGAGGAGCACATCCATGAGGTGCGCAAGAAGGAGATGGACGAGGC

GAGAGAGATCCTCGGCGTCAAGCAGGAGTGGCTCGGGTTCGTCGACTCGG

GCCTGCCCGAGGGGGACCCGCTGCCGCCGCTGCCGGAGGGCTGTTTCGCC

CTGGAGGACGTCGACAAGGCGGCCGGTGAGCTGGTGAAGAAGATCCGCTC

GTTCCGTCCCCAGGTGATCACCACCTACGACGAGAACGGCGGCTACCCGC

ACCCCGACCACATCATGACCCACAAGATCTCGATGGTGGCGTTCGAGGGT

GCCGCGGACACCGAGAAGTACCCGGAGCAGGAGTTCGGCCCCGCGTACCA

GCCGCAGAAGATCTACTACAACCAGGGCTTCAACCGTGAGCGCACCGAGG

CCCTGCACAACGCGCTGGTCGAGCGCGGCCTGGAGTCCCCCTACGGCGAC

TGGCTCAAGCGCTGGGAGGAGTCCGGGATGCAGCAGCGGACGCTCACCAC

GCACGTCCCGTGTGCCGAGTTCTACGAGATCCGCGACAAGGCCCTGATCG

CCCACGCCACGCAGATCGACCCCGACGGCGGCTGGTTCCGGGTGCCGCTG

GATCTCCAGAAGGAGGTCTGGCCGACCGAGGAGTACGAGCTCGCGAAGTC

CCTCGTCGATACTTCCCTCCCCGAGGCGGACCTCTTTGCGGGCATCCGCG

ACAATGCCTGA

In a preferred embodiment of the present invention, the polynucleotide sequence of lmbV gene is as follows:

(SEQ ID NO.: 3)
TTGCAGCGCAAGGGACTGGCCCGGCTCGGGTCGGGTGTCACGGCACTGGC

CGACGAGGGAAGACACCTGCGGGCCTGGCTCACGAGCGCCGACGCGGCGG

CGTGGCGACGGCCCACACGCTGTGCGGAGTGGAACGTCCGGGACGTCGTC

GCGCACCTGGCGAGCGGCGAGCTGTACAACCAGGCATGCGTGCACGACGA

CATCGCCTCGCTCGGCGAGTGGGCCGACGACGAGGCGTACAACGTCGGCC

AGGTGGAGATGCGCCGCCACCTGAGCCACCGCGACGTCTTCGCGGAGTGG

GACGAGCGCCACCGGGACGTGGTGGCCGCCTGGGGGGCCATGGACCCGGC

CGACCCGCTCACCACGAGCTGGGGACCGTACCTGGTCGGCCTGCAGGCGT

GGCACATCGCGTCGGAGTACGCGACCCACGCCGACGACATCGGGGTCCCC

GTCCCCGCGGAGCGGGCCGCCTCCCGGCTCGACTGGCGCCTCGCCTTCTC

CCAGTACGCGGTCGAGGAGTGCGAGCTGGGCCTTACGGTCGAGCCCGCCG

AGGGCGACAGTGTGCTCGTGCGGGACGGGGCCGGGGCCGGGGCCGAACTC

GTACTGACCCGTGAGCAGTTCGTGGCCGCGGTCAGCGCCCGGCTGCCGTA

CGACGCCGTCGCCGACGACCCCGCCGTTCACGCGCTGCTACGGCGCATGA

CGGTGCTGGTGGGGCCGTGA

In a preferred embodiment of the present invention, the polynucleotide sequence of mshA gene is as follows:

(SEQ ID NO.: 4)
GTGAGCCAGTACGTCAGCAGGCTCCAGCGTCGCTCCCAGGCCGCCACCCC

CCGGCTGCGCCTGCACCGCCGCCCCGCCGCGTCGCCATGCTCTCCGTGC

ACACCTCGCCGCTGCACCAGCCGGGCACCGGCGACGCGGGCGGCATGAAC

GTCTACATCGTGGAGCTCGCCCAGCGCCTCGCCGCGATCAACATCGAGGT

GGAGATCTTCACGCGGGCGACCACCGGCGGACTCCCGCACTCGGTCGAGC

TCGCCCCGGGCGTCCTCGTCCGGCATGTCGACGCCGGCCCGTACGAGGGC

CTGGCCAAGGAGGAGCTGCCCGCGCAGCTGTGCGCCTTCACGCACGGCGT

GATGCAGGCGTGGGCGGGCCACCGCCCCGGCTACTACGACCTGGTGCACT

CGCACTACTGGCTTTCCGGCCACGTCGGCTGGCTCGCCGCCCAGCGCTGG

GGCACCCCCTGGTGCACGCCATGCACACCATGGCCAAGGTCAAGAACGC

CAACCTGGCCGACGGCGACACCCCCGAGCCCGCCGCCCGTGTCATCGGCG

AGACCCAGATCGTCGCCGCAGCGGACCGCCTCATCGCCAACACCGCCGAG

GAGCGCGACGAACTCGTACGGCACTACGCCGCCGACCCCGACAAGGTCGC

GGTCGTGCACCCCGGCGTGAACCTCGACCGCTTCCGCCCCGCCGACGGCC

GCGCGGCCGCCCGCGCCCGCCTCGGGCTGCCCCAGGACGCCCTGATCCCG

CTGTTCGCGGGCCGCATCCAGCCCCTGAAGGCCCCCGACGTGCTCCTGCG

CGCCGTGGCGGTCCTCCTGGACGAACGCCCCGACCTGCGCTCCCGCCTCC

TCGTCCCGGTCGTCGGCGGTCTCAGCGGCAGCGGCCTCGCCAAGCCGGAG

GGCCTCCAGAAGCTGGCCTCCCGCCTCGGTATCGCGGACGTCGTACGGTT

CCACCCGCCCGTCGGGCAGGAGCAGCTCGCCGACTGGTTCCGGGCCGCCT

CCGTGCTCGTCATGCCGTCGTACAGCGAGTCCTTCGGACTGGTCGCCATA

GAGGCGCAGGCGGCCGGCACCCCCGTGCTCGCGGCCGCGGTCGGCGGACT

CCCGGTCGCCGTCCGCGACGGGCAGACCGGTTTCCTCGTACGAGGGCACA

ATCCCGCCGACTACGCGCGCGTGCTGCGCGACTTCGCCGACAGCCCCGAG

CTCGCGCCCCGCATGGGCGAGGCCGCCGCCCGGCACGCCGAGTTCTTCGG

CTGGGACACCGCGGCCGCCGCCACCGCCGACGTCTACACGGCCGCGACCC

AGTCGCACCGCCGTCACGTACGCTCCCACCATGGGTGA

In a preferred embodiment of the present invention, the polynucleotide sequence of mshC gene is as follows:

(SEQ ID NO.: 5)
ATGCATGCCTGGCCCGCTTCCGAGGTCCCCGCCCTGCCTGGTCAGGGCCG

CGACCTGAGGATCCACGACACCGCGACCGGCGGCCTCGTCACCCTCACCC

CCGGTCCCGTCGCCCGTATCTACGTCTGCGGCATCACGCCGTACGACGCG

ACCCACATCGGTCACGCGGCGACCTACAACGCGTTCGACCTCGTGCAGCG

CGTGTGGCTCGACACCAAGCGGCAGGTCCACTACGTCCAGAACGTCACCG

ACGTCGACGATCCGCTCCTGGAGCGGGCACAGCGCGACGCCATCGACTGG

GTCGCCCTCGCCGAGAAGGAGACCGCCCTCTTCCGCGAGGACATGACCGC

CCTGCGGATGCTGCCCCCGCGGCACTACATCGGCGCGGTCGAGGCGATAC

CCGGCATCGTGCCGCTCGTCGAGCGGCTGCGGGACGCGGGCGCCGCGTAC

GAACTCGAAGGGGACGTGTACTTCTCCGTCGAGTCCGATCCGCACTTCGG

CGAGGTCTCCGGCCTCGACGCCGCCGCCATGCGGCTGCTGTCCGCCGAGC

GCGGCGGCGACCCCGAGCGGCCCGGCAAGAAGAACCGCTCGACCCGATG

CTGTGGATGGCCGCCCGCGAGGGCGAGCCCAGCTGGGACGGCGCCTCGCT

GGGGCGCGGCCGGCCGGGCTGGCACATCGAGTGCGTCGCGATCGCCCTCG

ACCACCTCGGGATGGGCTTCGACGTCCAGGGCGGCGGCTCCGACCTCGCC

TTCCCGCACCACGAGATGGGCGCCTCGCACGCCCAGGCGCTGACCGGCGA

GTTCCCCATGGCCACGGCGTACGTCCACGCCGGCATGGTCGCCCTCCACG

GCGAGAAGATGTCCAAGTCCAAGGGCAACCTGGTCTTCGTGTCGCAGCTG

CGCCGCGAGGGCGTCGACCCCGCCGCCATACGGCTCGCGCTGCTCGCCCA

CCACTACCGGGCCGACTGGGAGTGGACCGACCAGGTGCTGCGGGACGCCG

TCGACCGCCTCGGCCGCTGGCGTGCCGCGGTCTCCCGGCCCGACGGCCCG

TCCGCCGAGGCCCTCGTCGAGGAGATCCGCAAGGCGCTCGCCGACGACCT

GGACGCCCCGGCCGCCCTGGCCGCGGTCGACCGCTGGGCCGCCTCGCAGG

AGGAGCACGGCGGCACCGACATCGGCGCGCCGGGCGTGGTGACACGAGCG

GTGGACGCGCTGTTGGGCGTGGCCCTGTGA

In a preferred embodiment of the present invention, the polynucleotide sequence of lmbC gene is as follows:

(SEQ ID NO.: 6)
ATGTCGTCCTCCGTTCGACTCTCCACACTCCTCGCCTCGGCCGCCGAGGC

GAGGCCCGAGGCCCCGCCGTCCTGGGGGAGACCCGGCTCCCGGTCACCT

ATGGGGAGCTGGCCGCGCGGGCGGGCGGCATCCAGGCCGCCCTGGCAGGC

CTGGGGGTGCGCGCCGGTGACCGGGTAGCGCTGCTGTCCGGGCGGACCGA

CGCGGACGCCGTGGCCGCGGTGCACGCGATCCTGGCCGCGGGCGCCGTGT

ACGTGCCGCTCGACGCCGCGTCGCCGCCCGCGCGGTGGGCTTCGGTGAGC

CGGGTCTGCGCGCCCACCGCCGTGGTGGGCGAACGCGCGCTGCTCGACCG

GTTCGCCGCCGCCGTACCGGGGCCGCGGCGGCTCGCCCTGCCATCGGACG

GGGACGAGCTGCCCGCGGGCCGCCTCGACCCCGTCCGGAGCGACGGCACC

GATGTCGCGTACCTGCTCACCACCTCCGGCTCCACCGGCGTTCCCAAGTG

CGTGGCCCACACCGGTGCGGGCGCCGTCGCCTTCCTGGAGTGGATGGTCG

GCGCGTTCCCGGTGGGCGGCGACGATGTGTTCGCCTGCCACGCCCCGCTG

CACTTCGACGTGTCGGTGGCCTCGGTGCTCGGCTCCGCGCTGGGCGGCGC

GGCCCTGGCCCCGGTGCCCGTGAACTGTCCGGGTTTCCCGTCGAGCTGG

CCACCTGGATCGCCGAACGCGCCGTCACCGTATGGCTCTCCGTGCCCTAT

CCGCTCGCCCGCCTGTCCGGACTGGAGGAGCGGGCCGCGCGTGAGCGCCT

CGCCACCTTGAGGACGGTCGTGTTCGCCGGTGACGTCTTTCCGCACCAGC

GGCTCGCCGCACTGATGCGCTGCGCGCCCGGGGCCCGGTTCCTCAACATC

TACGGCCCGACCGAGACCAACGGCTGTACGTACGAGGTCGTGGACGCCCC

GCCCGCCGGCCCCGTGCCCATCGGCCGGCCCGTCGAGTGCGCCGAGTGCT

GGGTCGAGGACGACGACGGGCGGCCGGTCGACGCGGTGGGGTCGGTGGGT

GAACTCGTCGTCGCGGGCCCACGGTGGCCGCCGGATACTGGGGCGTCGA

GGGGCACGGAGCCGAGCGGTTCCGCACGGGGGAGACCTGTCCGGGCGGCC

GGGCCTACGCCACCGGGGACCAGGTCCGCGTCCTGCCCGGGGGCCGGTAC

GCCTTCCTCGGCCGCATGGACAACATGATCAAGATGCGCGGGCAGCGGTT

CGAGCTGGAGGAGGTGGAGAACGCTGTACGGCTCGCTCCCGGCGTCGAGG

ACTGCTGCGTGGTGAAGGTGGACGTCCGCGACGATCACTCCCGCCTCCTC

GCCGTCGTGGTCGGGCCCGGCGCCGGCGACCCGCGCACCCTGCGCGAGCA

CTGCCTGACCAGGCTGCCGTCGTGGGCGGTGCCGCACCGGTTCCTCACGG

CCGCCGCGCTGCCCCTGGGCTCCACCGGCAAGGTGGACCGCCGCGCGCTC

AGGGAGGAACTCGTCACACGCGGGGAGTGA

In a preferred embodiment of the present invention, the polynucleotide sequence of lmbD gene is as follows:

(SEQ ID NO.: 7)
ATGGCGGTATCACCCCAGTCGGTTCGGTTGCCGGAACACGCGCCGCA

CTGCGAGATCGGCTGCGCGGCGAACGTGGCGAAGAGGGTCGGTGTCGACT

TCCCGCGGCACGTGGCCGGGTCCCAGTGGGCGCTGCGCACCTTCGTCCGG

GAGCCCGGCGACATCCCGCAGCCCATGCTGGACCGCACGCATCTGACGTT

CGGCGCGCACGGCGAGGGCTGGCCCACCGCCCTCGCGGGGATCACGGACG

GCACCGTGCACGACCGCCGGGTGGCGCGTTCGGAGCTCCGGAGGTGCTG

CGGGACGACCTCGCCCGGGGCGGCAGTCTGCTGTTCCTGGAGGACCGCGG

CTGCCCATGGCTGCACTCCGCCGGCCCCGGGCTGCTGCCGCACACGGTGA

CCCCGGACGGTGTCGACGCGGCCGGGGTCTGGCAGCTGATCGAGGGGCAC

AGCTGGTGGGCGGGCCGGTACCCGATGGCGGAGGCCGACCTGCTGGCCGC

GGCCTACCCGGACCCCGACCCGCACCATGTGGCGGGCCGGGTCCTGAGCC

TGCGTCTGGCCCTGACGCCCGAGCGTCGCGCGGCCCTGGACGCCCTCGCC

CTGGACCGGCTGCGGGACAGCGTGCGCGCCTACCTCACGGGGGGCGACGG

CCGGCTCGACACCCCGGCGGGCACGCTGGTGTGGACGGACGGGCAGGCGG

CGGTCGCGGAACTGCTGGACCGGCTGCGGGGCTGGGAGTACCTGTGCGCG

CTCGCCGCCGACGACGGGGCCGGCGTCGAGCAGGGCATCGACATCGCCGT

GGGCCGGTATCTGTTCCTGGGCCTGGCGGACGAGCTGGCCTACACGTCGT

ACGCCCGCGCGGGCGCCCGGCGCCTGACCCGACGCCTCGGCGCTCTCGCG

GACATCGGCGACGAACACCTCCCCGACGTGGTGTGGCAGCGGGCGTGGCG

CAGCGCCCAGCGGTTCTACCGGTCGCTGCGCGCGGAGCACTTCGACGCCC

TGTTGCACGACATCGACGCGGCGGGGGTGGCCGACGCCGCTTGTGCGCGC

CGGCTCGCGGAGGTCCTGTAG

In a preferred embodiment of the present invention, the polynucleotide sequence of lmbN gene is as follows:

(SEQ ID NO.: 8)
GTGAGCACTCTGGACGAGGTCCTCGCCCTGCTCCGCACCATCGCGCC

GAGCGGCGACGAGACCGAACTCACCGCCGACACCCTCCTGTTCAGCTCCG

GCCTGCTCGACAGTCTCGCCCTGGAGGAGCTGCACGTCGCCATCGAGGAG

CGCTGGGCGCCCATCCCACCCATGGAACTGGCGCGGGCGAACTTCGACAC

CCCGGCCGCCATCGCCGCGACGGTGCCCGTATCACCCATGAGGAGACCC

CTGTGAGTGTTGTGAGGAACCTCCTGTCCGACTCGGGCCGGCTGACCGCC

GACCTCGCACCGGACGCTATCGAGCGCGGTGCGCAGCTGCTCTTCGACAC

CTGGCACGCCGGCGGCACCACCCTGTCCTGCGGCAACGGCGGCTCGGCCT

CGACCGCCTCCCACTTCGCCGCCGACCTCGCCAAGCTCACCATCGTGCCC

-continued

```
GGACAGCGCCGCATGCGGACGCTGTGCCTGAACGACAACGCCTCCGCGTT

CTCGGCGTGGACCAACGACGAGGGCTTCCCCGTCGTCTACCGGGAGCAGG

CCGAGCCCTGGCTGGAGCCCACCGCCACTCTGGTCGCGTTCTCCGTGCAC

GGCGGCTCCCGCGGGGCGAAGTGTCGGCGAACCTGCCCGCCGTCGCCCG

CCTCGCCAAGGAACGCGGCGCCGCCGTGGTCGCGGTCACCGGCTTCGACG

GCGGCGCCCTCGGCGACCTCGCGGACGTCCACATCAACATCCCGCACGCC

ACCGAGCCCGTGGCGACCCCGCTGATCGAGTCGCTGCACGTCCTCGTCCA

CCACGCCCTGTGCGTCGGCGCACGCGCCCTGATCCTGGAGAAGGCGGGGG

AGCCGGCATGA
```

In a preferred embodiment of the present invention, the polynucleotide sequence of lmbF gene is as follows:

(SEQ ID NO.: 9)
```
ATGACCGCCACGGCGAGCGGCGCGCAGACCGCCGCACCGGAACGGCT

CACCGACGACGGCTGGCTGATCCGGCGCACATCCGTCGACACCGTCCGCC

CCTTCGACGACCCGAGCGCCCAGTGGATGCTGGACCGCGCCCAGGCCCGT

CTGCCGCTGTACCTGCTGCACGTCGCCGACCACGCGGAGGCCACGCCGCC

CGGACTGCGCGAGGCCCTGCACGCCCAGGACGCGGCCCCCTGCGACGGCC

TGCTGTTCTCCCAGTACGGCCTGCCGGAGCTGCGCCGGCGGCTCGACGCC

TGGCTCGCCGCCGACGAGGAGTGGGACACCGCGGCGGAGCCGCTCGTCAG

CGTCGCGTGGTCGGGCACCGGCGCGGCCATCTTCGACCTGCTGCGCATGC

TCAAGGACGGCCGCCCGGGCCCCAGCGCCGTGCTGCTGCCGCGCCCCGGG

TGGGGATATGACATGTCGGTGCGCGACACCGGACACGTACCGGTGAGTTA

CGAGGTGCCCCCCGAGTCCCCGCACGGCCCGGACCCCGCGCACCTGGAGG

AGGCGTGGCAGCGGTGCCGCAGCGAGGGCCTCGACGTCGCCTGCATCCTC

ATCAACCCGCAGCACAACCCGTGGGCGGCAACTGGACCCCGAGTTCCT

CGCCGCCGTCGCCGCCCTCGCCGAACGTGAGCGAGTGCCCGTCCTGGTGG

ACAACGCCTTCTACGGGCTGACCGCCGAGGACGTGCGCCCCACCAGCGCG

GTCCGGCTCCTCGGCCATCTCGTCGGCCAGGAACTCCTGGTGTCGGTGCG

CAGCCTGAGCAAGCAGTTCGCGTGCAGCGGCTGGGCCCTGGGAGCCGTCG

CGGGCAGCCCGGGTCTGGTCTCGGCGTACTCCGGCCGCTGGCGCTGTCTG

CGGGAGCCGACCGCGGGCTTCCGCGCCCAGGCGGCGATGCGGCCTGGCT

CGGGGGCGCCGAACCCGAGCGCTTCACCCGGCGCCGCCGATCCGAGGCCA

CCCGGCACGCCAGGCTCCTGCGCACCACACTGCGCGCGGCGGGGCTGCCC

GACGACGCCGTCCTGCACCACGGCGGCGCCCCCTTCACCCTGCTGCGGCC

CCCGGGCGGCAGCACGTCGAGGAGGTGCGCGAGCAGACCGTCGTGCGGC

ACGGCGTCCTGCTCGGCCTGGAGCGGGACGCGCGCGAACGGCCGTGGTTC

AAGGTCTGGCTGGGCCGGGACAGCAGCGTCTTCGAACCCGCGGCGCGGC

CCTCGGCGACGCCGCGGCCGAGTGGCGGTACCGGTGA
```

Pharmaceutical Composition and Administration Thereof

The compound of the present invention has excellent bacteriostatic (antibacterial) activity and thus can be used as an anti-bacterial agent (or antibiotics), and its properties is beneficial to form injections.

The compounds of the present invention can be administered to mammals (e.g. humans) and can be administered orally, rectally, parenterally (intravenously, intramuscularly or subcutaneously), topically, and the like. The compounds can be administrated alone, or in combination with any other pharmaceutically acceptable compounds. It should be pointed out that the compound of the present invention can be administrated in mixture.

Solid dosage forms for oral administration include capsules, tablets, pills, powders and granules. In these solid dosage forms, the active compounds are mixed with at least one conventional inert excipient (or carrier), such as sodium citrate or $CaHPO_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1, 3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, 50 polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with other active ingredients (such as antibiotics).

When the pharmaceutical compositions are used, a safe and effective amount of compound of the present invention is applied to a mammal (such as human) in need of, wherein the dose of administration is a pharmaceutically effective dose. For an individual weighed 60 kg, the daily dose is usually 1-1000 mg, preferably 20-500 mg. Of course, the particular dose should also depend on various factors, such as the route of administration, healthy status of the individual, which are well within the skills of an experienced physician.

The Main Advantages of the Present Invention are:

1. The present invention provided a class of Lincomycin biosynthetic intermediates with noval structure (which can be referred as "lincomycin derivatives").

2. The present invention provides a genetic modification method for a lincolomycin-producing strain. High-yield production of a high-purity lincomycin biosynthesis intermediate product can be achieved through fermentation production, separation and purification of the strain.

3. Based on the lincomycin analogs of the present invention, it is not only conducive to the preparation of other structural analogues of lincosamide antibiotics, but also facilitates the production of a variety of extremely useful intermediate compounds (including n-propyl proline, disaccharide GlcN-Ins, and/or ergothioneine) by simple hydrolysis.

4. The preparation of the intermediate compound by the biological method of the present invention less affects environment and is of mild conditions and suitable for large-scale industrial production.

5. The method of the present invention not only can conveniently prepare a variety of useful intermediate compounds, but also avoids the use of expensive and complex full-chemical synthesis, and therefore has low cost and other comprehensive advantages and application prospects.

The present invention will be further illustrated below with reference to the specific examples. It should be understood that these examples are only to illustrate the invention but not to limit the scope of the invention. The experimental methods with no specific conditions described in the following examples are generally performed under the conventional conditions (for example, according to J. Sambrook et al., Molecular Cloning: A Laboratory Manual (New York: Cold Spring Harbor Laboratory Press, 1989), or according to the manufacturer's instructions. Unless indicated otherwise, parts and percentage are calculated by weight.

Unless otherwise defined, the technical terms and scientific terminology used herein are of the same meanings as with that familiar to all to those skilled in the art. In addition, any methods and materials similar or equal to that recorded can be applied in the present invention. The preferred embodiments and the materials described herein are for demonstration purposes only and are not intended to limit the scope of the present invention.

Example 1 Construction of in Frame Knockout Mutant of Lincomycin

1. Construction of a Recombinant Plasmid for in Frame Knockout

Primer Design:

The primer sequence for the left arm DNA fragment of the PCR clone lmbE gene is as follows:

```
                                                   (SEQ ID NO.: 10)
Primer 1:    5'-TATGAATTCCACCTTCACCACGCAGCAGTCC-3'

(SEQ ID NO.: 11)
Primer 2:    5'-TATTCTAGACCTTCCCGTACGAGGAGTACAC-3'
```

The primer sequence for the right arm DNA fragment of the PCR clone lmbE gene is as follows:

```
                                                   (SEQ ID NO.: 12)
Primer 3:    5'-TATTCTAGACGAACCGTTCGGGGGTGAAGTC-3'

(SEQ ID NO.: 13)
Primer 4:    5'-TATAAGCTTCCCGTTGCACACGACGTTTCAC-3'
```

The primer sequence for the left arm DNA fragment of the PCR clone lmbE3457 gene is as follows:

```
                                                   (SEQ ID NO.: 14)
Primer 5:    5'-TATGAATTCCTGTTCACCTCCTACGGCGAC-3'

(SEQ ID NO.: 15)
Primer 6:    5'-TATTCTAGAATCCGCGACAAGGCCCTGATC-3'
```

The primer sequence for the right arm DNA fragment of the PCR clone lmbE3457 gene is as follows:

```
                                                   (SEQ ID NO.: 16)
Primer 7:    5'-TATTCTAGAGCGGATCTTCTTCACCAGCTC-3'

(SEQ ID NO.: 17)
Primer 8:    5'-TATAAGCTTCGCCACATCGCCGAATGGAAC-3'
```

The primer sequence for the left arm DNA fragment of the PCR clone lmbV gene is as follows:

```
                                                   (SEQ ID NO.: 18)
Primer 9:    5'-TATGAATTCGACGACGCTGACGTAGTGCAGG-3'

(SEQ ID NO.: 19)
Primer 10:   5'-TATTCTAGACTGACCCGTGAGCAGTTCGTGG-3'
```

The primer sequence for the right arm DNA fragment of the PCR clone lmbV gene is as follows:

```
                                                   (SEQ ID NO.: 20)
Primer 11:   5'-TATTCTAGAGATGTCGTCGTGCACGCATGCC-3'

(SEQ ID NO.: 21)
Primer 12    5'-TATAAGCTTGTCACCGCGGTTGAGCTCGATC-3'
```

The primer sequence for the left arm DNA fragment of the PCR clone mshA gene is as follows:

```
                                                   (SEQ ID NO.: 22)
Primer 13:   5'-TATGAATTCCGGTTCGATCTCCACACCGACCAC-3'

(SEQ ID NO.: 23)
Primer 14:   5'-TATTCTAGACTTGGCCATGGTGTGCATGGCGTG-3'
```

The primer sequence for the right arm DNA fragment of the PCR clone mshA gene is as follows:

```
                                                   (SEQ ID NO.: 24)
Primer 15:   5'-TATTCTAGACAGACCGGTTTCCTCGTACGAGGG-3'
```

-continued

```
                                             (SEQ ID NO.: 25)
Primer 16:   5'-TATAAGCTTCATGGTCACCCGGCAGGAAGTCAC-3'
```

The primer sequence for the left arm DNA fragment of the PCR clone lmbC gene is as follows:

```
                                             (SEQ ID NO.: 26)
Primer 17:   5'-TATGAATTCGGATGTACCGTTTCCTGGACC-3'

(SEQ ID NO.: 27)
Primer 18:   5'-TATTCTAGAGGAGGTGGAGAACGCTGTACG-3'
```

The primer sequence for the right arm DNA fragment of the PCR clone lmbC gene is as follows:

```
                                             (SEQ ID NO.: 28)
Primer 19:   5'-TATTCTAGAGGAGGTGGAGAACGCTGTACG-3'

(SEQ ID NO.: 29)
Primer 20:   5'-TATAAGCTTCAGTCACGTGACCCAAGTACCG-3'
```

The primer sequence for the left arm DNA fragment of the PCR clone lmbD gene is as follows:

```
                                             (SEQ ID NO.: 30)
Primer 21:   5'-TATGAATTCCCTGATGCTCCTGTACACCAGC-3'

(SEQ ID NO.: 31)
Primer 22:   5'-TATTCTAGAGTCCTCCAGGAACAGCAGACTG-3'
```

The primer sequence for the right arm DNA fragment of the PCR clone lmbD gene is as follows:

```
                                             (SEQ ID NO.: 32)
Primer 23:   5'-TATTCTAGACGGTATCTGTTCCTGGGCCTGG-3'

(SEQ ID NO.: 33)
Primer 24:   5'-TATAAGCTTGAACGGTACGTGCAACTCCTCG-3'
```

PCR Amplification

The PCR amplification was performed by using the total DNA of Lincomycin producing strain, *Streptomycin lincolnensis* NRRL ISP-5355 as the template, and using the above left and right arm DNA fragments specific primers of lincE, lmbE3457, lmbV, mshA, and lmbC, to amplify the upstream and downstream sequence, the left and right arm DNA amplified fragments.

Construction of Recombinant Shuttle Plasmid

The left and right arm fragments of each gene were separated by gel electrophoresis, and the gel was recovered and purified. The left arm fragments were digested with EcoRI and XbaI, and the downstream fragments were digested with XbaI and HindIII. After the fragments were collected, they were together inserted into pKC1139 plasmid which was treated with restriction enzymes HindIII and EcoRI (a temperature-sensitive *E. coli-Streptomyces* shuttle plasmids, see: U.S. Pat. No. 5,955,319), thus forming recombinant plasmid shuttle plasmids of each gene.

The recombinant plasmid was transformed into the conventional *E. coli* DH5a, and a monoclonal colony was picked into LB culture medium (containing an alabamamycin antibiotic 100 µg/ml) and cultured overnight until the bacteria solution turned to dense. The recombinant plasmid was extracted and verified by enzyme digestion. Commercial sequencing was performed. The results showed that the recombinant shuttle plasmid was constructed correctly.

2. Construction and Screening of in Frame Knockout Mutants

The correct recombinant shuttle plasmid was transformed into the conventional methylation-deleted *E. coli* ET12567 (see U.S. Pat. Nos. 7,326,782 and 7,105,491) and the lmbE, lmbV, mshA, lmbC and lmbD gene knockout plasmid was introduced into the *Streptomycin lincolnensis* NRRL ISP-5355 strain by conjugative transfer. The lmbE3457 knockout plasmid was introduced into the lmbE knockout mutant to construct the lmbE-E3457 double knockout mutant. The amylin-resistant zygote was selected and the zygote was grown at 37° C. to homologously recombine the upstream or downstream fragment of the plasmid gene with the homologous fragment on the chromosome. The zygote grown well at 37° C. were inoculated into TSB liquid medium without any antibiotics (purchased from SIGMA-ALDRICH) and incubated at 30° C. for two days. A small amount of bacteria was taken and inoculated in TSB liquid medium without antibiotics. After 5 to 6 rounds, the bacteria solution was streaked on MS solid medium and single colonies that lost apramycin resistance were picked. DNA was extracted and genotypes were determined by PCR.

In the present example, a mutant strain of the biosynthesis gene cluster of lincomycin was successfully constructed by the above method. The experimental results are shown in FIG. 1.

FIG. 1*a* is the verification result of the lmbE knockout mutant. From the electrophoretogram of Figure a, it can be seen that the lmbE gene in the lmbE knockout mutant was deleted by about 0.55 kb, indicating that the lmbE knockout mutant strain was successfully constructed in this Example.

Figure 1B:
FIG. 1*b*, lmbE-E3457 double knockout mutant.

FIG. 1*b* is the verification result of the lmbE-E3457 double knockout mutant. On the basis of the lmbE knockout mutant, lmbE3457 was further knocked out. From the electropherogram of figure b, it can see that the lmbE3457 gene was deleted by about 0.34 kb in lmbE-E3457 double knockout mutant, indicating that the lmbE-E3457 double knockout mutant was successfully constructed in this example.

Figure 1C:
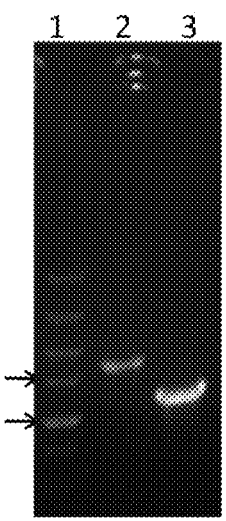
FIG. 1*c*, lmbV knockout mutant.

FIG. 1*c* is the verification result of the lmbV knockout mutant. From the electrophoretogram of Figure c, it can be seen that the lmbV gene in the lmbV knockout mutant was deleted by about 0.4 kb, indicating that the lmbV knockout mutant strain was successfully constructed in this Example.

Figure 1D:
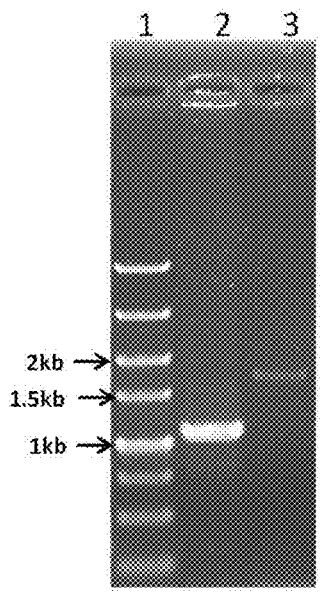
FIG. 1*d*, mshA knockout mutant.

FIG. 1*d* is the verification result of the mshA knockout mutant. From the electrophoretogram of Figure d, it can be seen that the mshA gene in the mshA knockout mutant was deleted by about 0.6 kb, indicating that the mshA knockout mutant strain was successfully constructed in this Example.

Figure 1E:
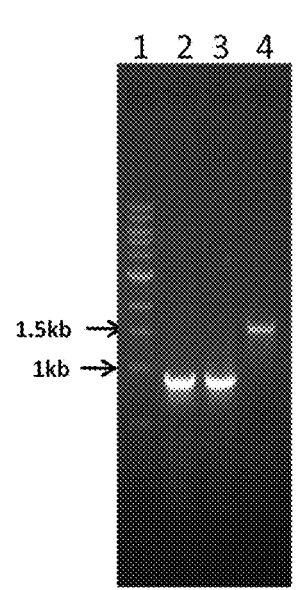
FIG. 1*e*, lmbC knockout mutant.

FIG. 1*e* is the verification result of the lmbC knockout mutant. From the electrophoretogram of Figure e, it can be seen that the lmbC gene in the lmbC knockout mutant was deleted by about 0.7 kb, indicating that the lmbC knockout mutant strain was successfully constructed in this Example.

Figure 1F:
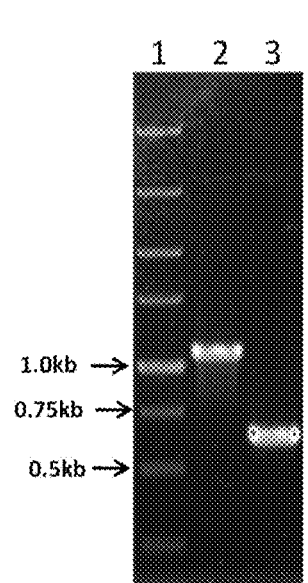
FIG. 1*f*, lmbD knockout mutant.

FIG. 1*f* is the verification result of the lmbD knockout mutant. From the electrophoretogram of Figure f, it can be seen that the lmbD gene in the lmbD knockout mutant was deleted by about 0.4 kb, indicating that the lmbD knockout mutant strain was successfully constructed in this Example.

Figure 1G:
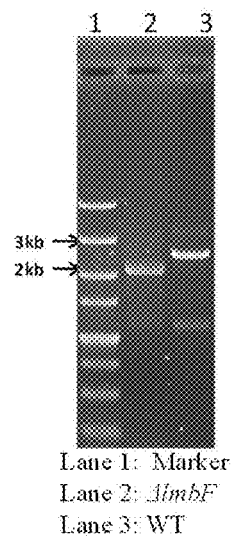
FIG. 1*g*, lmbF knockout mutant.

FIG. 1*g* is the verification result of the lmbF knockout mutant. From the electrophoretogram of Figure g, it can be seen that the lmbF gene in the lmbF knockout mutant was deleted by about 0.5 kb, indicating that the lmbF knockout mutant strain was successfully constructed in this Example.

Example 2 Fermentation of Recombinant Strains

1. Seed Activation and Culture

Spores of recombinant strain preserved at −80° C. were spread on MS medium (mannitol 2%, soybean meal 2%, agar 2%) and cultured at 30° C. for 7 days. Approximately 1 cm² of agar block containing spores and hyphae was cut out and inoculated into the primary fermentation medium (Soluble starch 20.0 g, Soy flour 10.0 g, Corn steep liquor 30.0 g, Glucose 10.0 g, $(NH_4)_2SO_4$ 1.5 g, $CaCO_3$ 5.0 g, pH=7.0), cultured at 30° C. 250 rpm for 40 hours to obtain a seed culture solution for the next experiment.

2. Enlarge Cultivation

The seed culture solution was inoculated into the fermentation medium at a seeding volume of 10% by volume (Glucose 100.0 g, Soy flour 25.0 g, Corn steep liquor 2.0 g, $NaNO_3$ 8.0 g, NaCl 5.0 g, $(NH_4)_2SO_4$ 8.0 g, $K_2HPO_4$ 0.2 g, $CaCO_3$ 8.0 g, pH=7.0), cultured at 30° C., 250 rpm for 7 days, and the fermentation broth was harvested to obtain a crude product containing a structural analog of lincomycin, which was stored at low temperatures for detection and isolation of purified compounds.

Example 3 Detection of Fermentation Products 1 mL of fermentation broth was filtered and centrifuged at 12,000 r/min for 10 min. 300 μL of fermentation broth was pipetted and three-fold diluted with 600 μL mobile phase (5 mM ammonium acetate:methanol=40:60). The sample was fully vortex shaken with vortex, and allowed to stand for 24 h at 4° C., centrifuged at 12,000 r/min for 10 min, 50 and a small amount of supernatant was taken for HPLC and LC-MS detection and analysis. The detection conditions were as follows: Agilent ZORBAX SB-C18 (5 μm 4.6×250 mm) was used as column; 210 nm detection wavelength; the mobile phase was 5 mM ammonium acetate solution:methanol (40:60); constant gradient elution for 17 min; the flow rate was 0.6 mL/min; and the injection volume was 20 μL.

Figure 2:
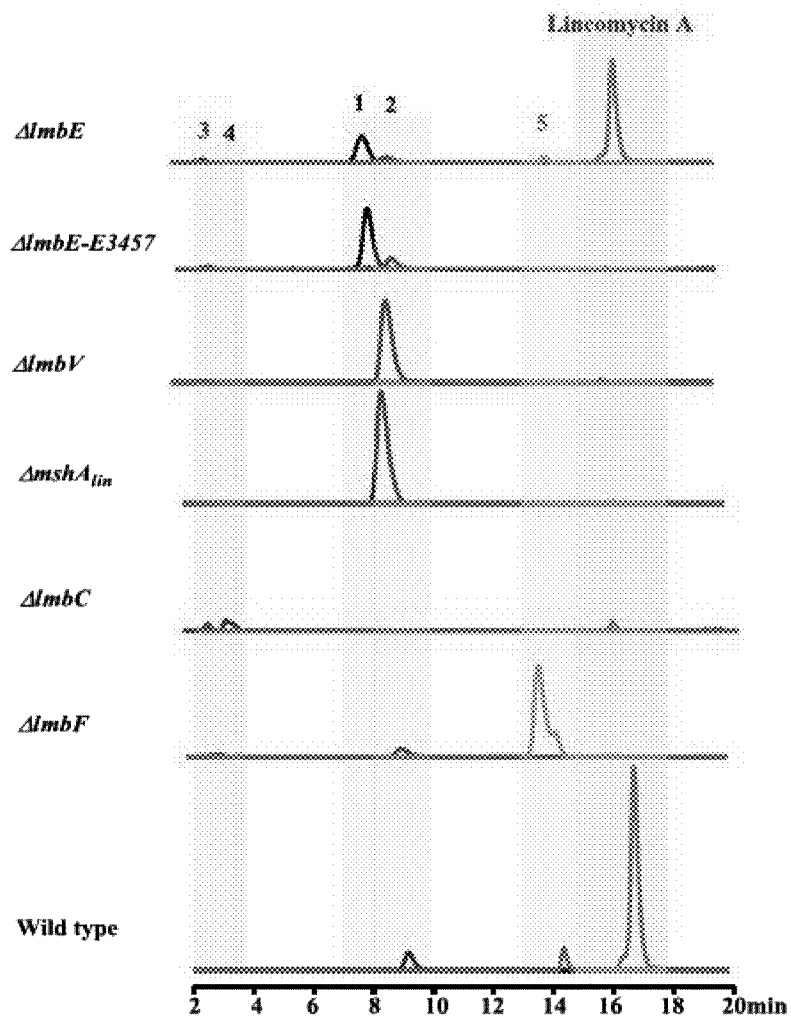
FIG. 2 shows the results of HPLC-MS detection of the fermentation broth of the in frame knockout mutant of a lincomycin-producing strain, showing the production of lincomycin A and compounds 1-5 in each mutant.

The test results are shown in FIG. 2. It can be seen from the figure that compared with the wild type, the content of compound 1 in the fermentation product of the lmbE knockout mutant and the lmbE-E3457 double knockout mutant has significantly increased; The content of compound 2 in the fermentation product of the lmbV knockout mutant and the mshA knockout mutant has significantly increased; the content of compound 5 in the fermentation product of the lmbF knockout mutant has significantly increased; and the content of the compound 3, 4 in the fermentation product of the lmbC knockout mutant has increased. While the wild-type strain did not produce or produced only a trace amount of the above compounds.

Example 4 Isolation and Purification of Lincomycin Structural Analogs

The fermentation broth was centrifuged at 4000 rpm for 20 minutes and the supernatant was taken. Firstly, the macroporous resin XAD-2 was used to adsorb the fermentation broth of the mutant and eluted with methanol; then, the eluate was concentrated and separated on a Sephadex LH20 gel column, and the target compound-enriched tube was determined by TLC/LC-MS analysis; The C18 semi-preparative column was used for crude separation to obtain relatively pure compounds. Finally, the compounds were further purified by Sephadex G10 gel column to obtain each target compound, and the structure of each target compound was identified.

Figure 3A:
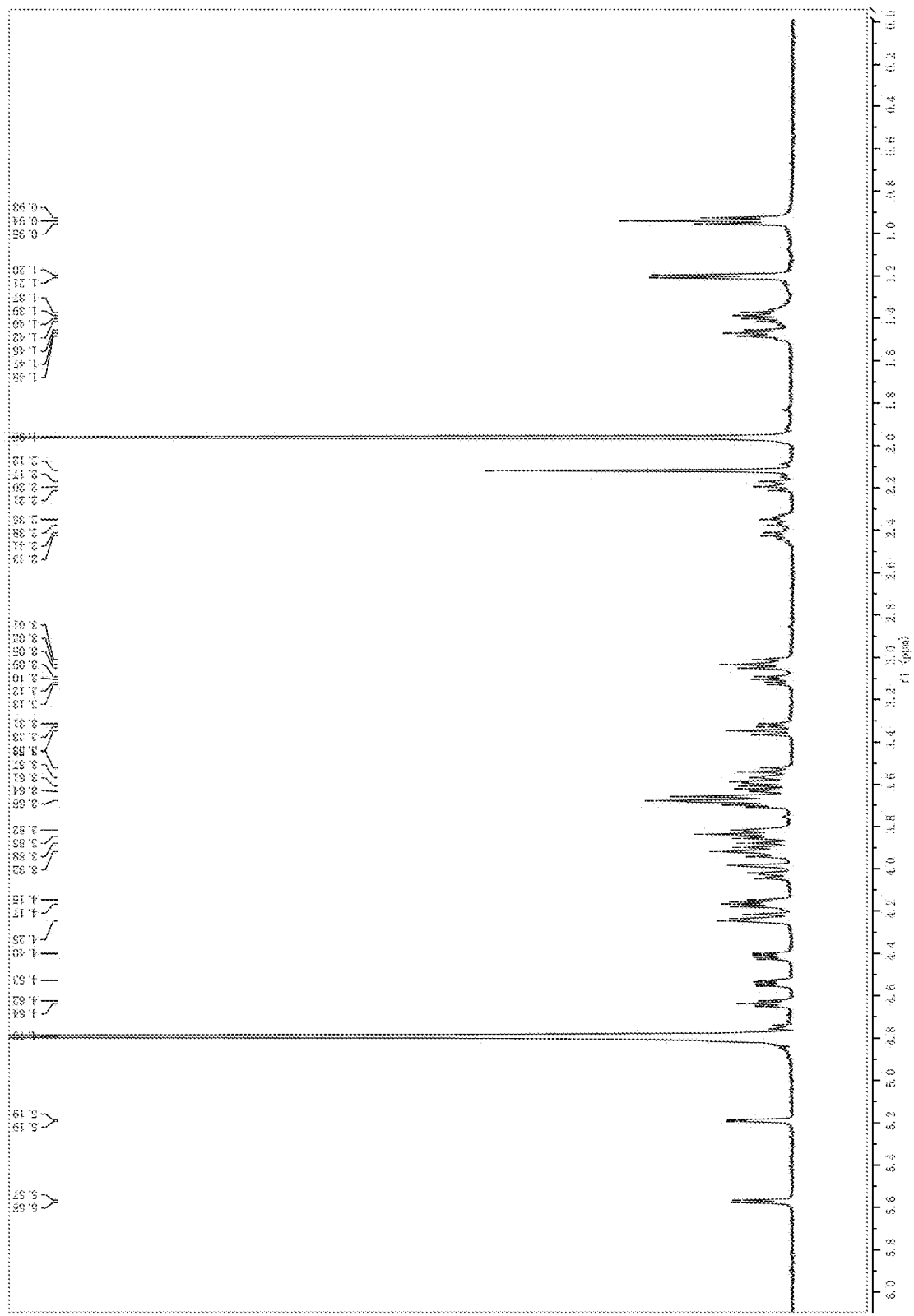
Figure 3C:
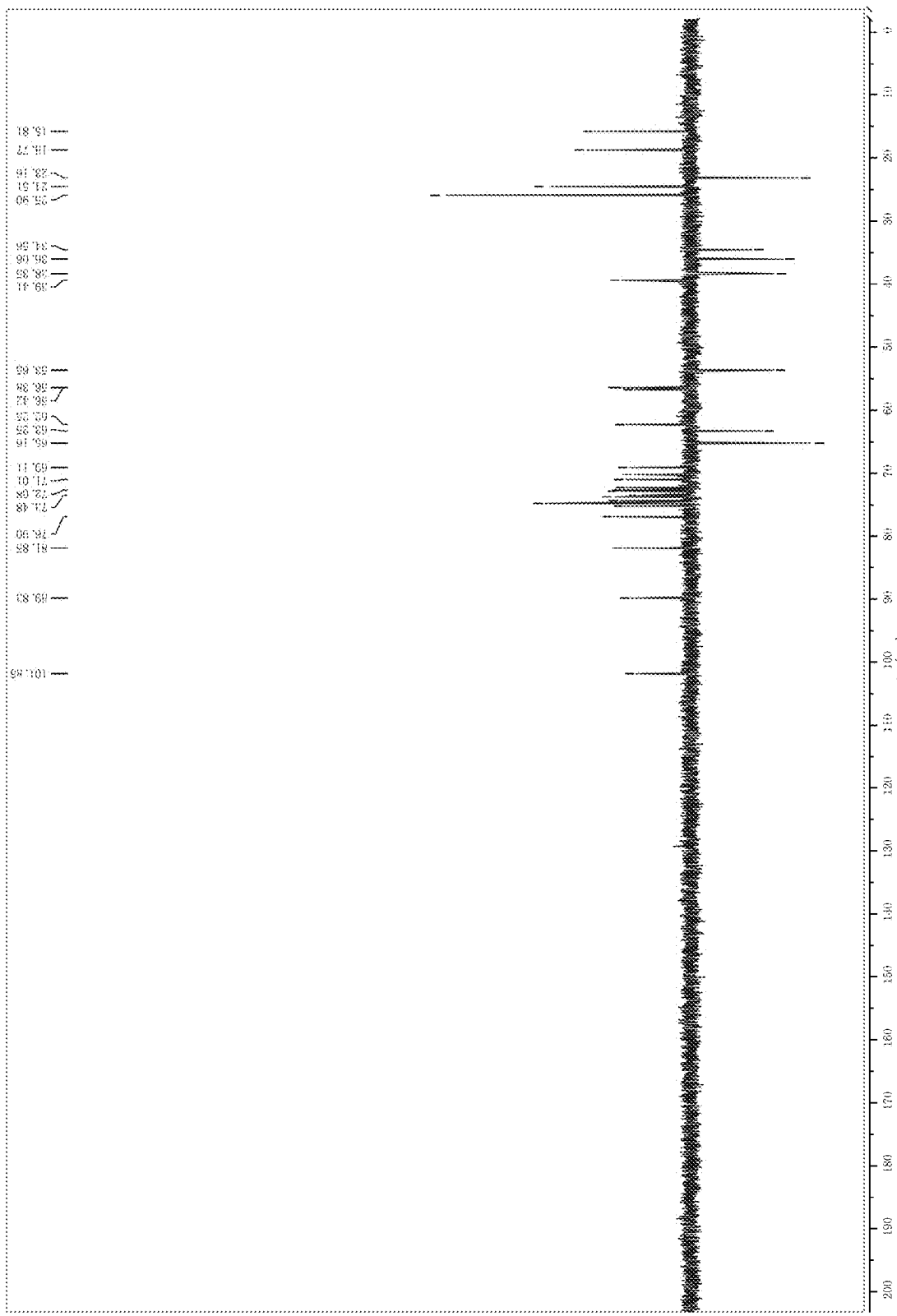
FIG. 3*c*, DEPT135 NMR spectrum.
Figure 3D:
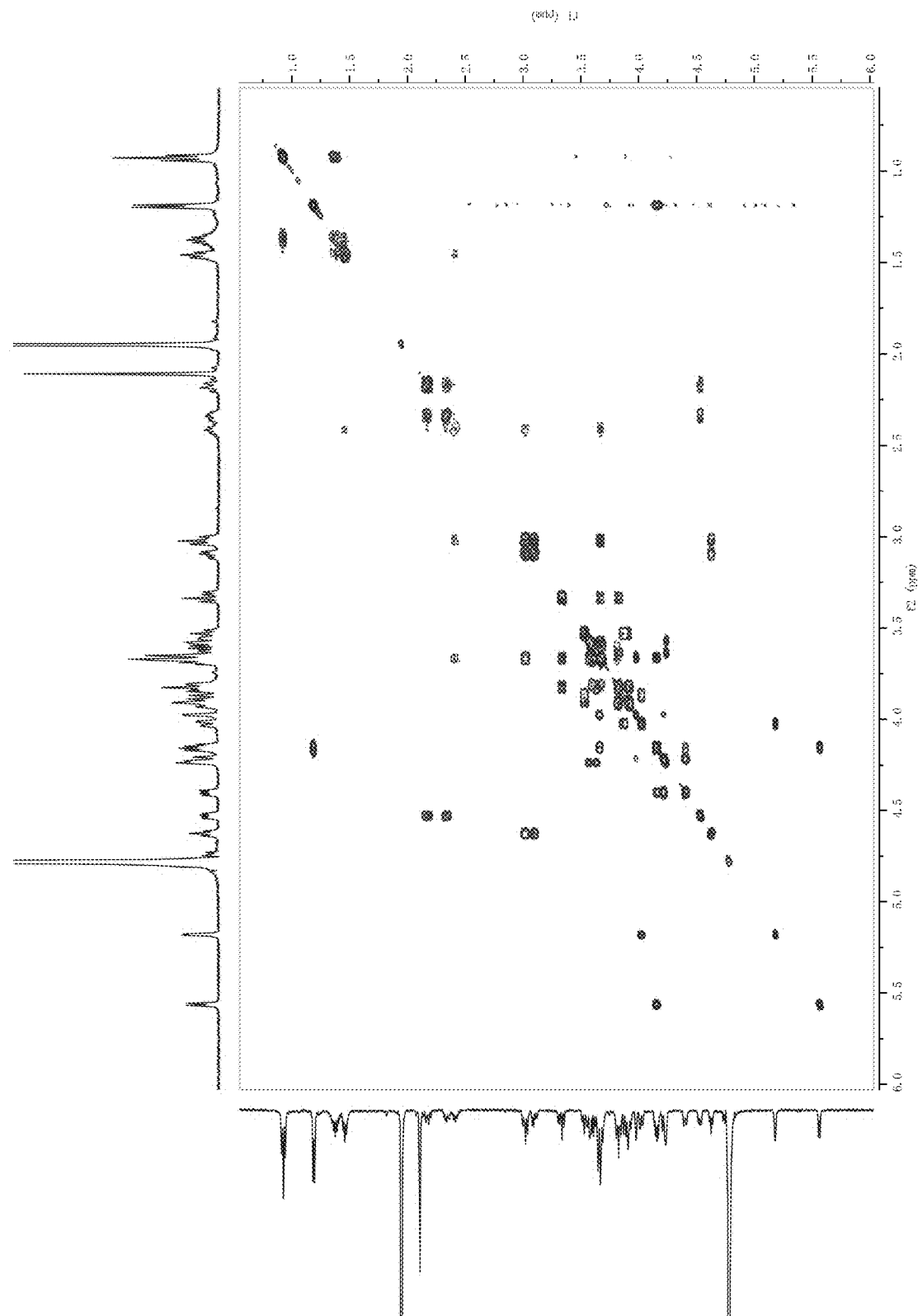
FIG. 3*d*, COSY NMR spectrum.
Figure 3E:
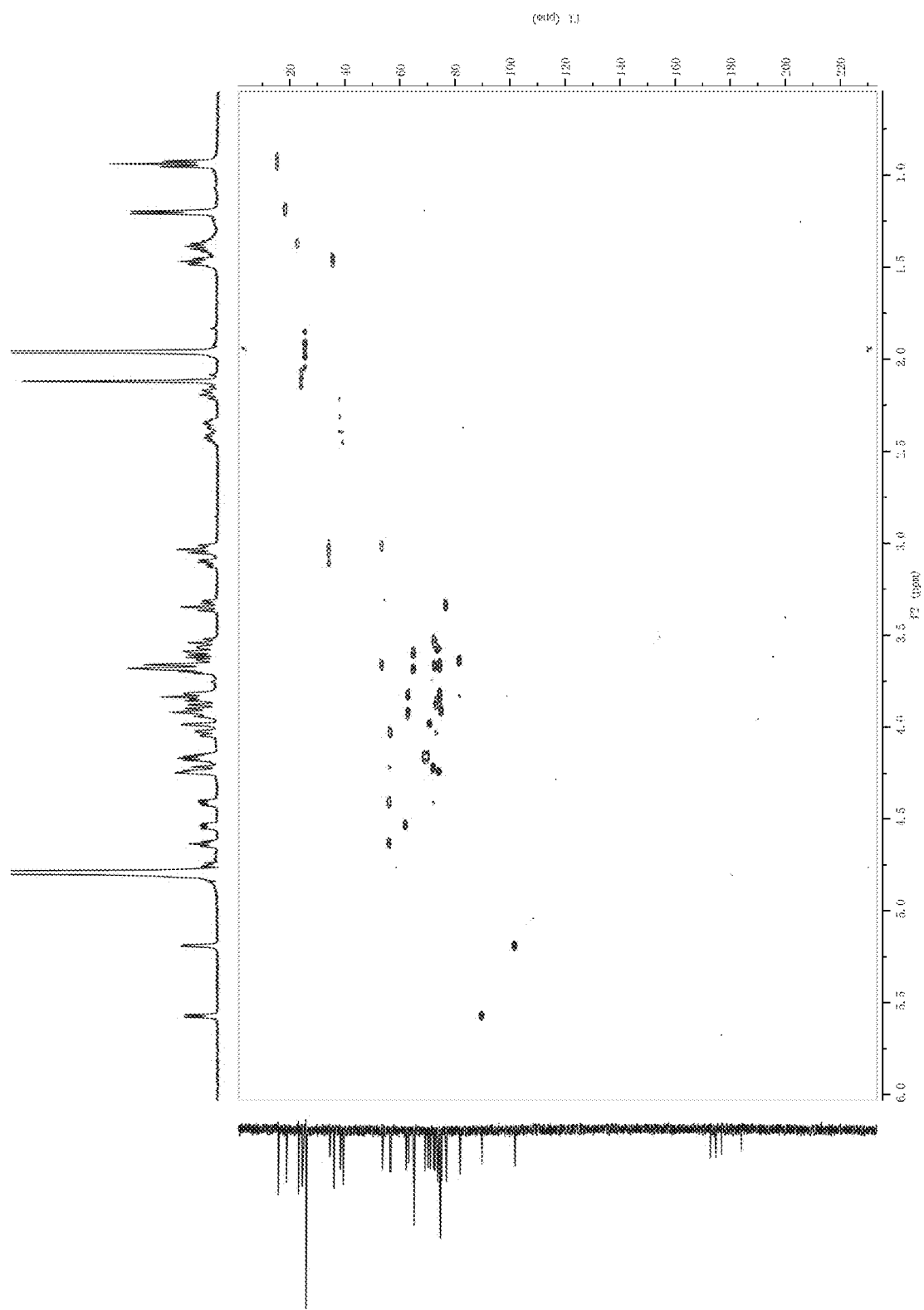
FIG. 3*e*, HSQC NMR spectrum.
Figure 3F:
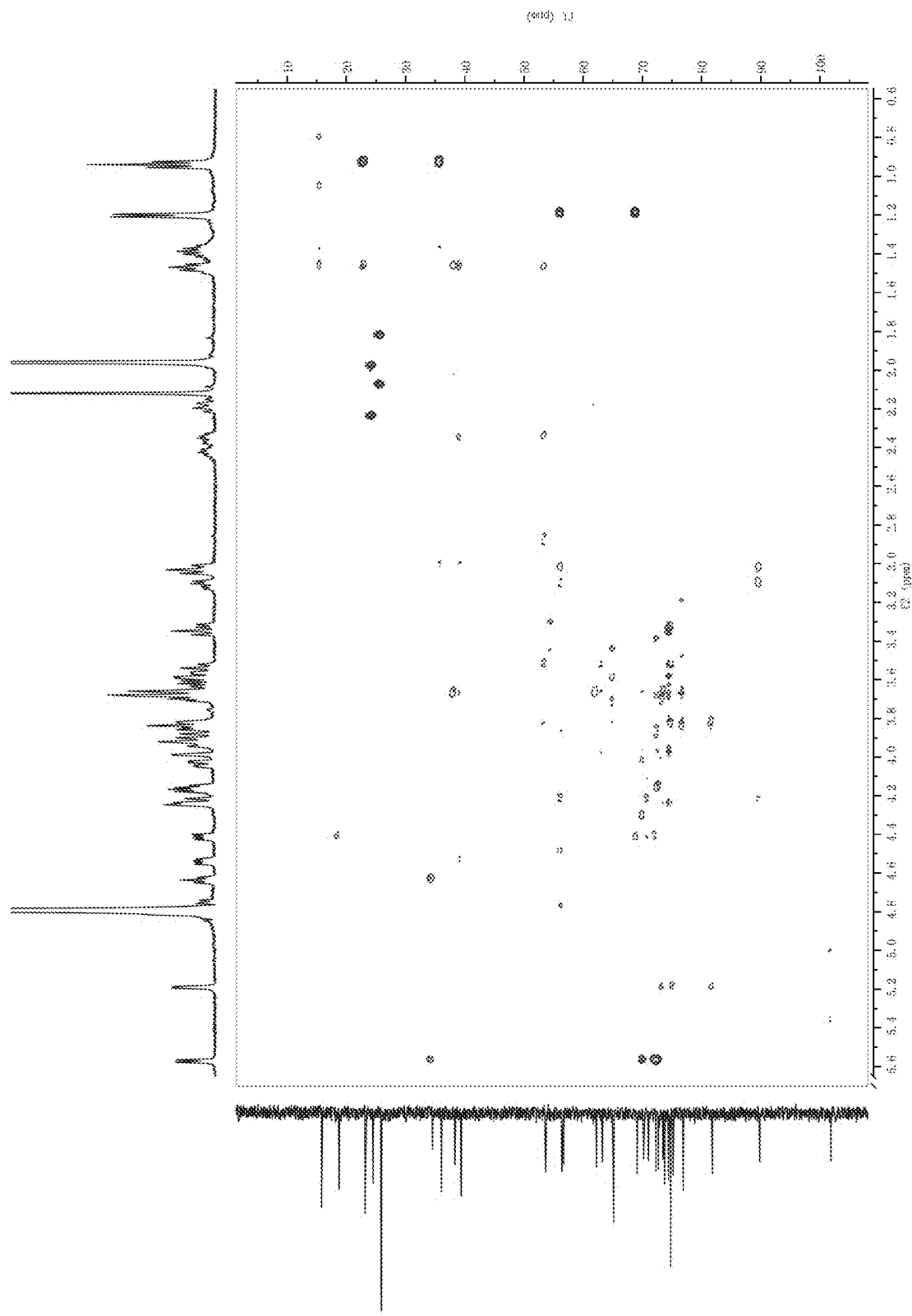
FIG. 3*f*, HMBC NMR spectrum.
Figure 3G:
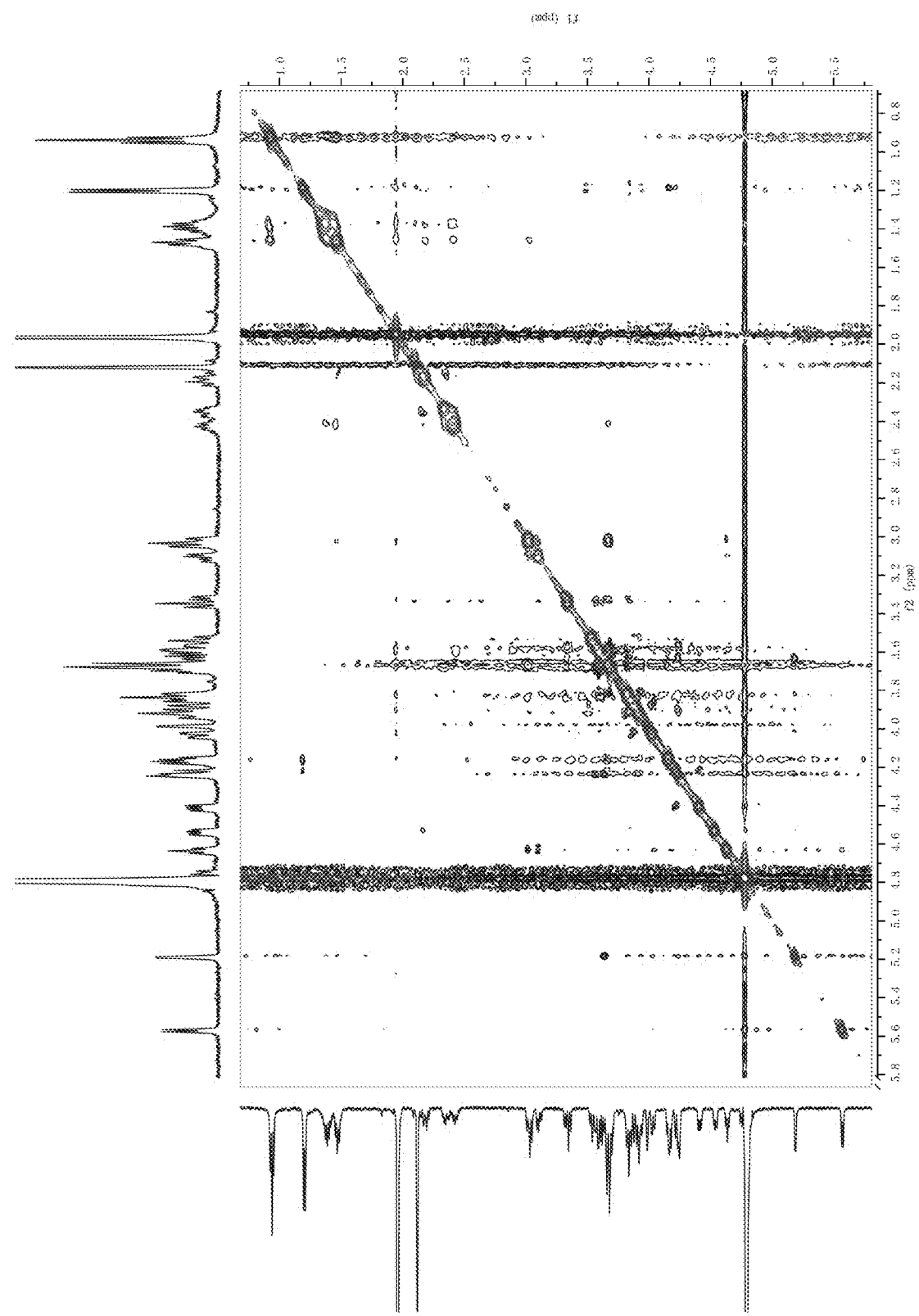
FIG. 3*g*, NOESY NMR spectrum.

FIG. 3 shows the results of NMR analysis of compound 1, FIG. 3a, 1H NMR spectrum; FIG. 3b, 13C NMR spectrum; FIG. 3c, DEPT135 NMR spectrum; FIG. 3d, COSY NMR spectrum; FIG. 3e, HSQC NMR spectrum; FIG. 3f, HMBC NMR spectrum; FIG. 3g, NOESY NMR spectrum. The structure of Compound 1 was identified based on the above spectra as shown in Formula I1.

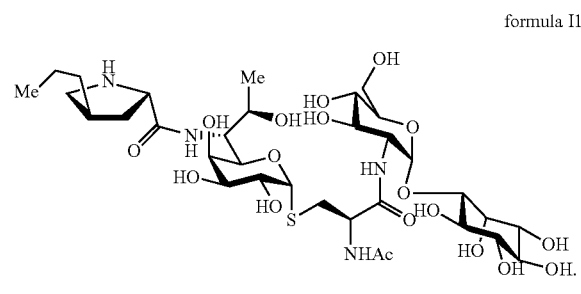

formula I1

Figure 4A:
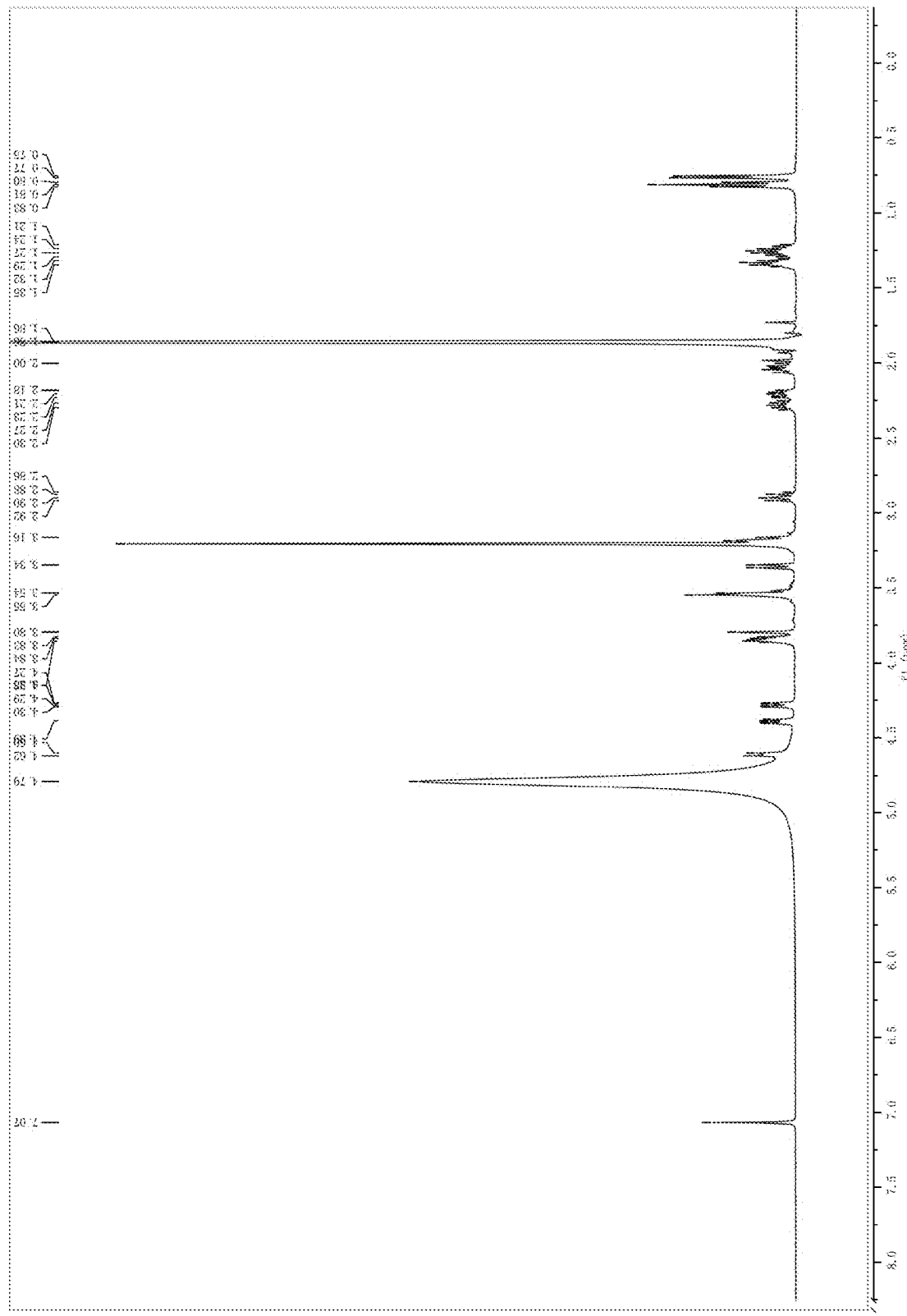
Figure 4D:
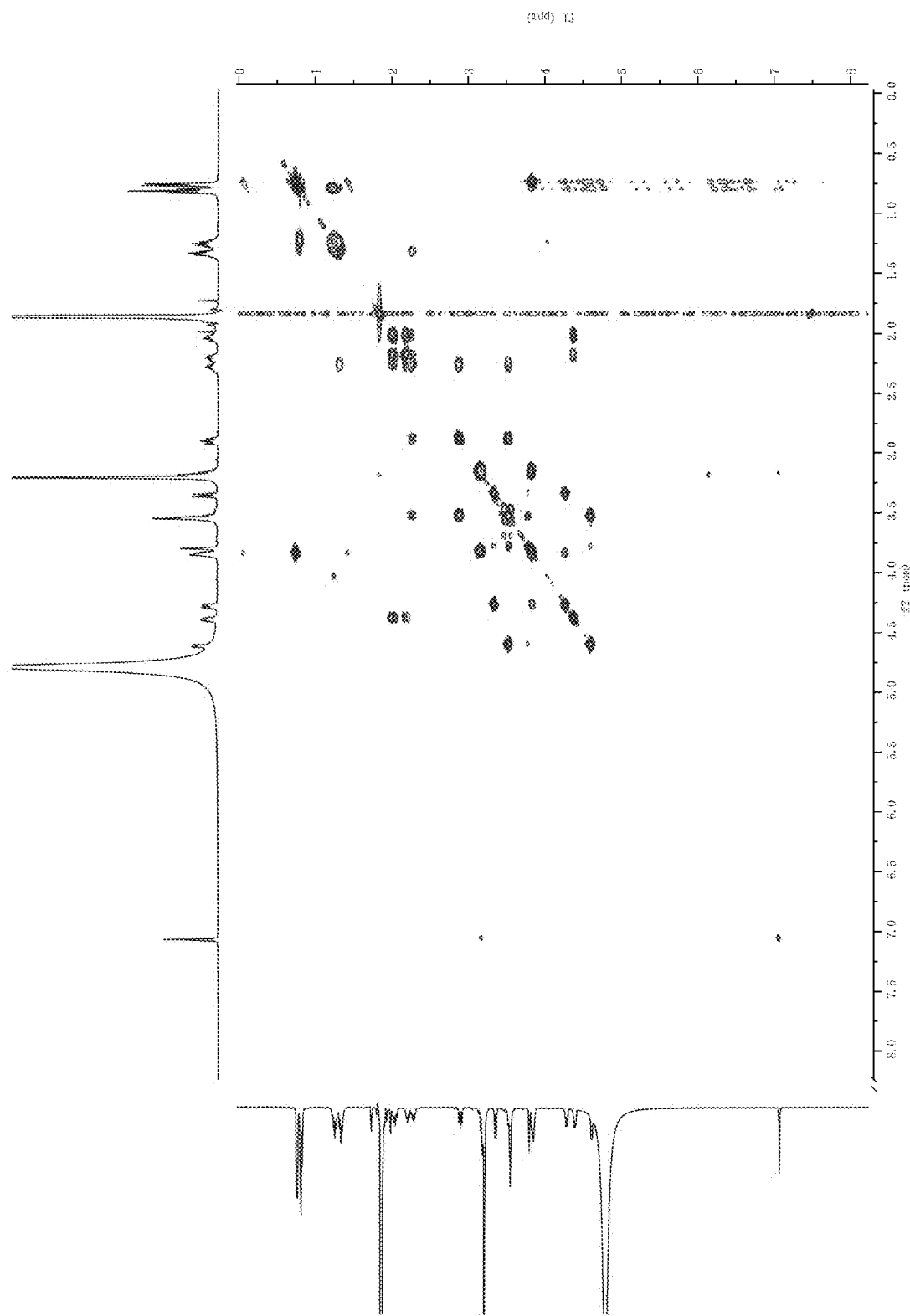
FIG. 4*d*, COSY NMR spectrum.
Figure 4E:
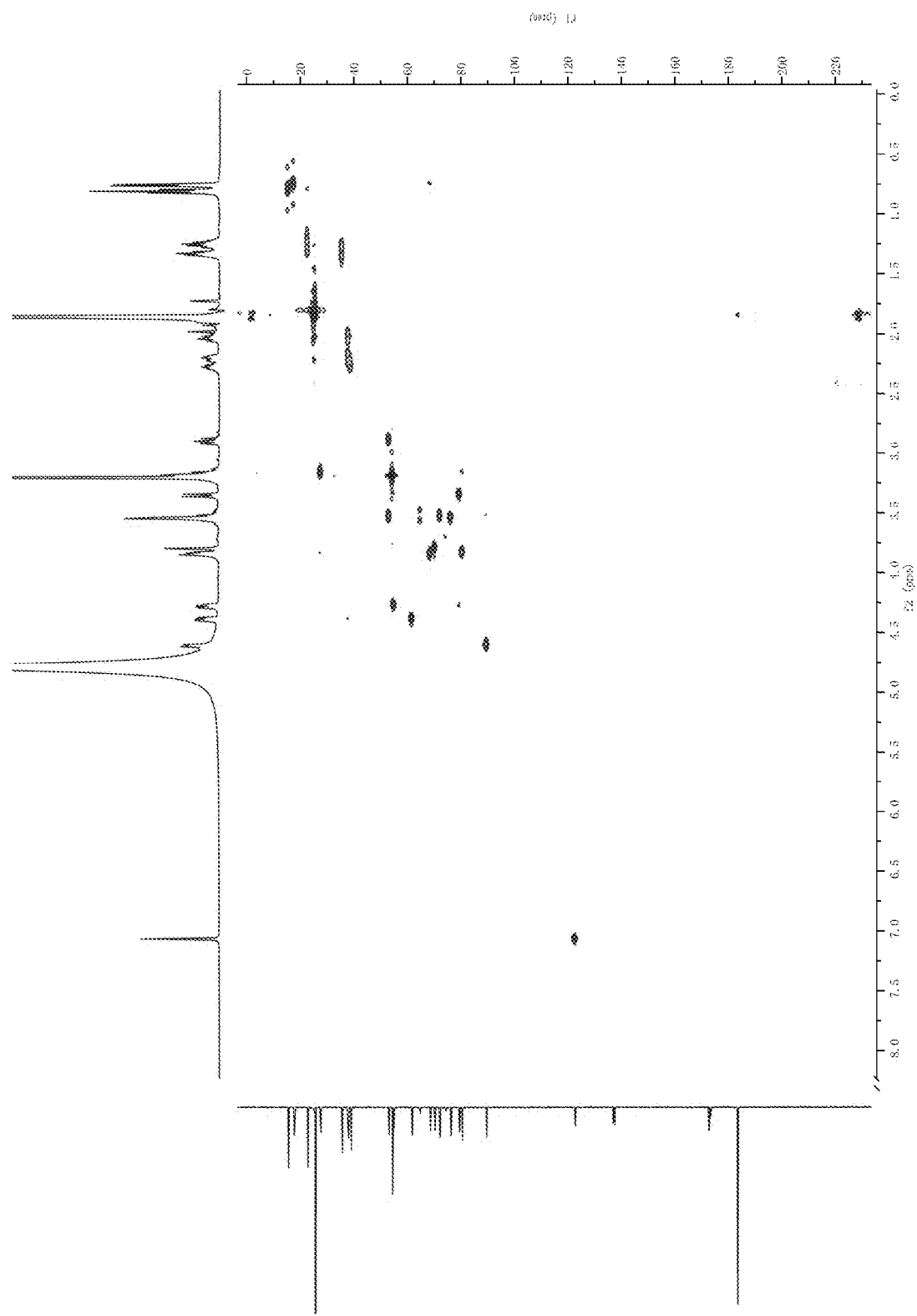
FIG. 4*e*, HSQC NMR spectrum.
Figure 4F:
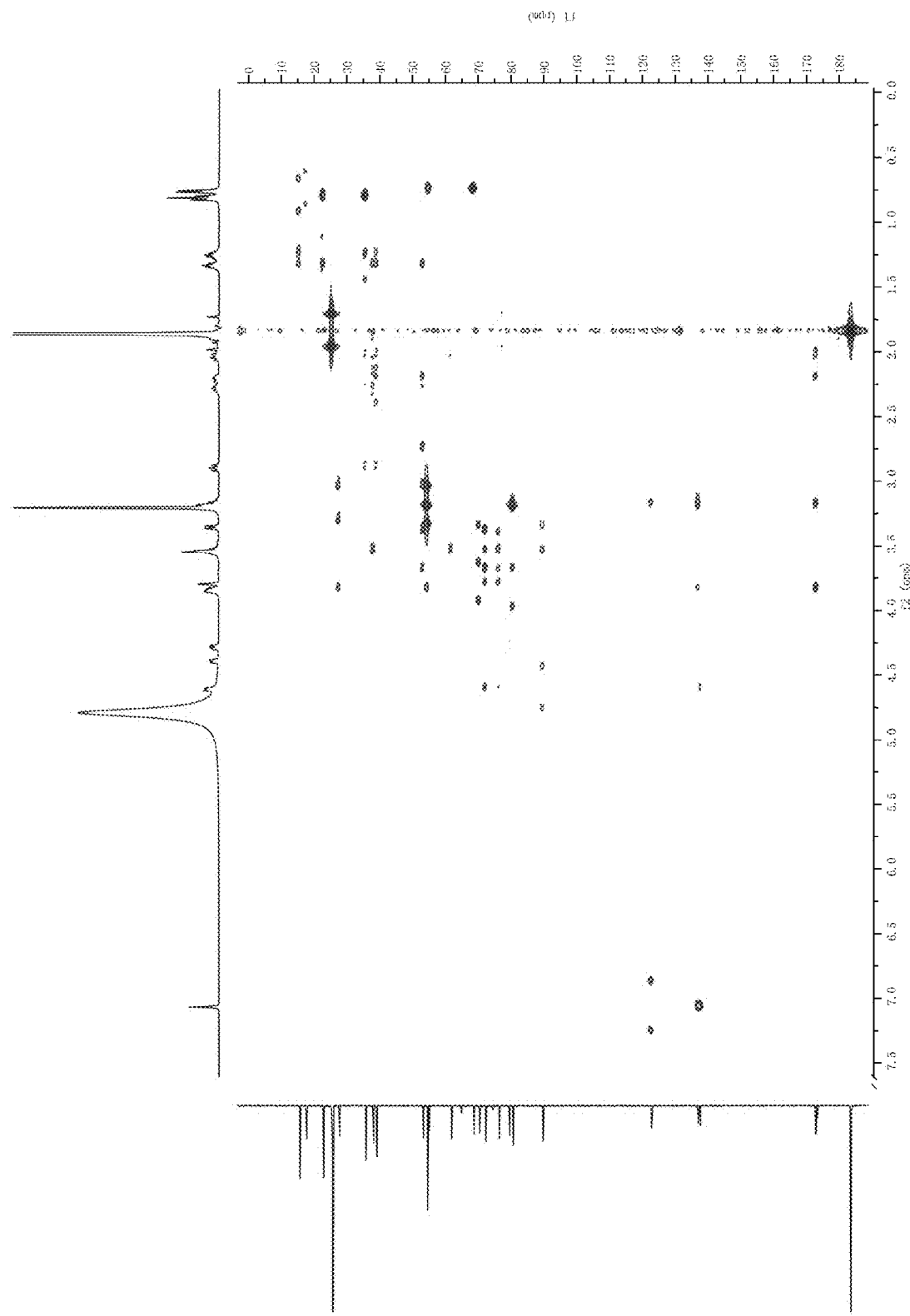
FIG. 4*f*, HMBC NMR spectrum.
Figure 4G:
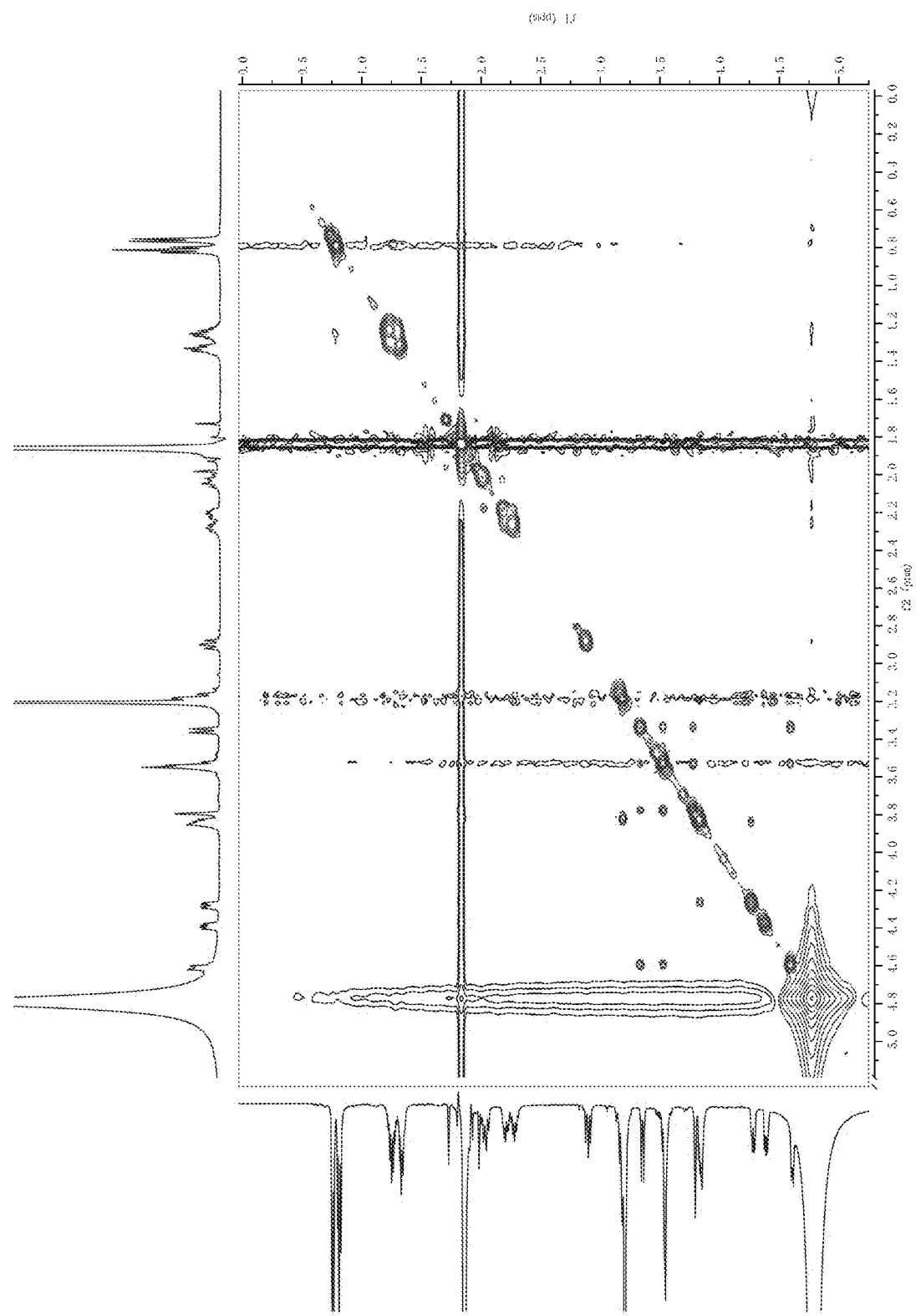
FIG. 4*g*, NOESY NMR spectrum.
Figure 5D:
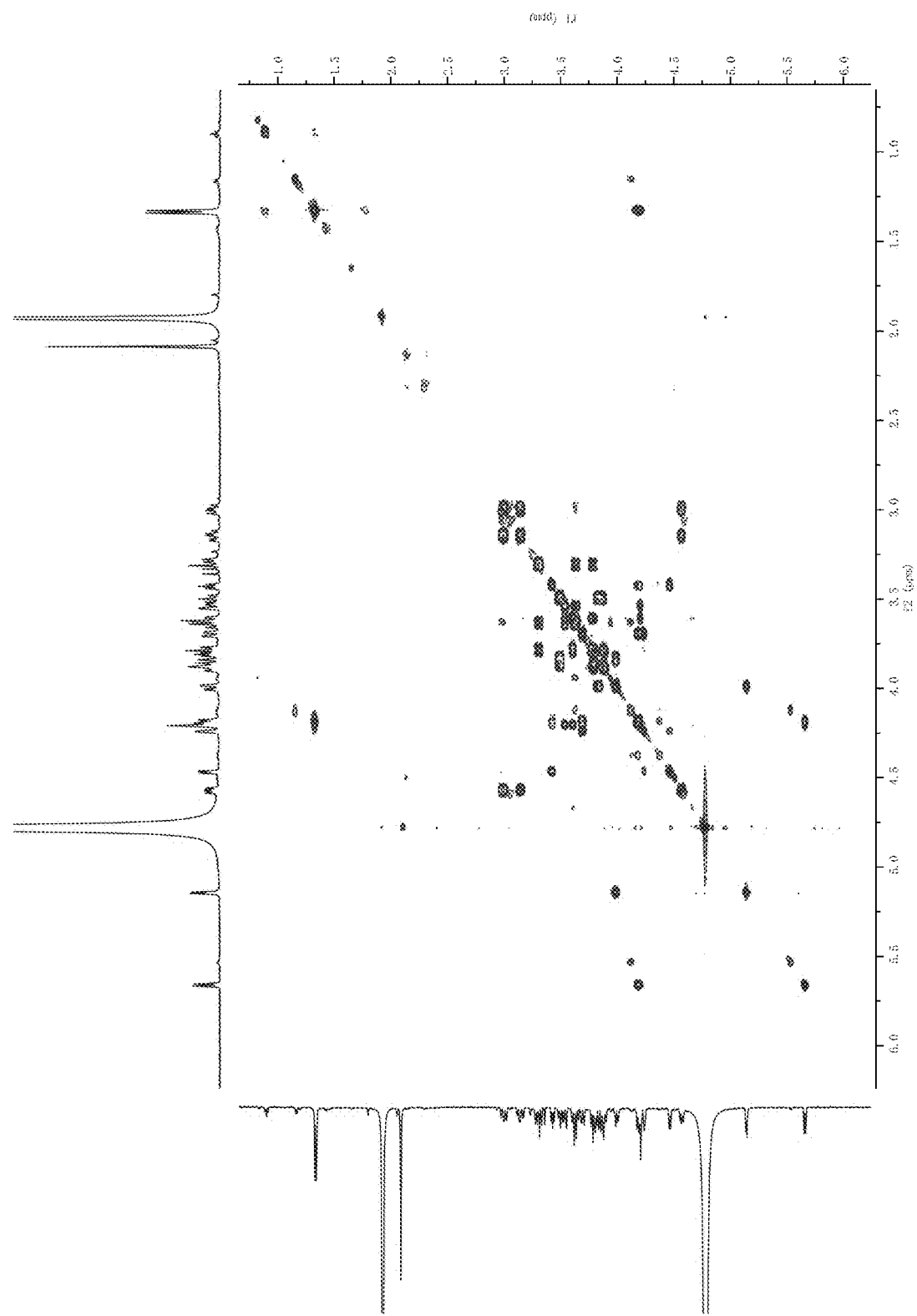
FIG. 5d, COSY NMR spectrum.
Figure 5E:
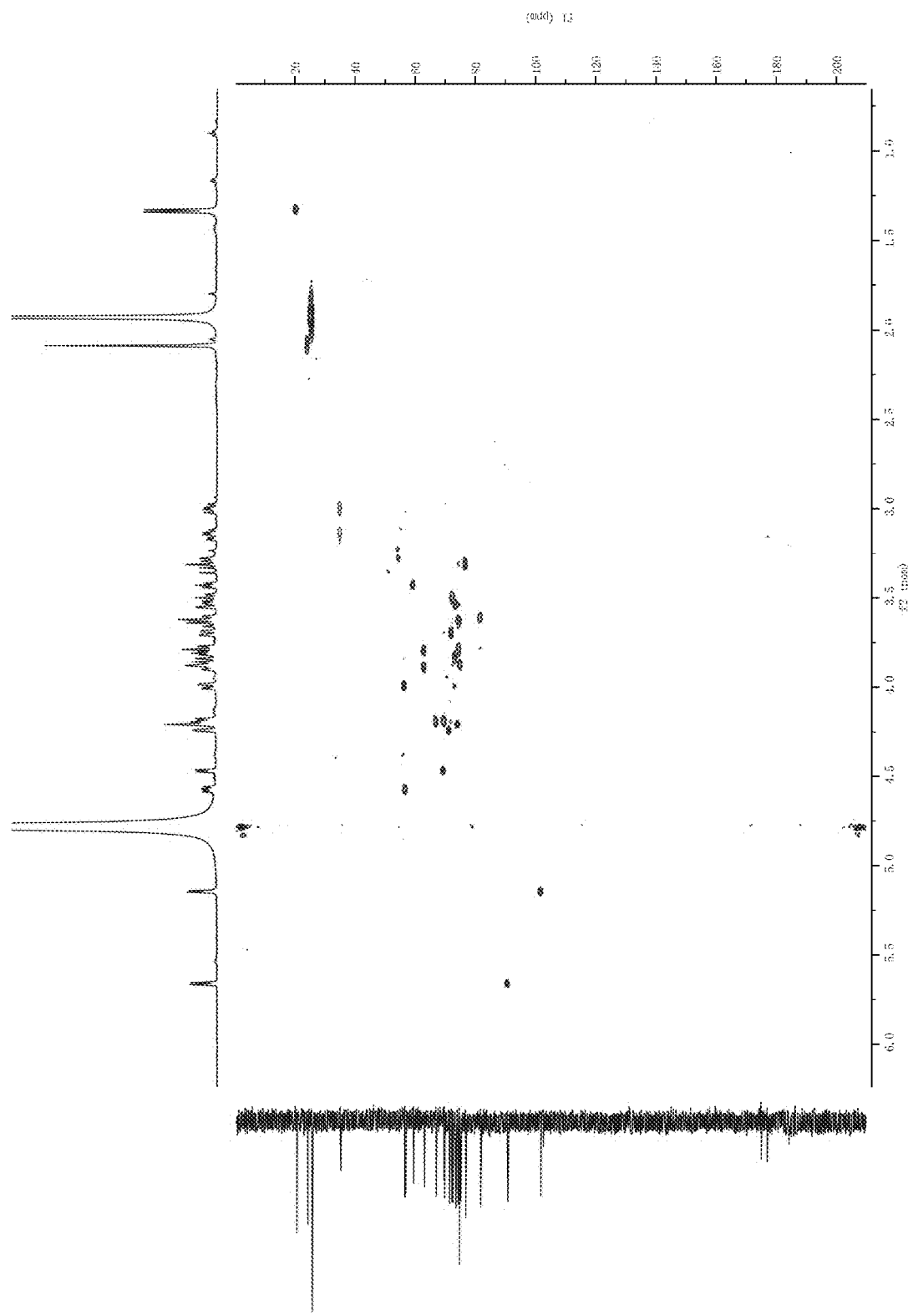
FIG. 5e, HSQC NMR spectrum.
Figure 5F:
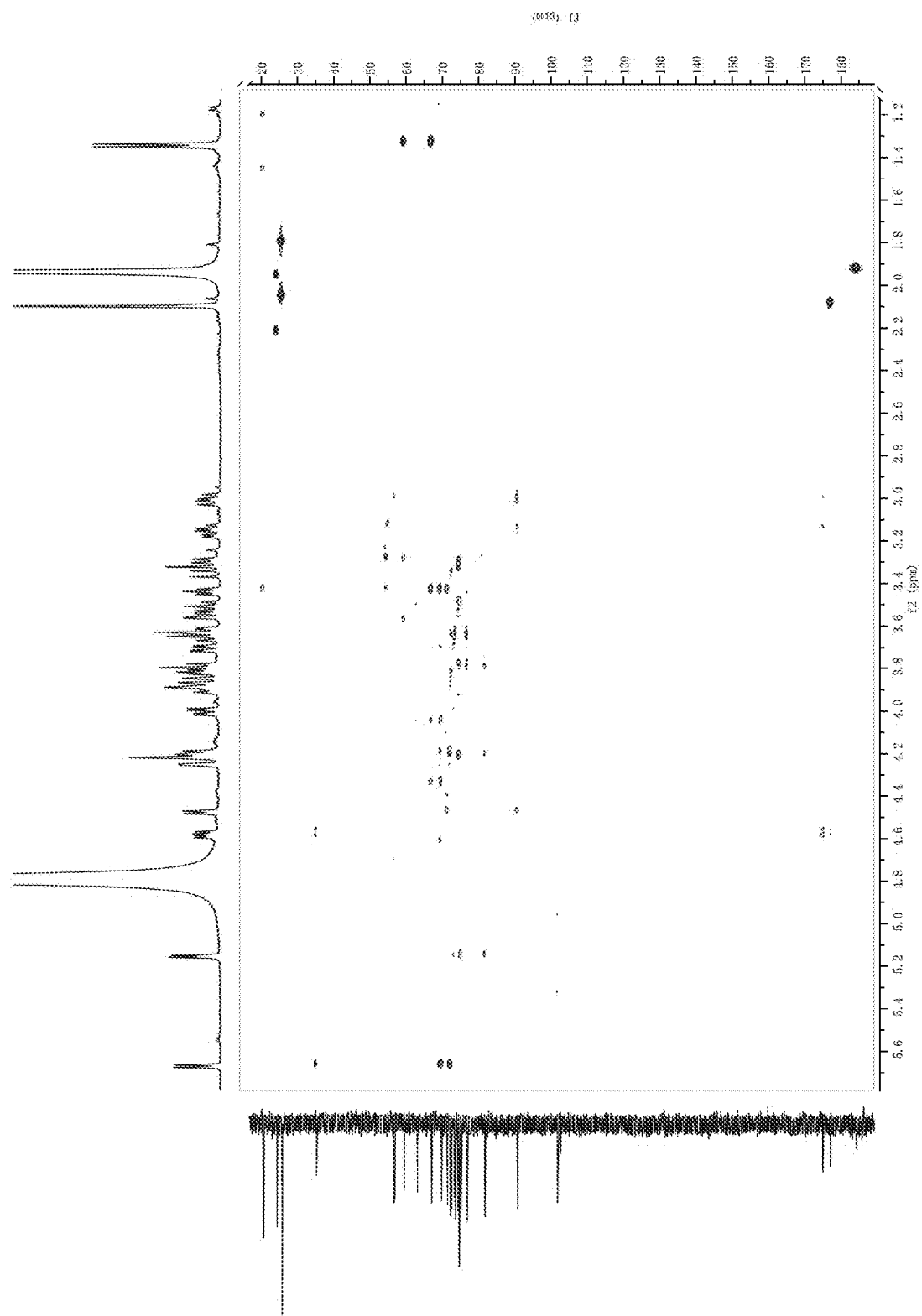
FIG. 5f, HMBC NMR 50 spectrum.
Figure 5G:
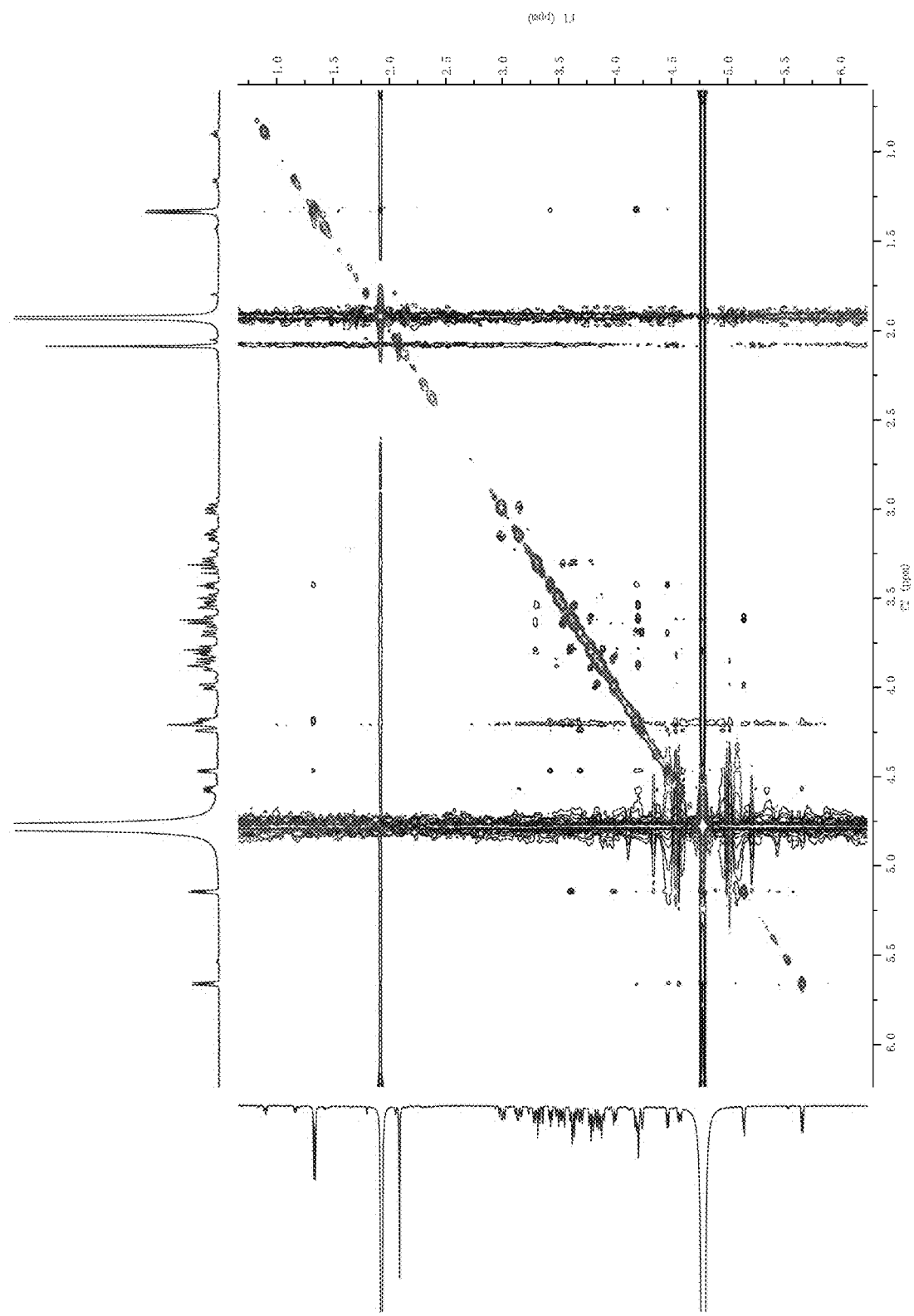
FIG. 5g, NOESY NMR spectrum.
Figure 6A:
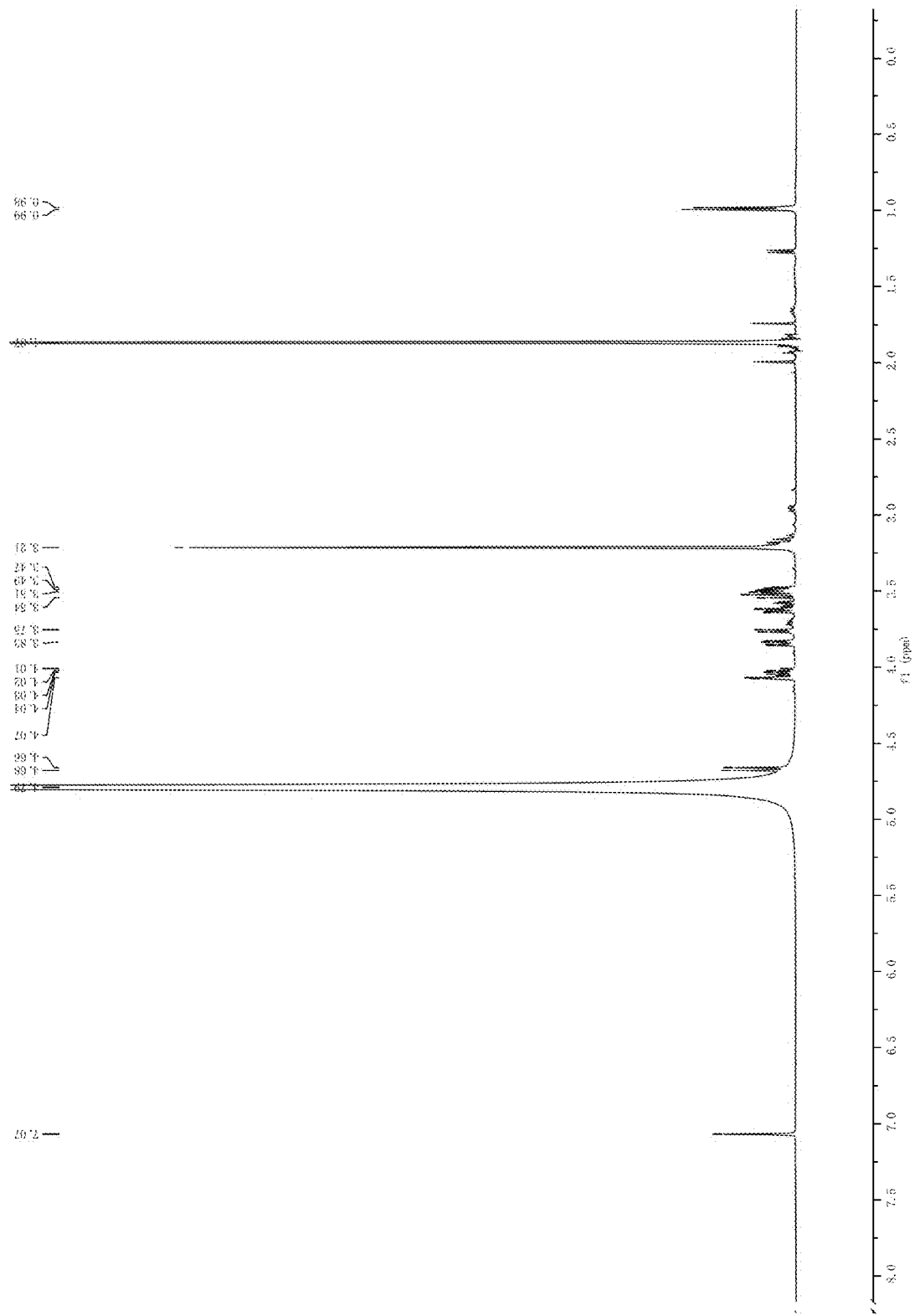
Figure 6E:
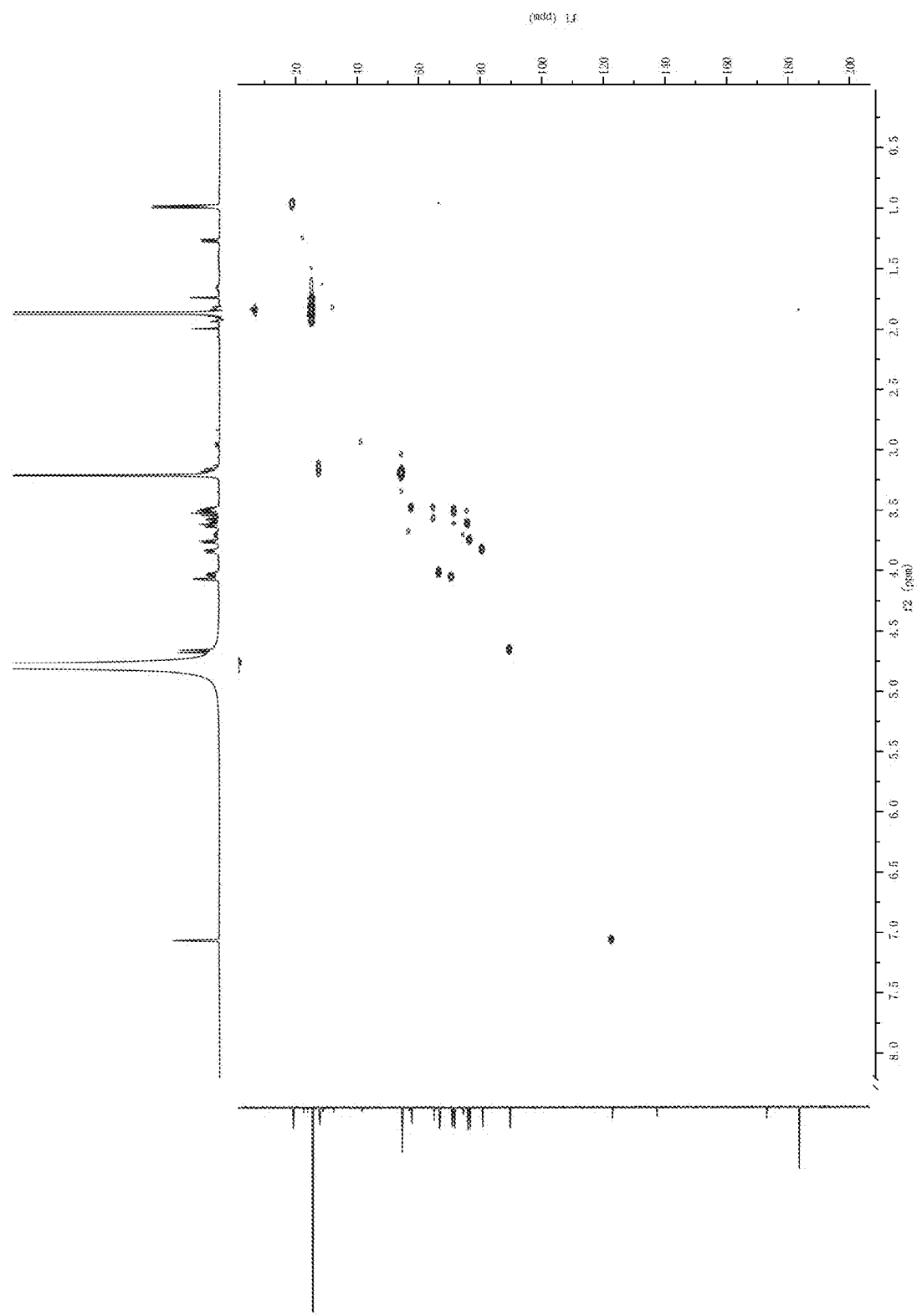
FIG. 6e, HSQC NMR spectrum.
Figure 6F:
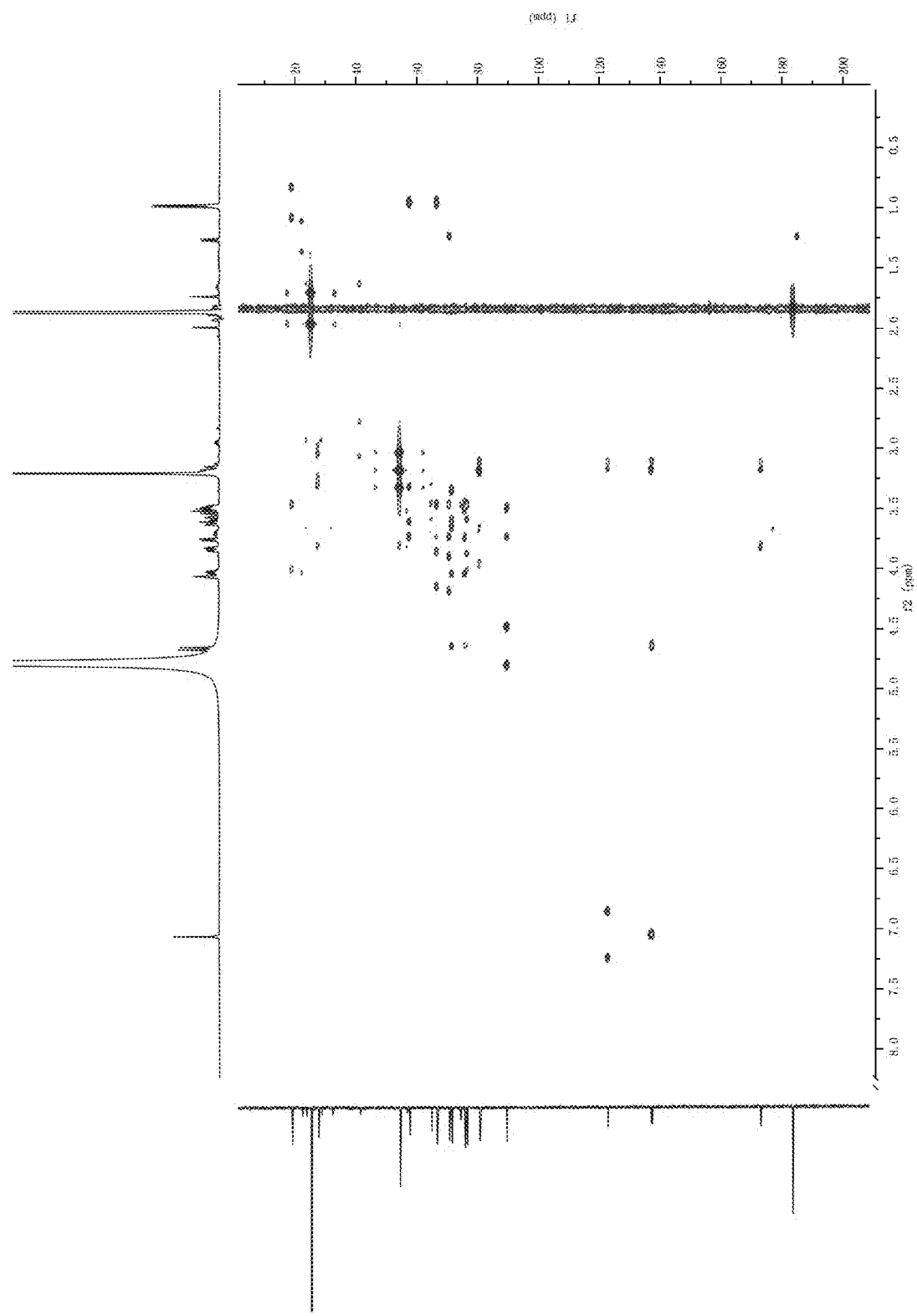
FIG. 6f, HMBC NMR spectrum.
Figure 6G:
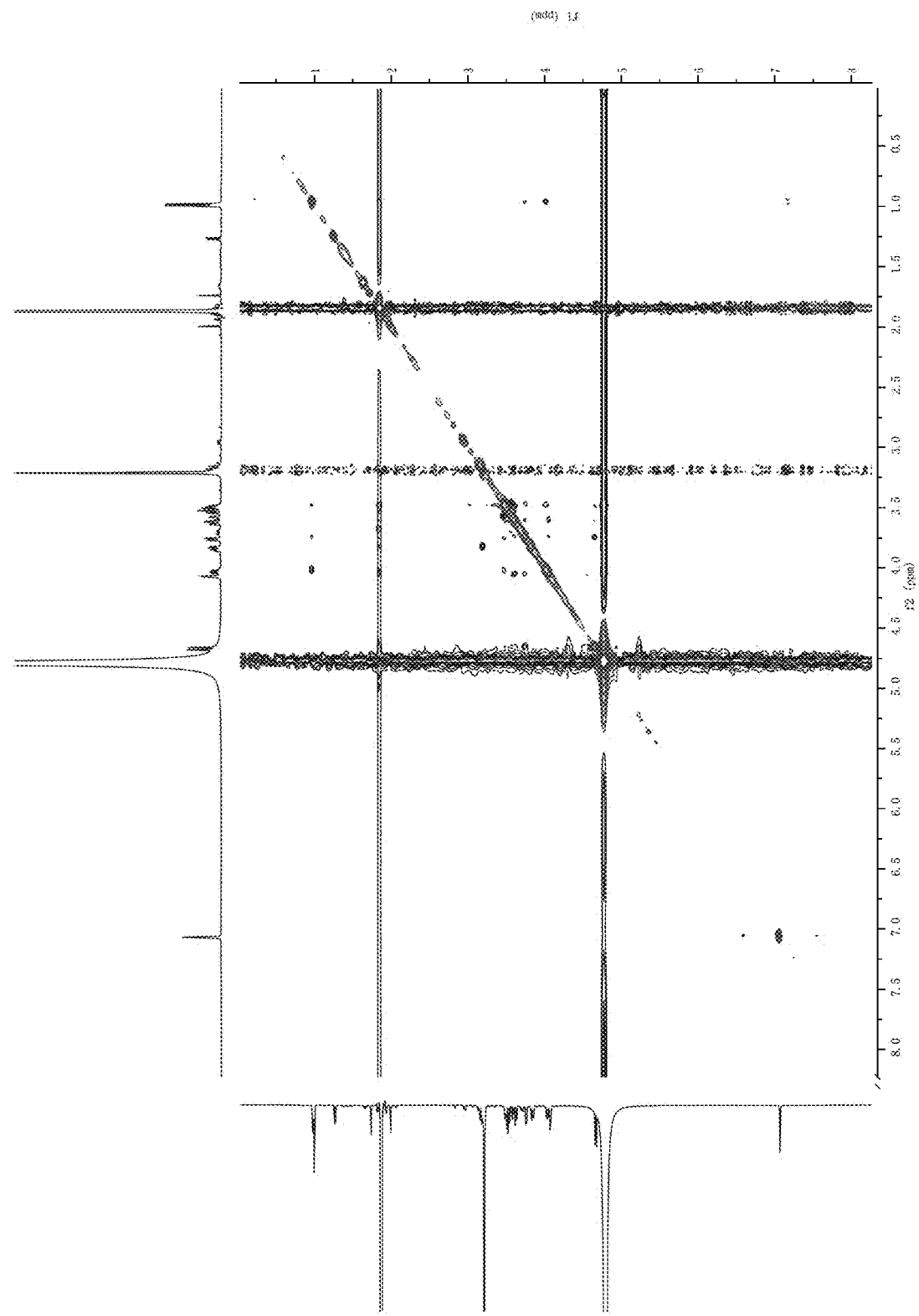
FIG. 6g, NOESY NMR spectrum.
Figure 7A:
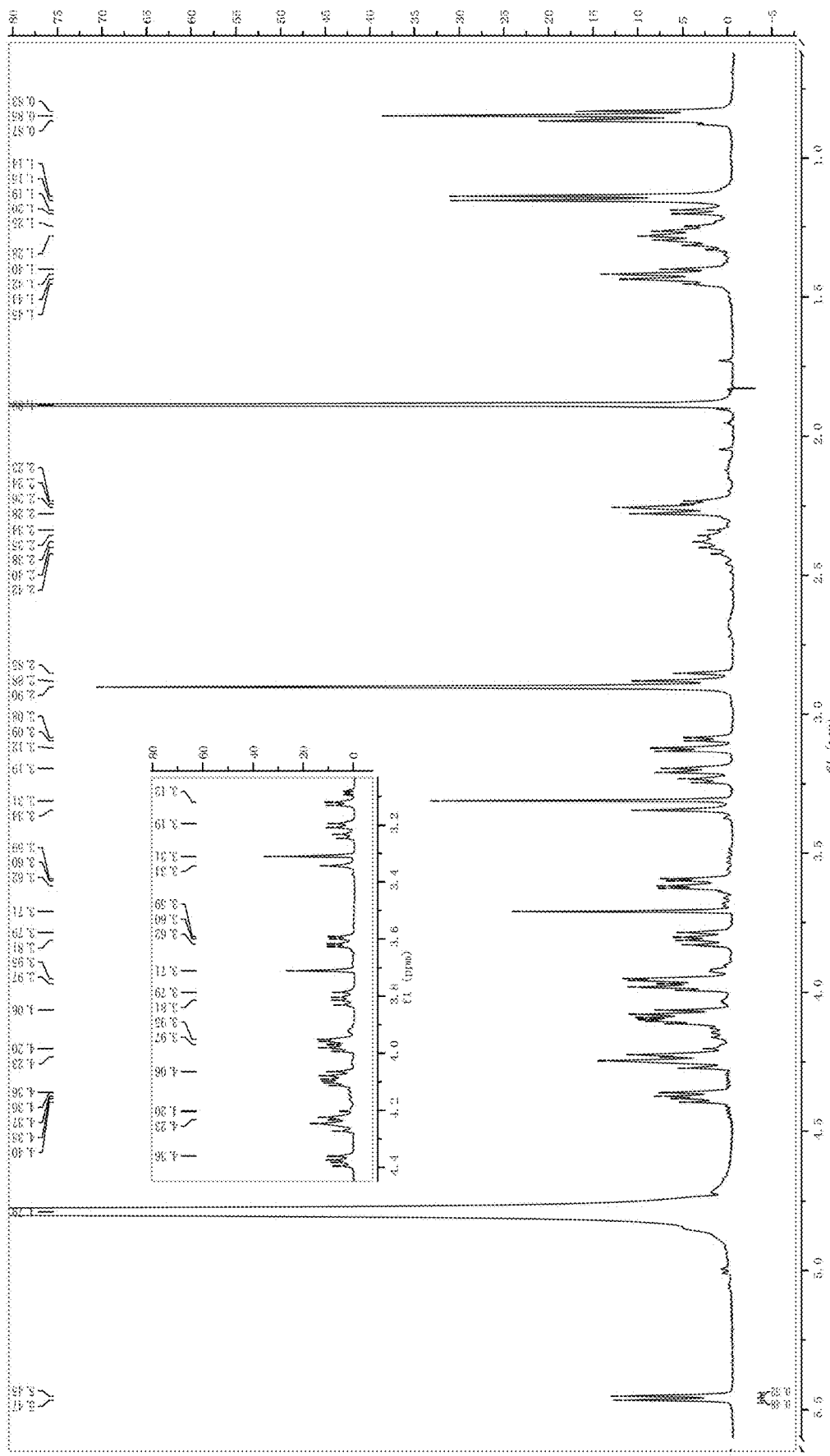
Figure 7B:
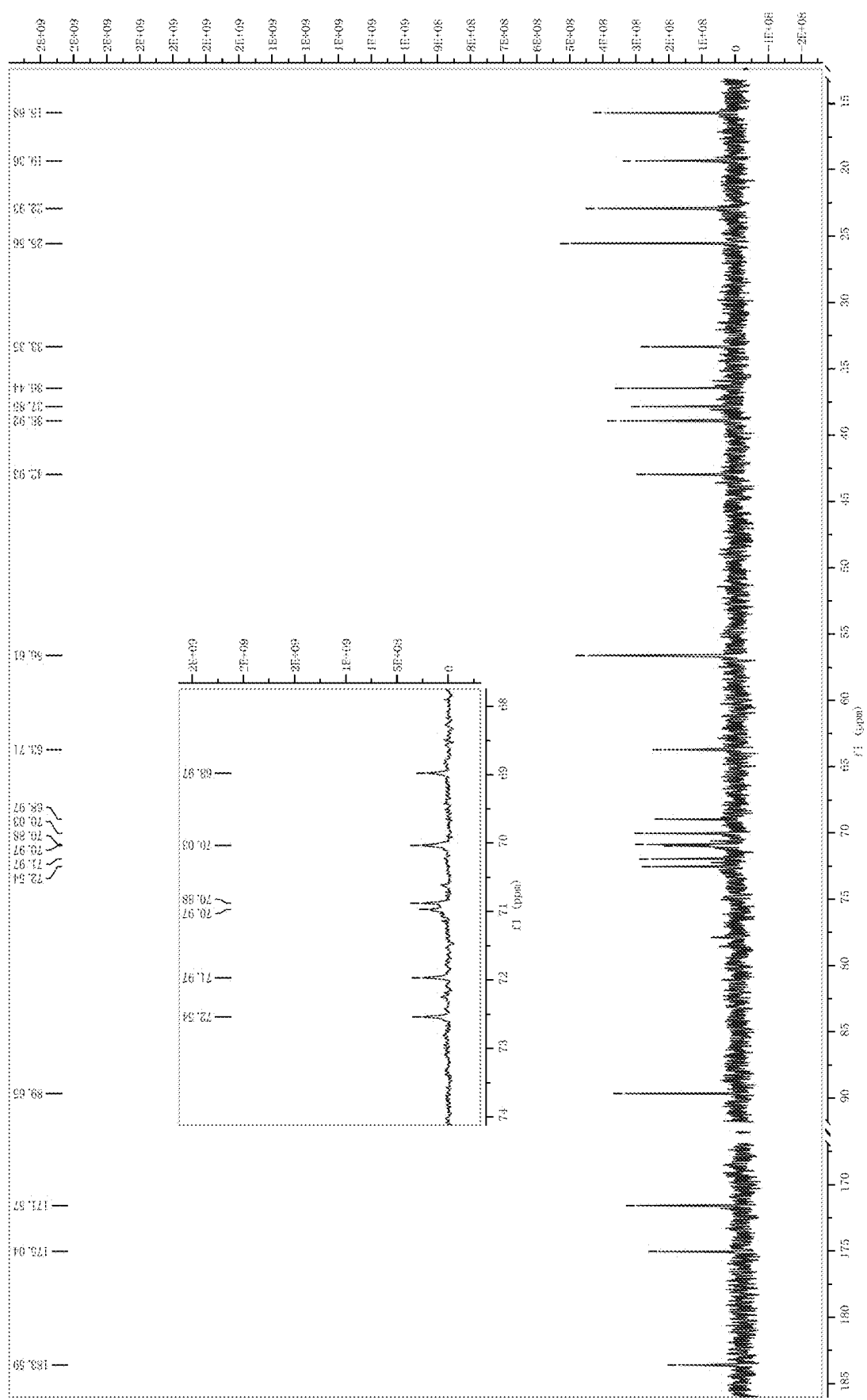
Figure 7C:
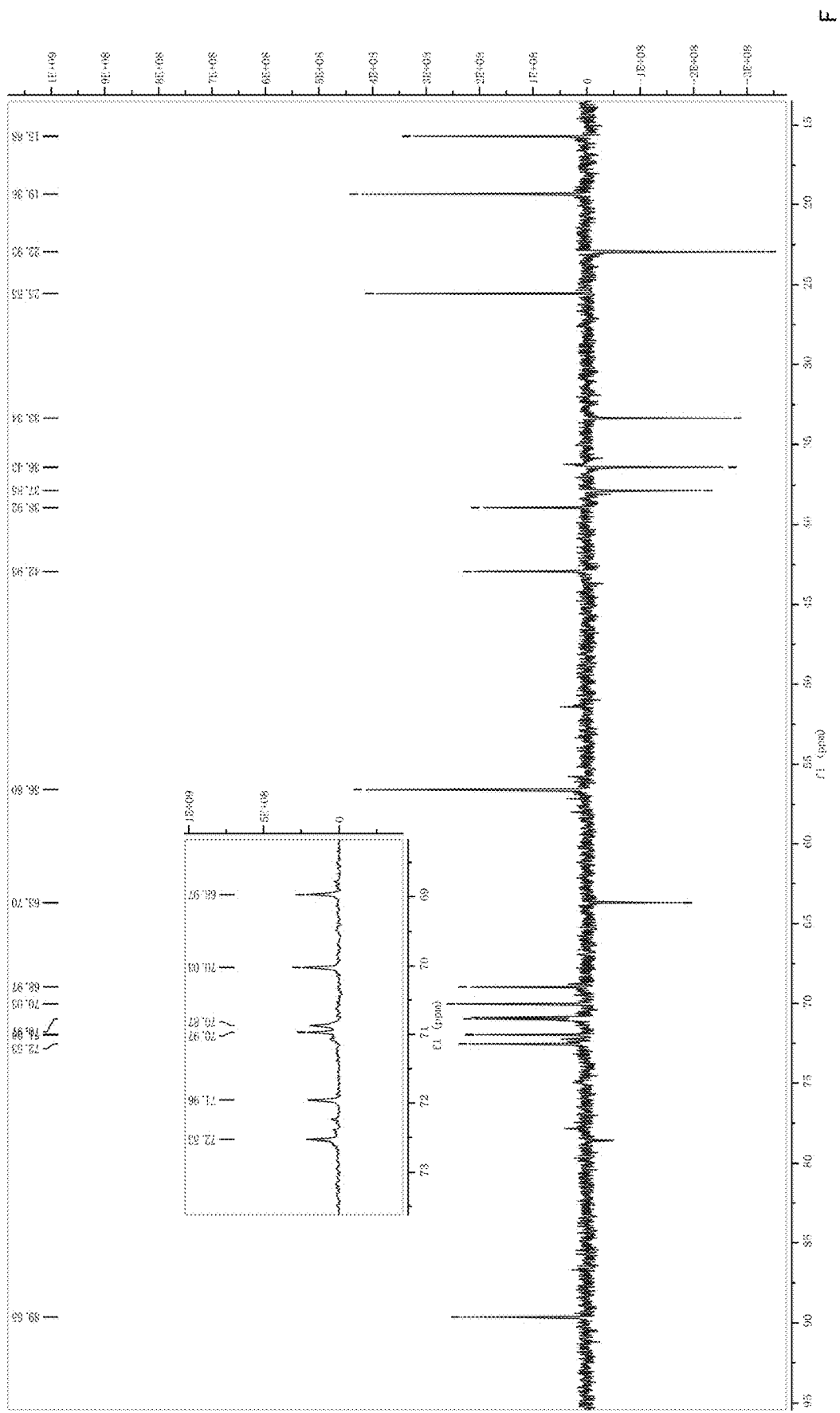
FIG. 7c, DEPT135 NMR spectrum.
Figure 7D:
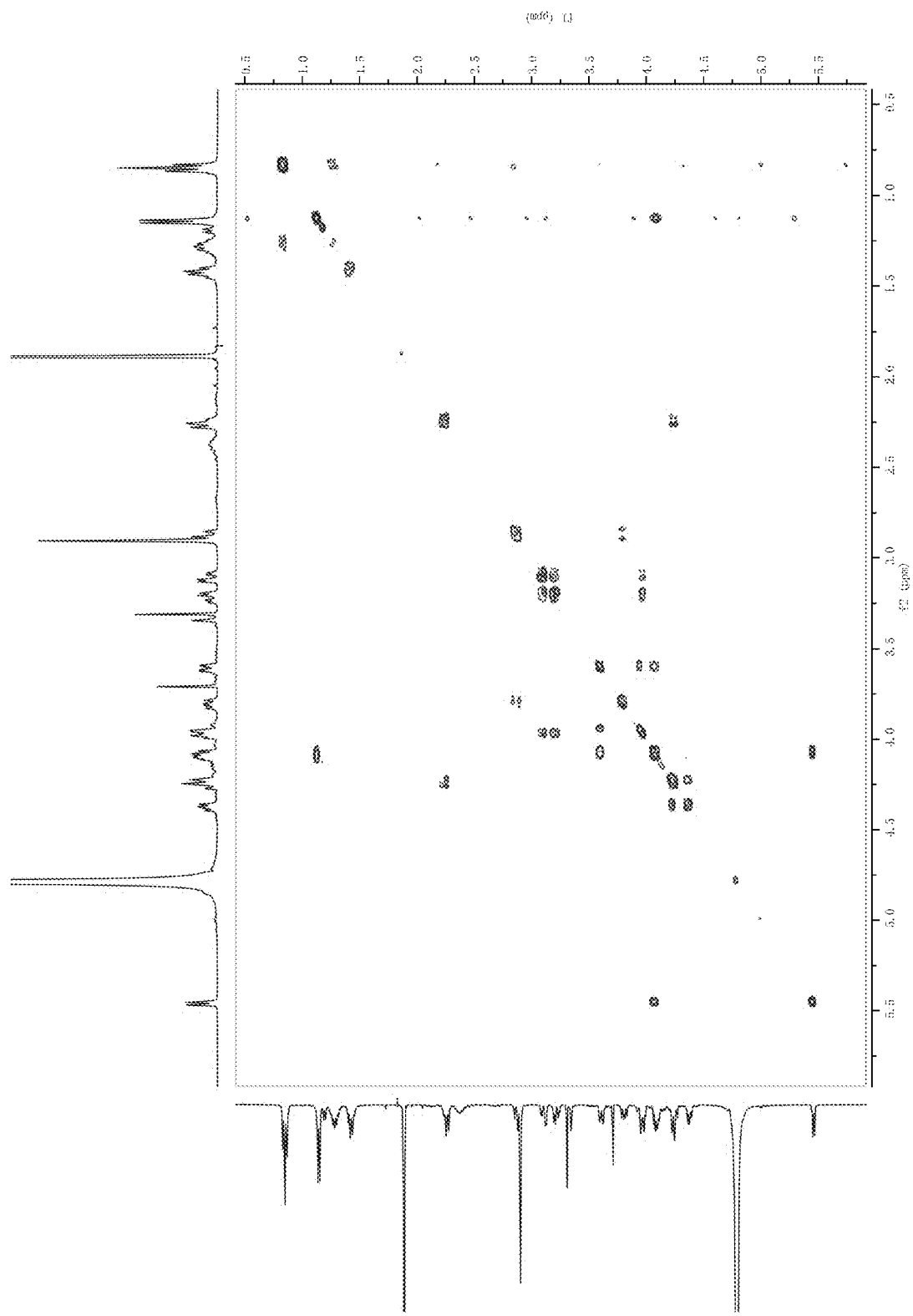
FIG. 7d, COSY NMR spectrum.
Figure 7E:
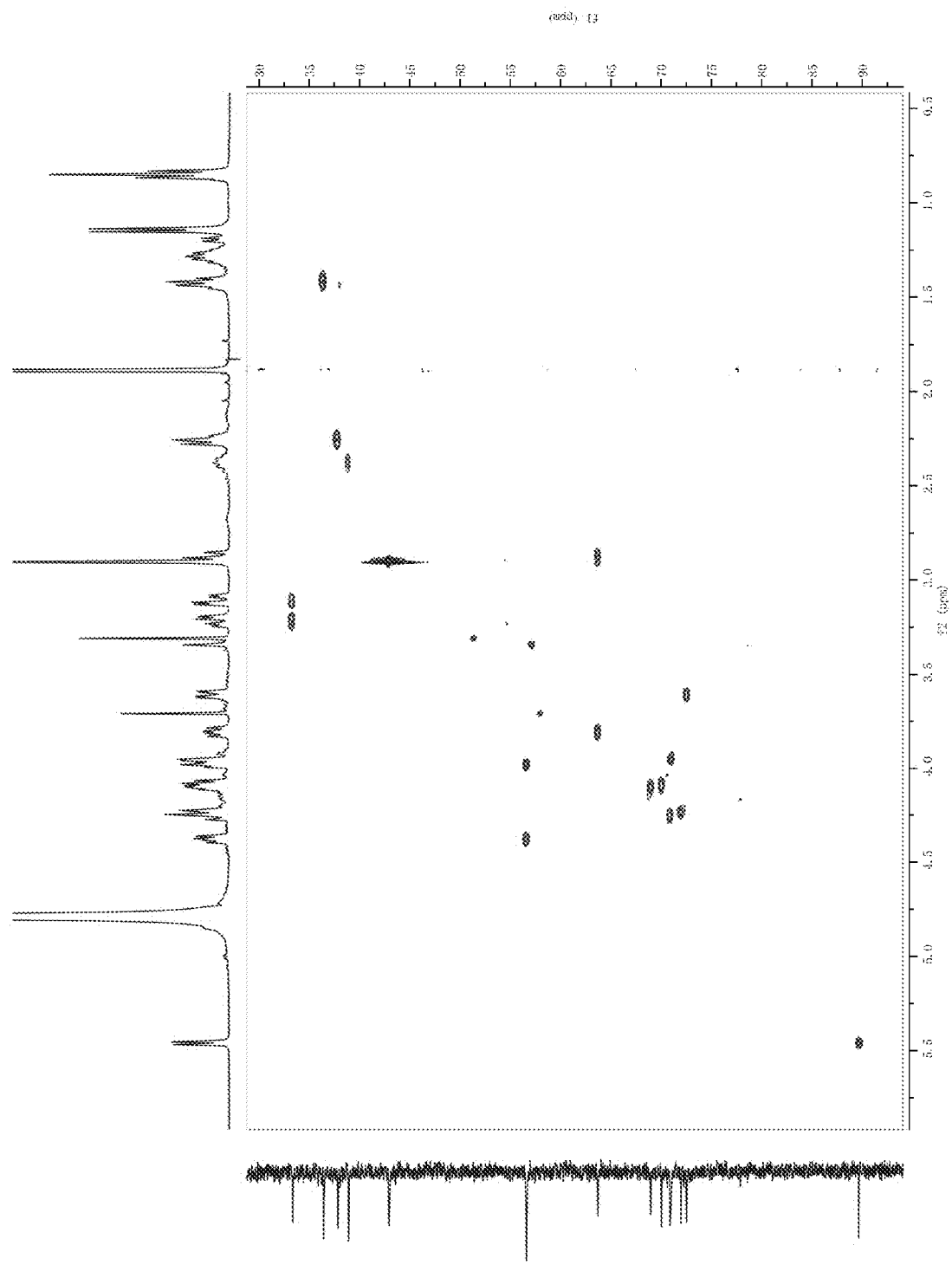
FIG. 7e, HSQC NMR spectrum.
Figure 7F:
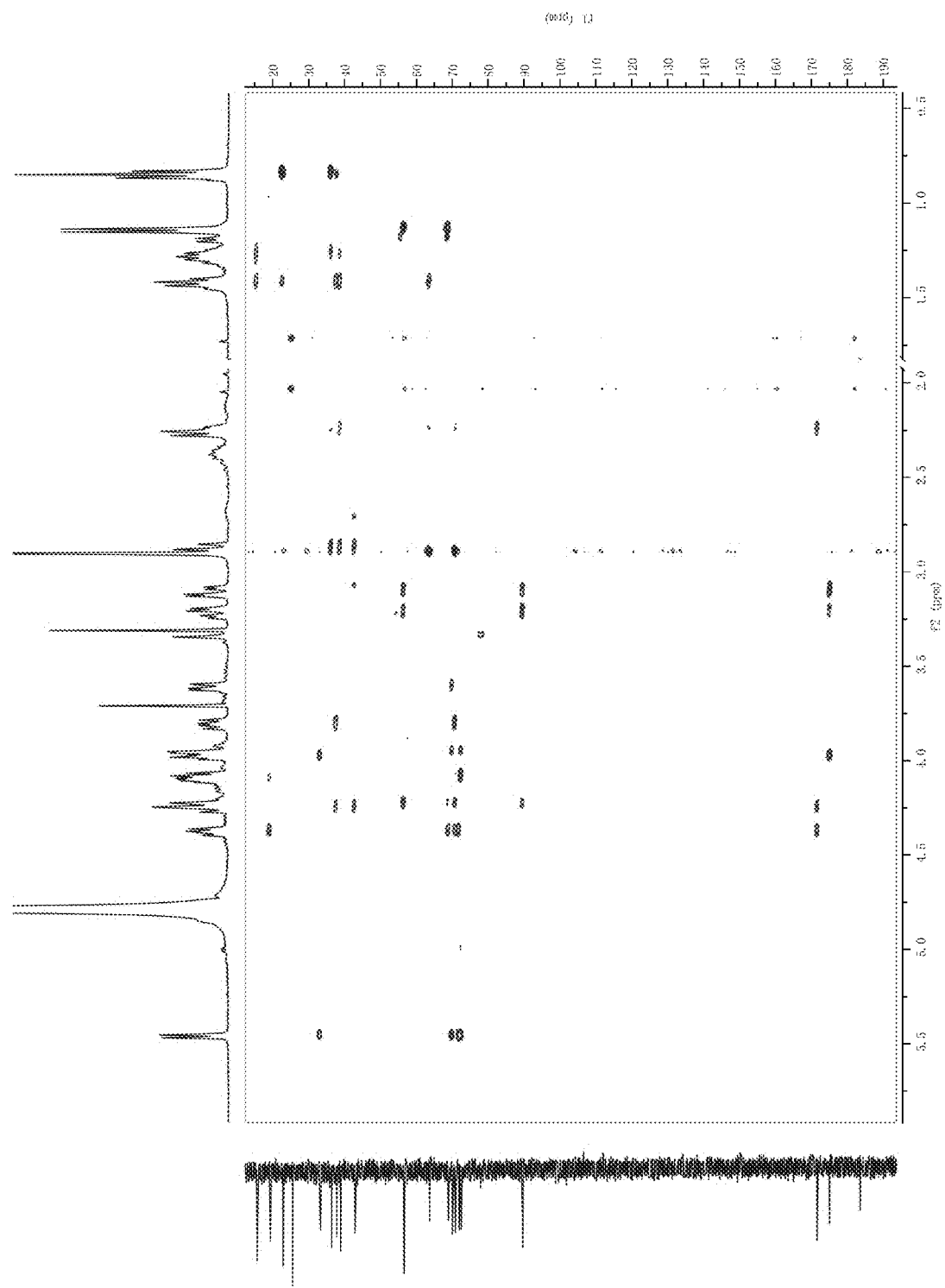
FIG. 7f, HMBC NMR spectrum.
Figure 7G:
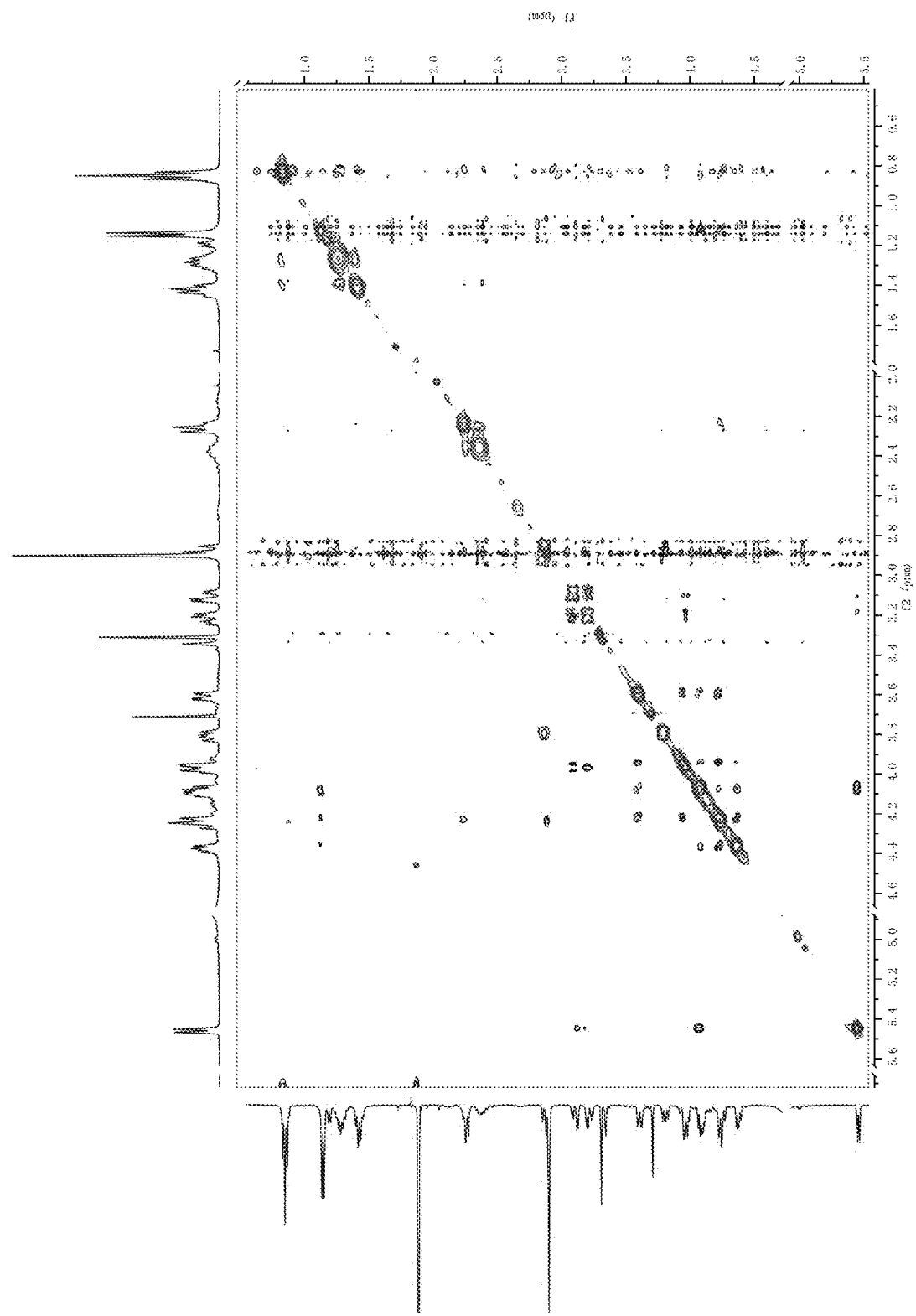
FIG. 7g, NOESY NMR spectrum.
Figure 8A:
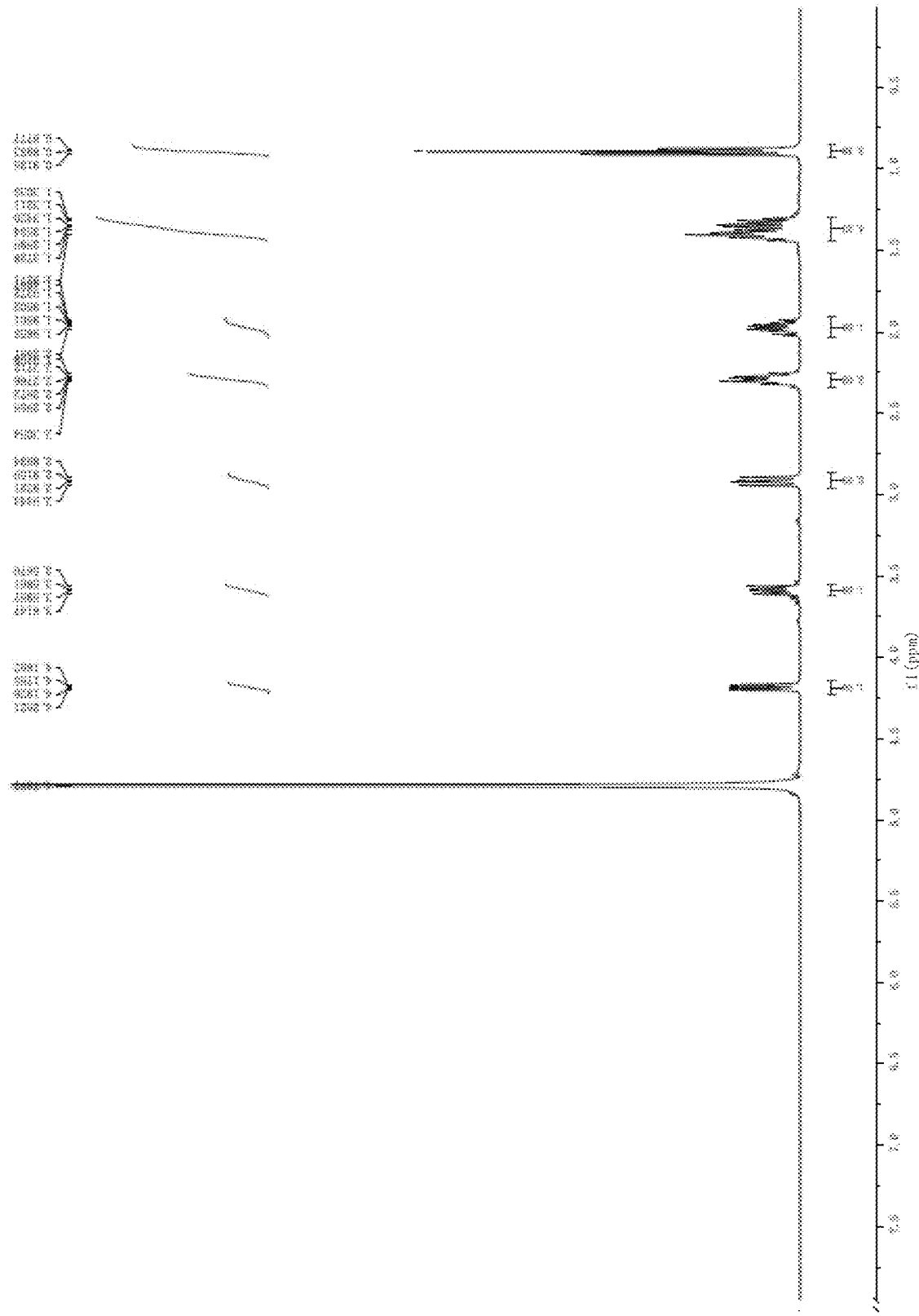
Figure 8B:
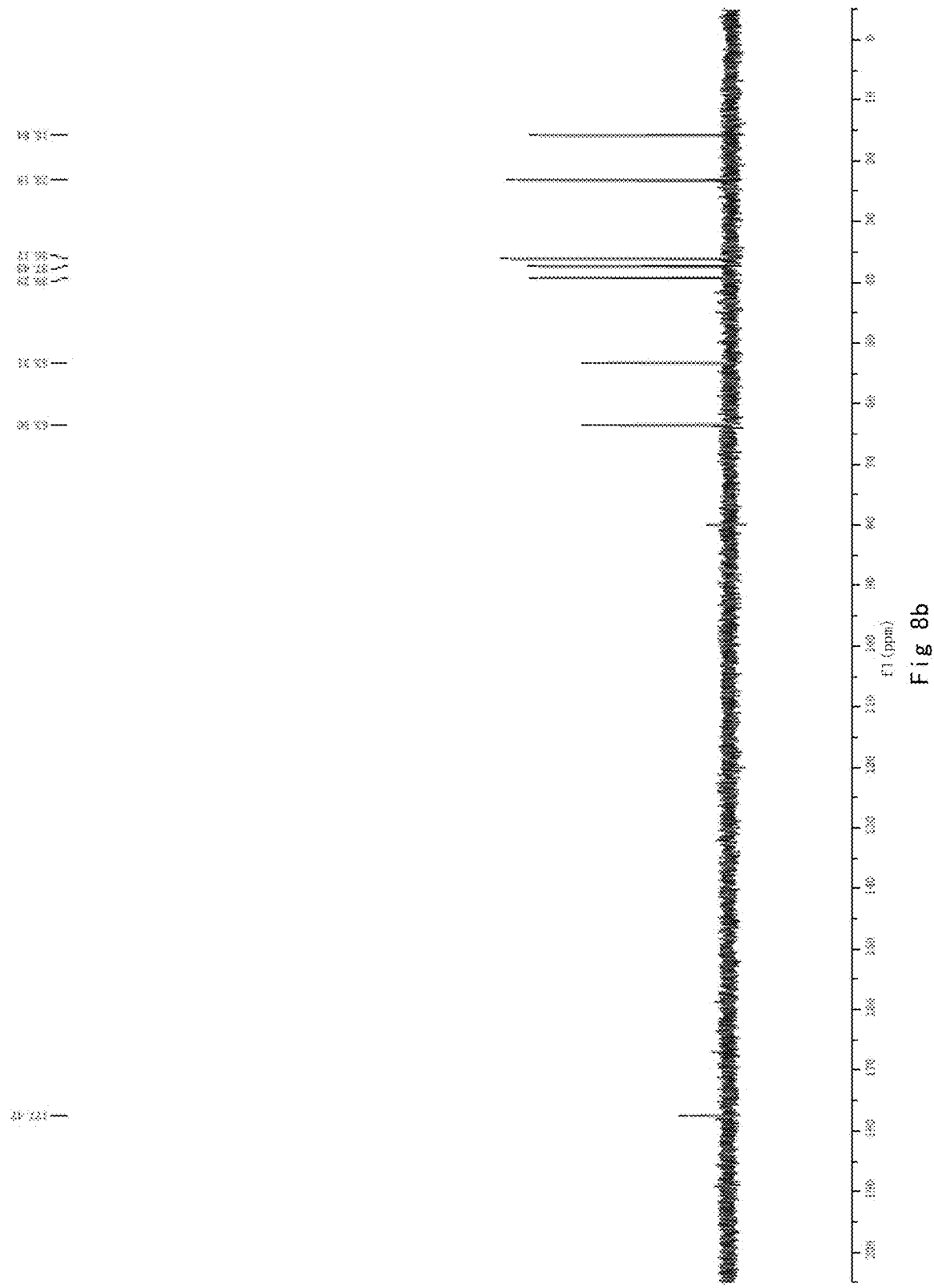
Figure 8C:
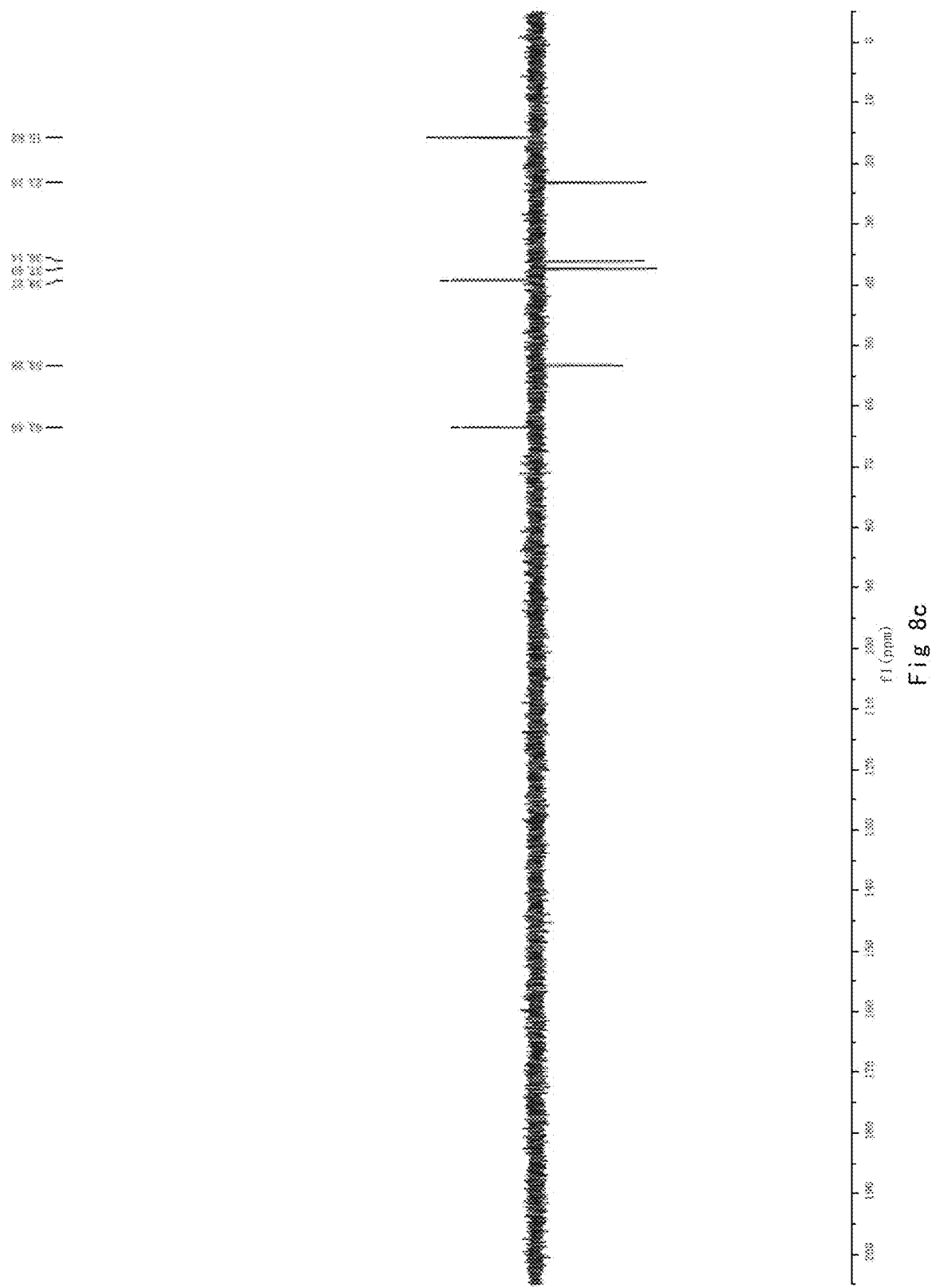
FIG. 8c, DEPT135 NMR spectrum.
Figure 8D:
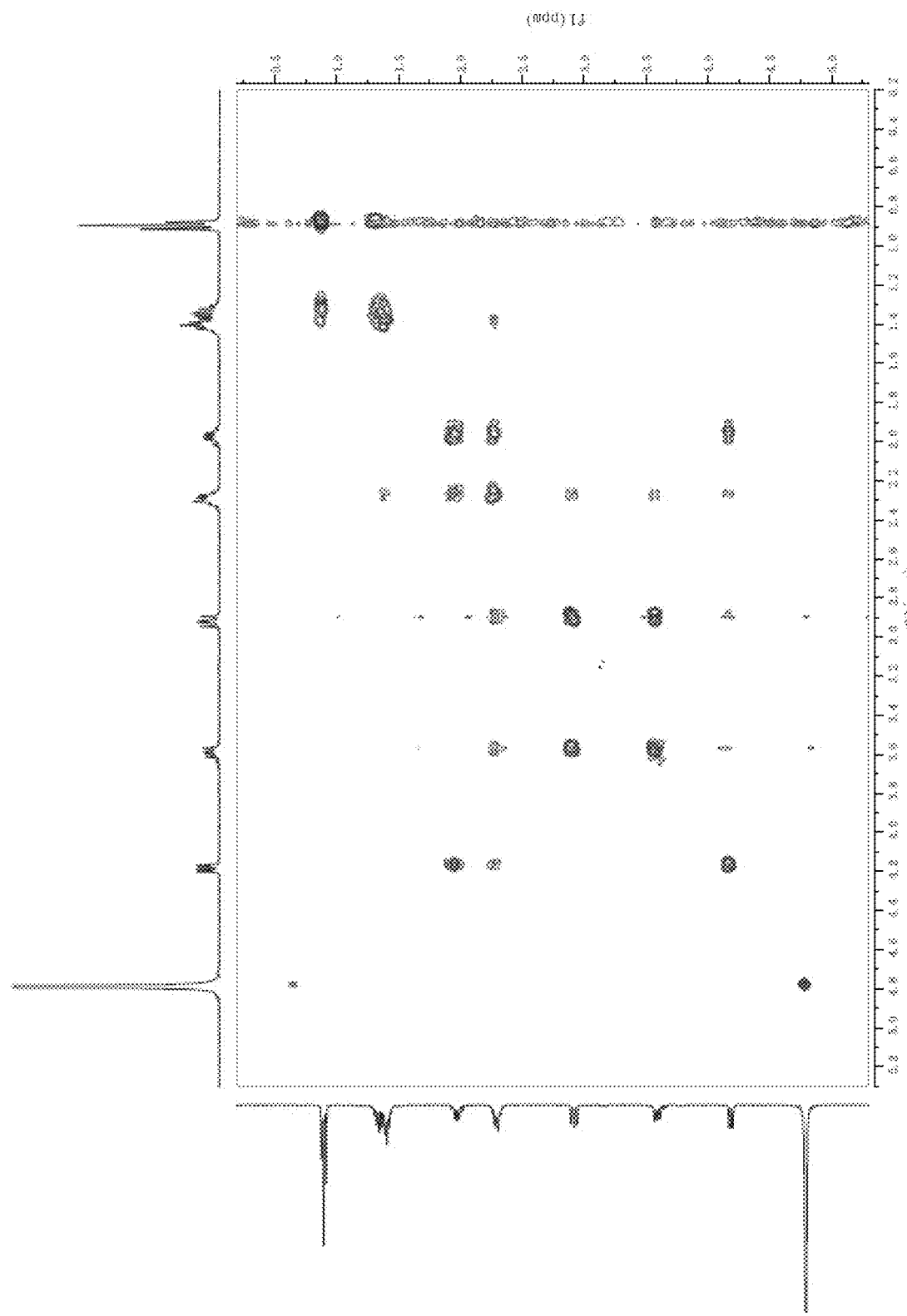
FIG. 8d, COSY NMR spectrum.
Figure 8E:
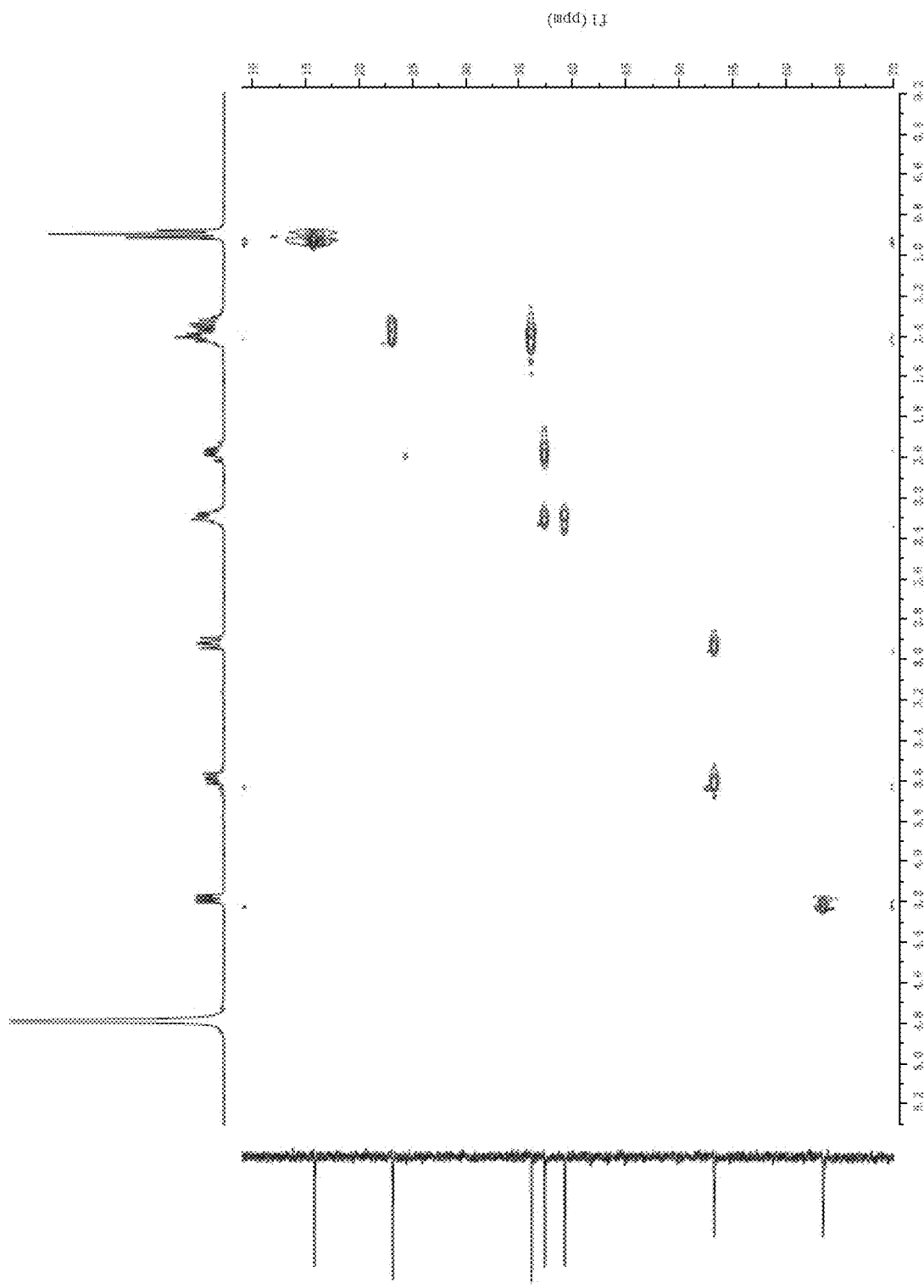
FIG. 8e, HSQC NMR spectrum.
Figure 8F:
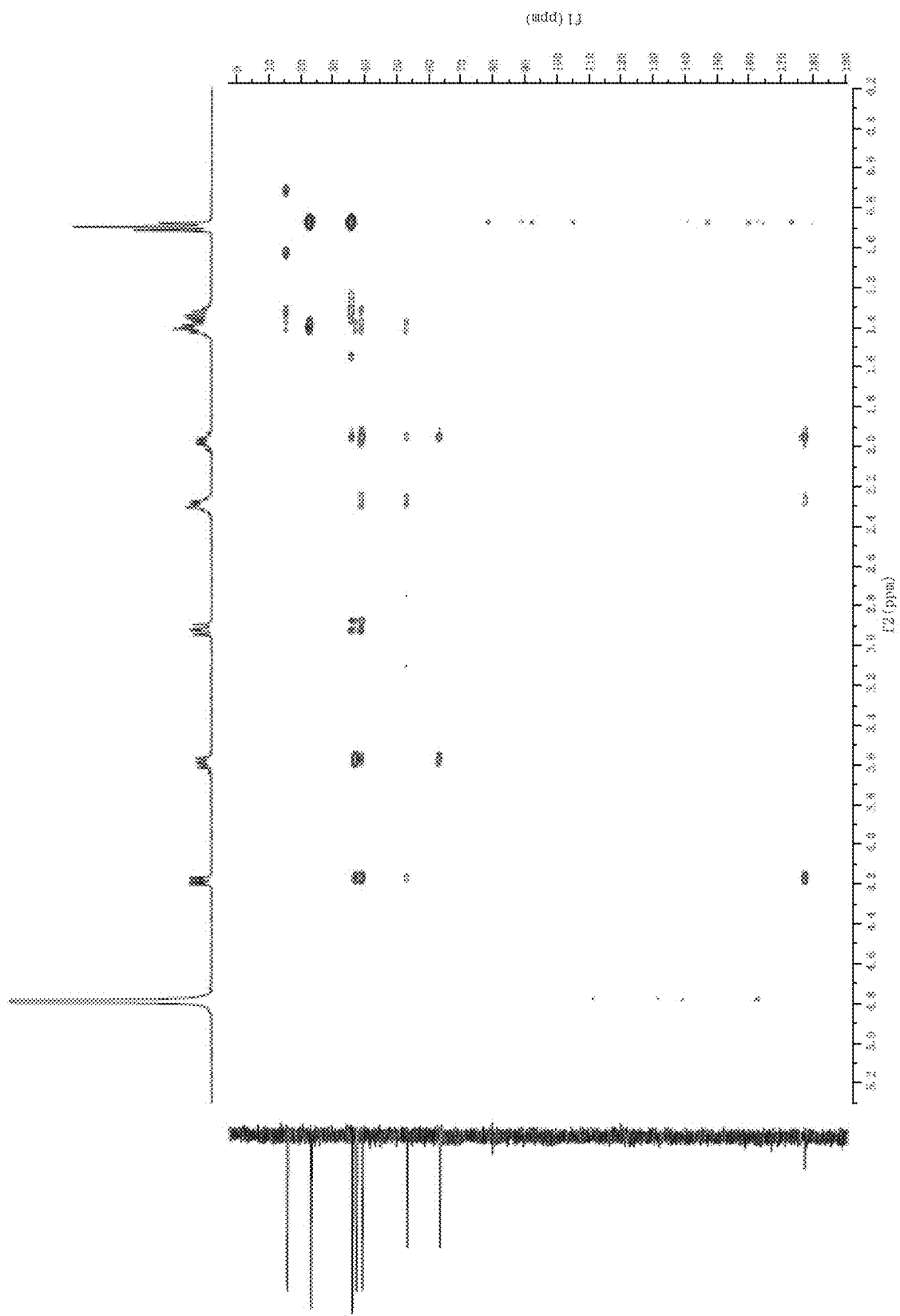
FIG. 8f, HMBC NMR spectrum.
Figure 8G:
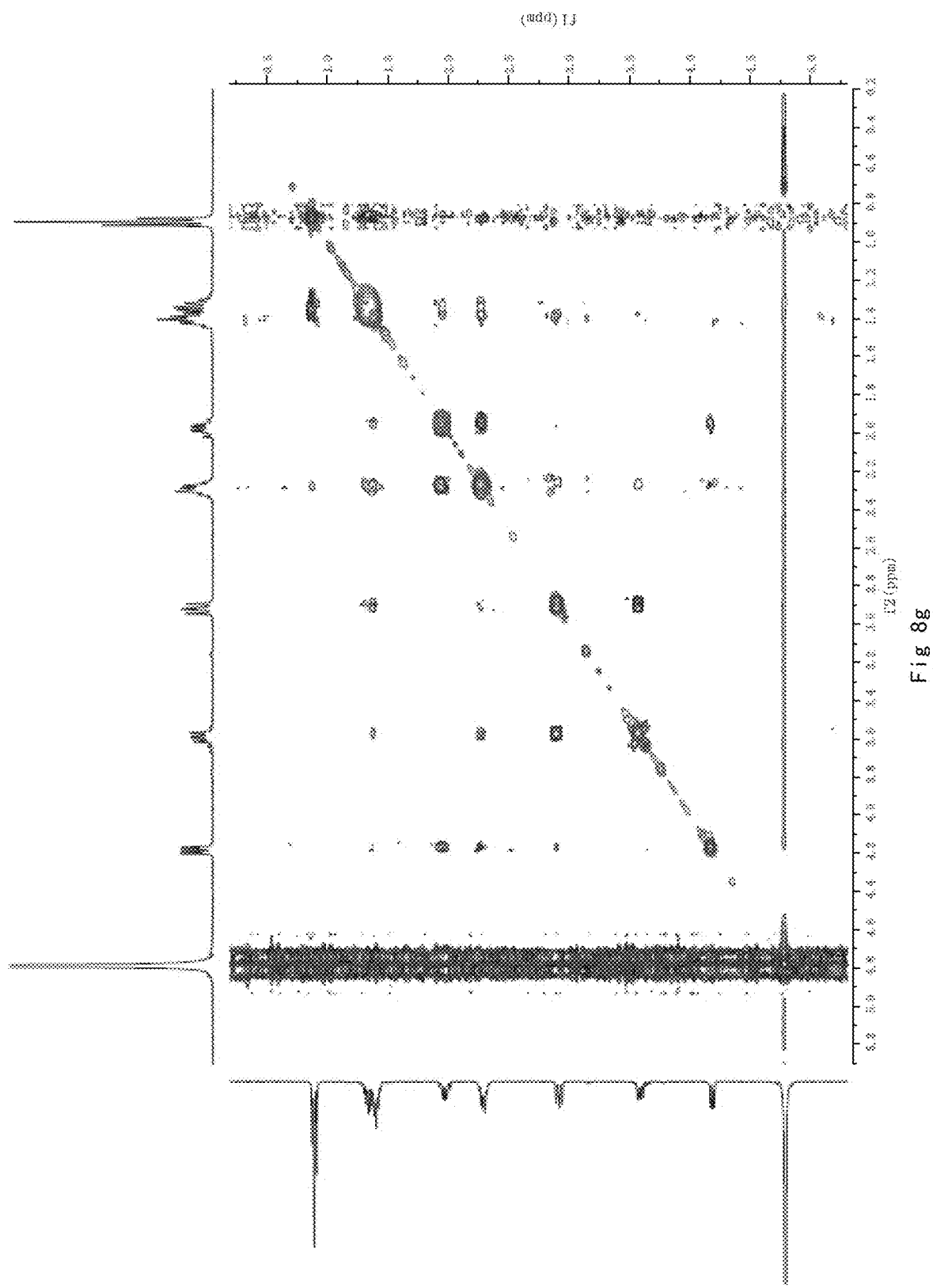
FIG. 8g, NOESY NMR spectrum.

FIG. 4 shows the results of NMR analysis of compound 2, FIG. 4a, 1H NMR spectrum; FIG. 4b, 13C NMR spectrum; FIG. 4c, DEPT135 NMR spectrum; FIG. 4d, COSY NMR spectrum: FIG. 4e, HSQC NMR spectrum: FIG. 4f, HMBC NMR spectrum; FIG. 4g, NOESY NMR spectrum. The structure of Compound 2 was identified based on the above spectra as shown in Formula I2.

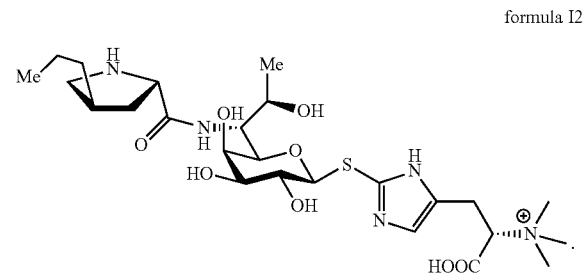

formula I2

FIG. 5 shows the results of NMR analysis of compound 3. FIG. 5a, 1H NMR spectrum; FIG. 5b, 13C NMR spectrum; FIG. 5c, DEPT135 NMR spectrum; FIG. 5d, COSY NMR spectrum; FIG. 5e, HSQC NMR spectrum; FIG. 5f, HMBC NMR spectrum; FIG. 5g, NOESY NMR spectrum. The structure of Compound 3 was identified based on the above spectra as shown in Formula I3.

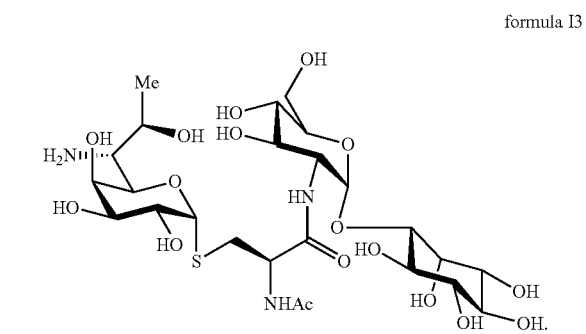

formula I3

FIG. 6 shows the results of NMR analysis of compound 4. FIG. 6a, 1H NMR spectrum; FIG. 6b, 13C NMR spectrum; FIG. 6c, DEPT135 NMR spectrum; FIG. 6d, COSY NMR spectrum; FIG. 6e, HSQC NMR spectrum; FIG. 6f, HMBC NMR spectrum; FIG. 6g, NOESY NMR spectrum. The structure of Compound 4 was identified based on the above spectra as shown in Formula I4.

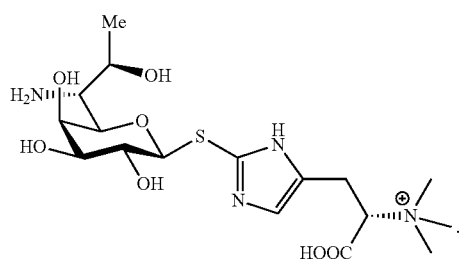

formula I4

FIG. 7 shows the results of NMR analysis of compound 5. FIG. 7a, 1H NMR spectrum; FIG. 7b, 13C NMR spectrum; FIG. 7c, DEPT135 NMR spectrum; FIG. 7d, COSY NMR spectrum; FIG. 7e, HSQC NMR spectrum; FIG. 7f, HMBC NMR spectrum; FIG. 7g, NOESY NMR spectrum. The structure of Compound 5 was identified based on the above spectra as shown in Formula I5.

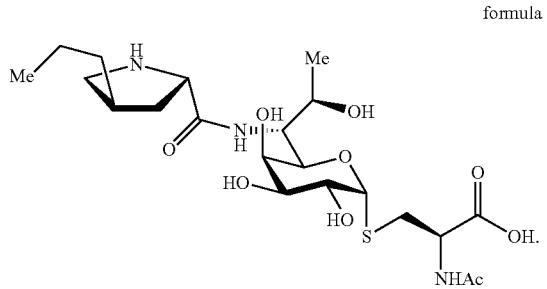

formula I5

Example 5

Pharmaceutical Composition

| Compound | 20 g |
|---|---|
| starch | 140 g |
| Microcrystalline cellulose | 60 g |

The above substances are mixed by conventional methods, and then filled into general gelatin capsules to obtain 1000 capsules.

Example 6 Production of Downstream Products Such as n-Propyl Proline, Disaccharide GlcN-Ins and Ergothioneine by Hydrolysis N-propyl proline: 5 ml of an aqueous solutions of Compound 1, 2 or 5 (containing about 50 mg of starting material) were taken in a 25 ml round bottom flask, and 5N NaOH solution was added dropwise to pH=11, and heated to reflux for 3 h. After the reaction was completed by LC-MS, the reaction solvent was removed under vacuo. The system was dissolved in 1 ml water, and semi-preparative purifications were performed on a reversed-phase C18 column for twice. Conditions: $H_2O$ (5 mM)/$CH_3OH$=80/20; 2 ml/min; 210 nm UV detection, and the obtained pure n-propyl proline was subjected to nuclear magnetic identification. The results are shown in FIG. 8. The identification results show that the n-propyl proline was successfully produced in this example.

Figure 9B:
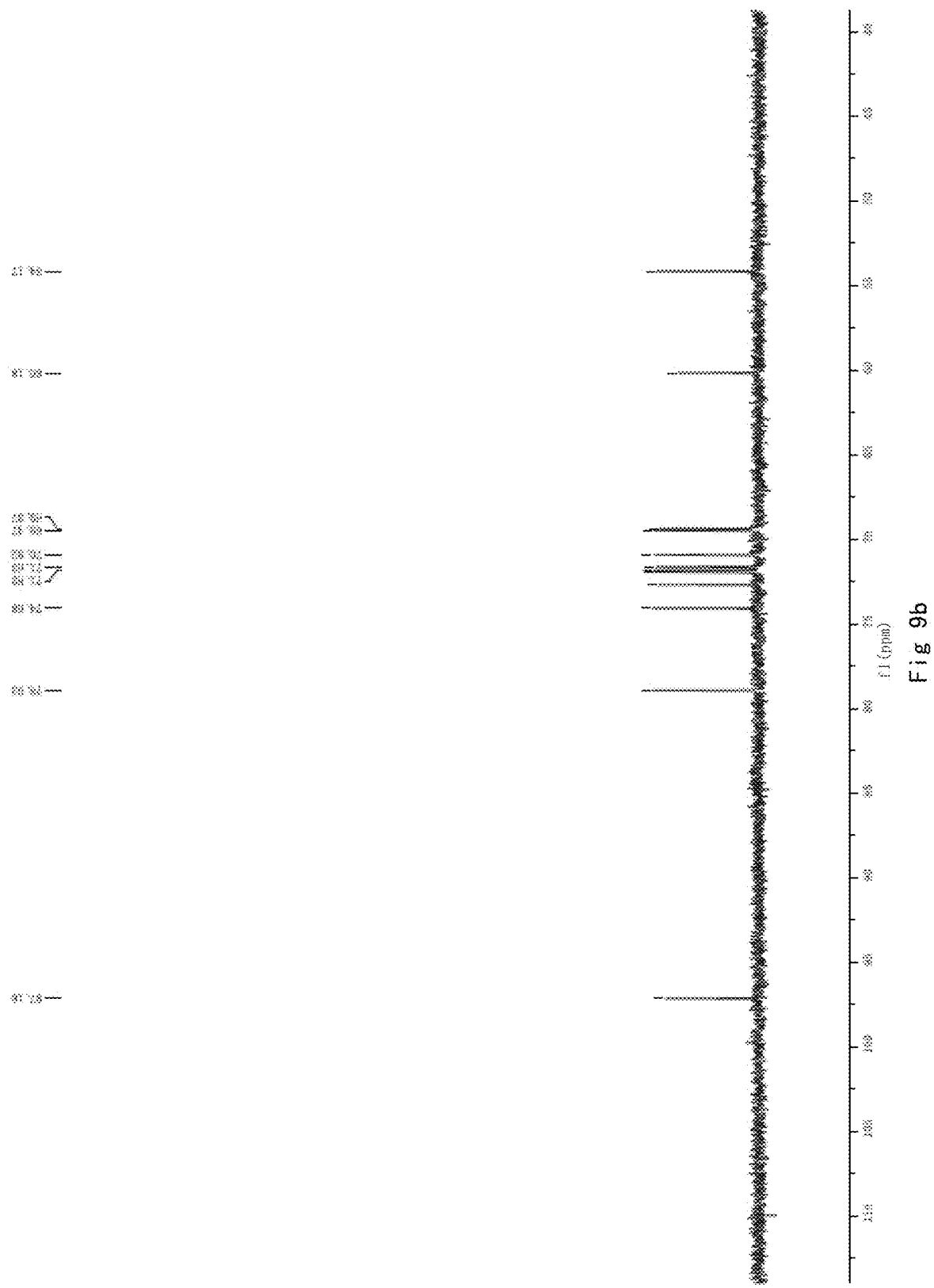

Disaccharide GlcN-Ins: 5 ml of an aqueous solutions of Compound 1 or 3 (containing about 50 mg of starting material) were taken in a 25 ml round bottom flask, and 5N NaOH solution was added dropwise to pH=11, and heated to reflux for 3 h. After the reaction was completed by LC-MS, the reaction solvent was removed under vacuo. The system was dissolved in 1 ml water, and semi-preparative purifications were performed on a HIIIC column for twice. Conditions: $H_2O$ (10 mM)/CH3CN=25/75; 2 ml/min; differential detection, and the obtained GlcN-Ins was subjected to nuclear magnetic identification. The results are shown in FIG. 9. The identification results show that the disaccharide GlcN-Ins was successfully produced in this example. GlcN-Ins can be used as the raw material of Mycothiol chemical synthesis (The chemical synthesis method refers to: *Org. Lett.* 6, 365-368, 2004; *Org. Lett.* 12, 2630-2633, 2010).

Figure 10:
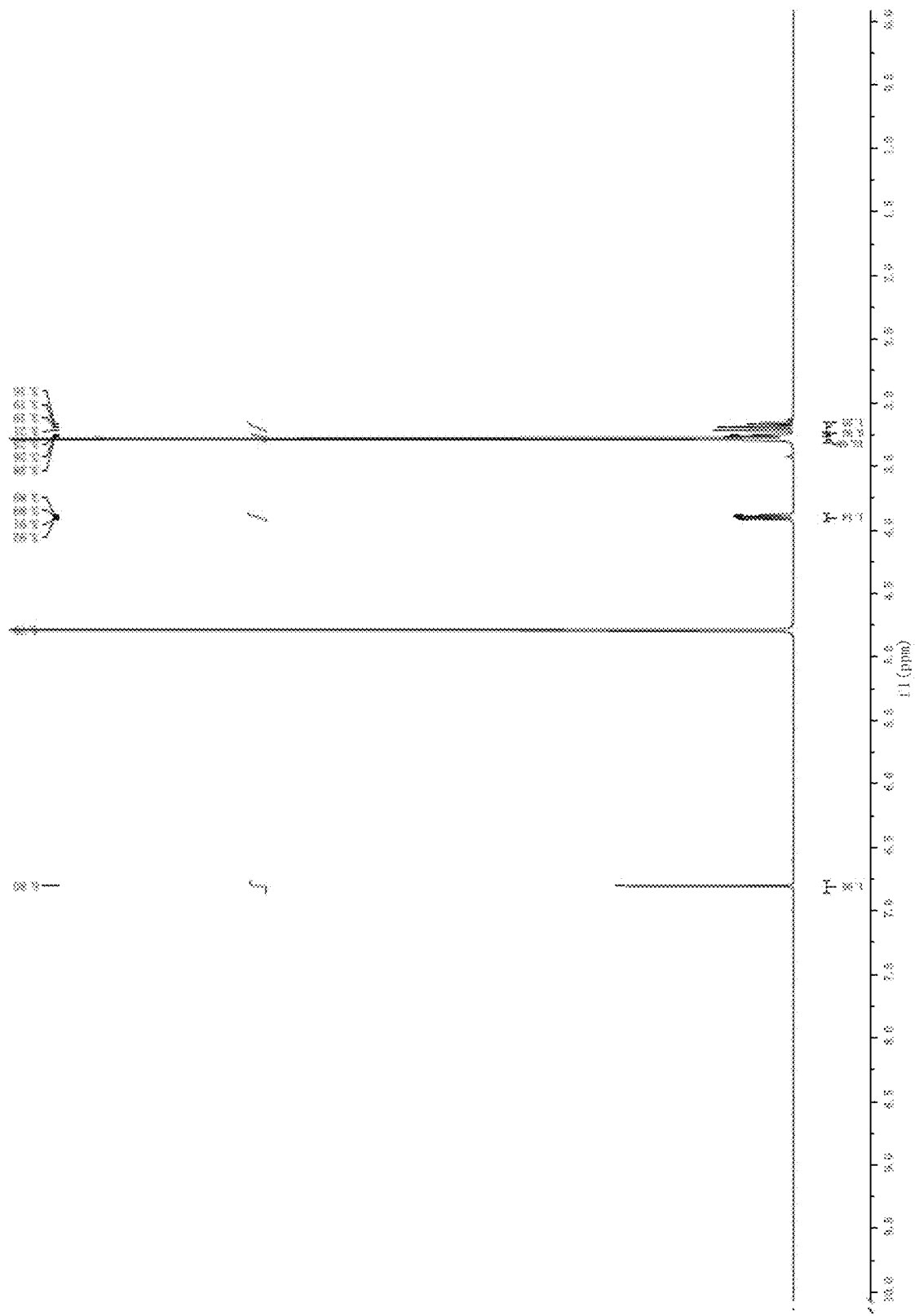
FIG. 10 shows NMR analysis of ergothioneine, 1H NMR spectrum.

Ergothioneine: 5 ml of an aqueous solutions of Compound 2 or 4 (containing about 50 mg of starting material) were taken in a 25 ml round bottom flask, and 5N HCl solution was added dropwise to pH=1, and heated to reflux for 3 h. After the reaction was completed by LC-MS, the reaction solvent was removed under vacuo. The system was dissolved in 1 ml water, and semi-preparative purifications were performed on a HIIIC column for twice. Conditions: $H_2O$ (10 mM)/CH3CN=28/72; 2 ml/min; 243 nm UV detection, and the obtained pure Ergothioneine was subjected to nuclear magnetic identification. The results are shown in FIG. 10. The identification results show that the Ergothioneine was successfully produced in this example.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

We claim:

1. A microbial strain, wherein the microbial is *Streptomycin lincolnensis*, and in the strain, one or more genes selected from a group consisting of the following have been inactivated or knocked out:
   lmbE, lmbE3457, lmbV, mshA, mshC, lmbC, lmbD, lmbN, and lmbF.

2. The strain of claim 1, wherein in the strain, lmbE and/or lmbE3457 genes are inactivated or knocked out; and/or
   the lmbV, mshA and/or mshC genes are inactivated or knocked out; and/or
   the lmbC, lmbD and/or lmbN genes are inactivated or knocked out; and/or
   the lmbF gene are inactivated or knocked out.

3. A preparation method for a compound, wherein the method comprises:
   (a) fermenting a microbial strain, wherein the microbial is *Streptomycin lincolnensis*, and in the microbial strain, one or more genes selected from the group consisting of the following have been inactivated or knocked out: lmbE, lmbE3457, lmbV, mshA, mshC, lmbD, lmbN, and lmbF to obtain a fermentation product containing the compound; and
   (b) isolating the compound from the fermentation product; and optionally converting the compound into a pharmaceutically acceptable salt thereof, wherein the compound is represented by formula I:

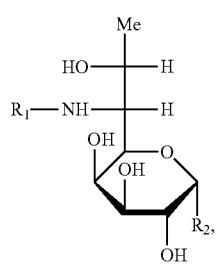

Formula I wherein $R_1$ is selected from a group consisting of H, halogen, $C_{1-8}$alkyl, $C_{2-8}$ alkenyl, $C_{2-8}$ alkynyl, and

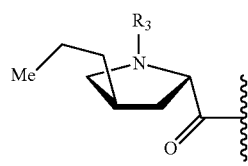

where $R_8$ is selected from a group consisting of H, halogen and $C_{1-8}$ alkyl; and
$R_2$ is selected from
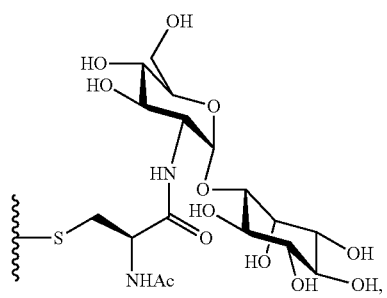
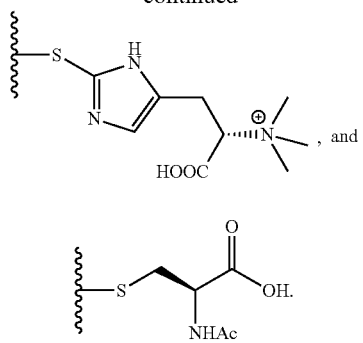

UNITED STATES PATENT AND TRADEMARK OFFICE
CERTIFICATE OF CORRECTION

PATENT NO. : 10,590,159 B2  
APPLICATION NO. : 15/575630  
DATED : March 17, 2020  
INVENTOR(S) : Liu et al.

Page 1 of 1

It is certified that error appears in the above-identified patent and that said Letters Patent is hereby corrected as shown below:

On the Title Page

Item (72), should read:  
(72) Inventors: Wen LIU, Shanghai (CN); Qunfei ZHAO, Shanghai (CN); Min WANG, Shanghai (CN); Dongxiao XU, Shanghai (CN) and Qinglin ZHANG, Huzhou, Zhejiang (CN).

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 33

<210> SEQ ID NO 1
<211> LENGTH: 813
<212> TYPE: DNA
<213> ORGANISM: Streptomyces lincolnens

<400> SEQUENCE: 1
atgactcagt gcctgctgac cgtccacgcg cacccggacg acgaggcctc ccgcggcggc    60

```
gccacggtcg cccactacac cgcgcagggc gtccgcgccg tcctggtcac ctgtaccgac      120
ggcggcgccg gcgaggtgct caaccccgcc gtcaccgacg acttcacccc cgaacggttc      180
gtcgccgtcc gcagcgccga actcgacgcc agcgcacgga acctgggcta ctcggccgtg      240
caccggctcg gctaccgcga ctccggcatg gacggcacgg cgggcggcgc cgaggccttc      300
gtacgggccc cgctcgacga ggccgccacc cgcctcgccc gggtgatcgc ggacgaacgc      360
cccgacgtgg tgatcggata cggcaccaac cacaccgcg acccgcaccc cgaccacatc       420
cgcgcgaacg aagtgctgac gcgcgccgtc gacctcctcg accacacacc cgccgtctac      480
cacatcgcct tctcgcgacg tcgccaccgc gccttgcacc aggcctgcgt cgacagcggg      540
gtgcccagcc cgtacgaggg cggcctgagc gccccgccgg gcgccttcga cgacgagtgg      600
atcaccacac tcgtcgacgt gaccaagggc gacgccgtcg agcgcaggct cgacgcgctg      660
cgcagtcacg tgacccaagt accgcccgcc tccggctggt tcgcgctgtc accgcagcag      720
ctgcgggacg ccttcccgta cgaggagtac acccgcgtcg cgccgcgcc ccgggaagcc      780 gtggtgcacg acctgttcac cgctcccgcg tga                                  813

<210> SEQ ID NO 2
<211> LENGTH: 861
<212> TYPE: DNA
<213> ORGANISM: Streptomyces lincolnens

<400> SEQUENCE: 2
atggccgtgc acgcccaccc cgacgacgag tcgagcaagg gcgcggccac catggcgaag      60
tacgtgtccg aggggtgga cgtgctggtc gtgacctgca cggggagggga gcgcggctcc      120 atcctcaacc ccaagctcca gggggacgcg tatatcgagg agcacatcca tgaggtgcgc      180
aagaaggaga tggacgaggc gagagagatc ctcggcgtca gcaggagtg gctcgggttc      240 gtcgactcgg gcctgcccga ggggaccccg ctgccgccgc tgccggaggg ctgtttcgcc      300
ctggaggacg tcgacaaggc ggccggtgag ctggtgaaga agatccgctc gttccgtccc      360
caggtgatca ccacctacga cgagaacggc ggctacccgc accccgacca catcatgacc      420
cacaagatct cgatggtggc gttcgagggt gccgcggaca ccgagaagta cccggagcag      480
gagttcggcc ccgcgtacca gccgcagaag atctactaca accagggctt caaccgtgag      540
cgcaccgagg ccctgcacaa cgcgctggtc gagcgcggcc tggagtcccc ctacggcgac      600
tggctcaagc gctgggagga gtccgggatg cagcagcgga cgctcaccac gcacgtcccg      660
tgtgccgagt tctacgagat ccgcgacaag gccctgatcg cccacgccac gcagatcgac      720
cccgacggcg gctggttccg ggtgccgctg gatctccaga aggaggtctg gccgaccgag      780
gagtacgagc tcgcgaagtc cctcgtcgat acttccctcc ccgaggcgga cctctttgcg      840
ggcatccgcg acaatgcctg a                                               861

<210> SEQ ID NO 3
<211> LENGTH: 720
<212> TYPE: DNA
<213> ORGANISM: Streptomyces lincolnens

<400> SEQUENCE: 3
ttgcagcgca agggactggc ccggctcggg tcgggtgtca cggcactggc cgacgaggga      60
agacacctgc gggcctggct cacgagcgcc gacgcggcgg cgtggcgacg gcccacacgc      120
tgtgcggagt ggaacgtccg ggacgtcgtc gcgcacctgg cgagcggcga gctgtacaac      180
caggcatgcg tgcacgacga catcgcctcg ctcggcgagt gggccgacga cgaggcgtac      240
```

```
aacgtcggcc aggtggagat gcgccgccac ctgagccacc gcgacgtctt cgcggagtgg    300
gacgagcgcc accgggacgt ggtggccgcc tgggggggcca tggacccggc cgacccgctc    360
accacgagct ggggaccgta cctggtcggc ctgcaggcgt ggcacatcgc gtcggagtac    420
gcgacccacg ccgacgacat cggggtcccc gtccccgcgg agcgggccgc ctcccggctc    480
gactggcgcc tcgccttctc ccagtacgcg gtcgaggagt gcgagctggg ccttacggtc    540
gagcccgccg agggcgacag tgtgctcgtg cggacgggg ccggggccgg ggccgaactc    600
gtactgaccc gtgagcagtt cgtggccgcg gtcagcgccc ggctgccgta cgacgccgtc    660
gccgacgacc ccgccgttca cgcgctgcta cggcgcatga cggtgctggt ggggccgtga    720
```

<210> SEQ ID NO 4  
<211> LENGTH: 1338  
<212> TYPE: DNA  
<213> ORGANISM: Streptomyces lincolnens

<400> SEQUENCE: 4

```
gtgagccagt acgtcagcag gctccagcgt cgctcccagg ccgccacccc ccggctgcgc     60
ctgcaccgcc gcccccgccg cgtcgccatg ctctccgtgc acacctcgcc gctgcaccag    120
ccgggcaccg gcgacgcggg cggcatgaac gtctacatcg tggagctcgc ccagcgcctc    180
gccgcgatca acatcgaggt ggagatcttc acgcgggcga ccaccggcgg actcccgcac    240
tcggtcgagc tcgccccggg cgtcctcgtc cggcatgtcg acgccggccc gtacgagggc    300
ctggccaagg aggagctgcc cgcgcagctg tgcgccttca cgcacggcgt gatgcaggcg    360
tgggcgggcc accgccccgg ctactacgac ctggtgcact cgcactactg gctttccggc    420
cacgtcggct ggctcgccgc ccagcgctgg ggcaccccc tggtgcacgc catgcacacc    480
atggccaagg tcaagaacgc caacctggcc gacggcgaca ccccgagcc gccgcccgt    540 gtcatcggcg agacccagat cgtcgccgca gcggaccgcc tcatcgccaa caccgccgag    600
gagcgcgacg aactcgtacg gcactacgcc gccgaccccg acaaggtcgc ggtcgtgcac    660
cccggcgtga acctcgaccg cttccgcccc gccgacggcc gcgcggccgc ccgcgcccgc    720
ctcgggctgc cccaggacgc cctgatcccg ctgttcgcgg gccgcatcca gcccctgaag    780
gcccccgacg tgctcctgcg cgccgtggcg gtcctcctgg acgaacgccc cgacctgcgc    840
tcccgcctcc tcgtcccggt cgtcggcggt ctcagcggca gcggcctcgc caagccggag    900
ggcctccaga agctggcctc ccgcctcggt atcgcggacg tcgtacggtt ccacccgccc    960
gtcgggcagg agcagctcgc cgactggttc cgggccgcct ccgtgctcgt catgccgtcg   1020
tacagcgagt ccttcggact ggtcgccata gaggcgcagg cggccggcac ccccgtgctc   1080
gcggccgcgg tcgcggact cccggtcgcc gtccgcgacg ggcagaccgg tttcctcgta   1140
cgagggcaca atcccgccga ctacgcgcgc gtgctgcgcg acttcgccga cagccccgag   1200
ctcgcgcccc gcatgggcga ggccgccgcc cggcacgccg agttcttcgg ctgggacacc   1260
gcggccgccg ccaccgccga cgtctacacg gccgcgaccc agtcgcaccg ccgtcacgta   1320
cgctcccacc atgggtga                                                1338
```

<210> SEQ ID NO 5  
<211> LENGTH: 1230  
<212> TYPE: DNA  
<213> ORGANISM: Streptomyces lincolnens

<400> SEQUENCE: 5

-continued

| | |
|---|---|
| atgcatgcct ggcccgcttc cgaggtcccc gccctgcctg gtcagggccg cgacctgagg | 60 |
| atccacgaca ccgcgaccgg cggcctcgtc accctcaccc ccgtcccgt cgcccgtatc | 120 |
| tacgtctgcg gcatcacgcc gtacgacgcg acccacatcg gtcacgcggc gacctacaac | 180 |
| gcgttcgacc tcgtgcagcg cgtgtggctc gacaccaagc ggcaggtcca ctacgtccag | 240 |
| aacgtcaccg acgtcgacga tccgctcctg gagcgggcac agcgcgacgc catcgactgg | 300 |
| gtcgccctcg ccgagaagga gaccgccctc ttccgcgagg acatgaccgc cctgcggatg | 360 |
| ctgcccccgc ggcactacat cggcgcggtc gaggcgatac ccggcatcgt gccgctcgtc | 420 |
| gagcggctgc gggacgcggg cgccgcgtac gaactcgaag gggacgtgta cttctccgtc | 480 |
| gagtccgatc cgcacttcgg cgaggtctcc ggcctcgacg ccgccgccat gcggctgctg | 540 |
| tccgccgagc gcggcggcga ccccgagcgg cccggcaaga gaacccgct cgacccgatg | 600 |
| ctgtggatgg ccgcccgcga gggcgagccc agctgggacg gcgcctcgct ggggcgcggc | 660 |
| cggccgggct ggcacatcga gtgcgtcgcg atcgccctcg accacctcgg gatgggcttc | 720 |
| gacgtccagg gcggcggctc cgacctcgcc ttcccgcacc acgagatggg cgcctcgcac | 780 |
| gcccaggcgc tgaccggcga gttccccatg gccacggcgt acgtccacgc cggcatggtc | 840 |
| gccctccacg gcgagaagat gtccaagtcc aagggcaacc tggtcttcgt gtcgcagctg | 900 |
| cgccgcgagg gcgtcgaccc cgccgccata cggctcgcgc tgctcgccca ccactaccgg | 960 |
| gccgactggg agtggaccga ccaggtgctg cgggacgccg tcgaccgcct cggccgctgg | 1020 |
| cgtgccgcgg tctcccggcc cgacggcccg tccgccgagg ccctcgtcga ggagatccgc | 1080 |
| aaggcgctcg ccgacgacct ggacgccccg ccgccctgg ccgcggtcga ccgctgggcc | 1140 |
| gcctcgcagg aggagcacgg cggcaccgac atcggcgcgc cgggcgtggt gacacgagcg | 1200 |
| gtggacgcgc tgttgggcgt ggccctgtga | 1230 |

<210> SEQ ID NO 6
<211> LENGTH: 1530
<212> TYPE: DNA
<213> ORGANISM: Streptomyces lincolnens

<400> SEQUENCE: 6

| | |
|---|---|
| atgtcgtcct ccgttcgact ctccacactc ctcgcctcgg ccgccgaggc gaggcccgag | 60 |
| gccccgccg tcctggggga gacccggctc ccggtcacct atggggagct ggccgcgcgg | 120 |
| gcgggcggca tccaggccgc cctggcaggc ctggggggtgc gcgccggtga ccgggtagcg | 180 |
| ctgctgtccg gcggaccga cgcggacgcc gtggccgcgg tgcacgcgat cctgccgcg | 240 |
| ggcgccgtgt acgtgccgct cgacgccgcg tcgccgcccg cgcggtgggc ttcggtgagc | 300 |
| cgggtctgcg cgcccaccgc cgtggtgggc gaacgcgcgc tgctcgaccg gttcgccgcc | 360 |
| gccgtaccgg ggcgcggcg gctcgccctg ccatcggacg gggacgagct gcccgcgggc | 420 |
| cgcctcgacc ccgtccggag cgacggcacc gatgtcgcgt acctgctcac cacctccggc | 480 |
| tccaccggcg ttcccaagtg cgtggcccac accggtgcgg cgccgtcgc cttcctggag | 540 |
| tggatggtcg gcgcgttccc ggtgggcggc gacgatgtgt cgcctgcca cgccccgctg | 600 |
| cacttcgacg tgtcggtggc ctcggtgctc ggctccgcgc tgggcggcgc ggccctggcc | 660 |
| ccggtgcccc gtgaactgtc cgggtttccc gtcgagctgg ccacctggat cgccgaacgc | 720 |
| gccgtcaccg tatggctctc cgtgccctat ccgctcgccc gctgtccgg actggaggag | 780 |
| cgggccgcgc gtgagcgcct cgccaccttg aggacggtg tgttcgcggg tgacgtcttt | 840 |
| ccgcaccagc ggctcgccgc actgatgcgc tgcgcgcccg gggcccggtt cctcaacatc | 900 |

```
tacggcccga ccgagaccaa cggctgtacg tacgaggtcg tggacgcccc gcccgccggc      960
cccgtgccca tcggccggcc cgtcgagtgc gccgagtgct gggtcgagga cgacgacggg     1020
cggccggtcg acgcggtggg gtcggtgggt gaactcgtcg tcgcggggcc cacggtggcc     1080
gccggatact ggggcgtcga ggggcacgga gccgagcggt tccgcacggg ggagacctgt     1140
ccgggcggcc gggcctacgc caccggggac caggtccgcg tcctgcccgg ggccggtac      1200 gccttcctcg gccgcatgga caacatgatc aagatgcgcg gcagcggtt cgagctggag      1260 gaggtggaga acgctgtacg gctcgctccc ggcgtcgagg actgctgcgt ggtgaaggtg     1320
gacgtccgcg acgatcactc ccgcctcctc gccgtcgtgg tcgggcccgg cgccggcgac     1380
ccgcgcaccc tgcgcgagca ctgcctgacc aggctgccgt cgtgggcggt gccgcaccgg     1440
ttcctcacgg ccgccgcgct gcccctgggc tccaccggca aggtggaccg ccgcgcgctc     1500
agggaggaac tcgtcacacg cggggagtga                                      1530

<210> SEQ ID NO 7
<211> LENGTH: 1068
<212> TYPE: DNA
<213> ORGANISM: Streptomyces lincolnens

<400> SEQUENCE: 7
atggcggtat cacccccagtc ggttcggttg ccggaacacg cgccgcactg cgagatcggc      60
tgcgcggcga acgtggcgaa gagggtcggt gtcgacttcc cgcggcacgt ggccgggtcc      120
cagtgggcgc tgcgcacctt cgtccgggag cccggcgaca tcccgcagcc catgctggac      180
cgcacgcatc tgacgttcgg cgcgcacggc gagggctggc ccaccgccct cgcggggatc      240
acggacggca ccgtgcacga ccgccgggtg gcgcgttcgg agctcccgga ggtgctgcgg      300
gacgacctcg cccggggcgg cagtctgctg ttcctggagg accgcggctg cccatggctg      360
cactccgccg gccccgggct gctgccgcac acggtgaccc cggacggtgt cgacgcggcc      420
ggggtctggc agctgatcga ggggcacagc tggtgggcgg gccggtaccc gatggcggag      480
gccgacctgc tggccgcggc ctaccccgga cccgaccccgc accatgtggc gggccgggtc      540
ctgagcctgc gtctggccct gacgcccgag cgtcgcgcgg ccctgacgc cctcgccctg      600 gaccggctgc gggacagcgt gcgcgcctac ctcacggggg gcgacggccg gctcgacacc      660
ccggcgggca cgctggtgtg gacggacggg caggcggcg tcgcggaact gctggaccgg      720
ctgcggggct gggagtacct gtgcgcgctc gccgccgacg acggggccgg cgtcgagcag      780
ggcatcgaca tcgccgtggg ccggtatctg ttcctgggcc tggcggacga gctggcctac      840
acgtcgtacg cccgcgcggg cgccggcgc ctgacccgac gcctcggcgc tctcgcggac      900 atcgcgacg aacacctccc cgacgtggtg tggcagcggg cgtggcgcag cgcccagcgg      960
ttctaccggt cgctgcgcgc ggagcacttc gacgccctgt tgcacgacat cgacgcggcg     1020
ggggtggccg acgccgcttg tgcgcgccgg ctcgcggagg tcctgtag                  1068

<210> SEQ ID NO 8
<211> LENGTH: 858
<212> TYPE: DNA
<213> ORGANISM: Streptomyces lincolnens

<400> SEQUENCE: 8
gtgagcactc tggacgaggt cctcgccctg ctccgcacca tcgcgccgag cggcgacgag       60
accgaactca ccgccgacac cctcctgttc agctccggcc tgctcgacag tctcgccctg      120
```

| | |
|---|---|
| gaggagctgc acgtcgccat cgaggagcgc tgggcgccca tcccacccat ggaactggcg | 180 |
| cgggcgaact tcgacacccc ggccgccatc gccgcgacgg tggcccgtat cacccatgag | 240 |
| gagacccctg tgagtgttgt gaggaacctc ctgtccgact cgggccggct gaccgccgac | 300 |
| ctcgcaccgg acgctatcga gcgcggtgcg cagctgctct tcgacacctg gcacgccggc | 360 |
| ggcaccaccc tgtcctgcgg caacggcggc tcggcctcga ccgcctccca cttcgccgcc | 420 |
| gacctcgcca agctcaccat cgtgcccgga cagcgccgca tgcggacgct gtgcctgaac | 480 |
| gacaacgcct ccgcgttctc ggcgtggacc aacgacgagg gcttccccgt cgtctaccgg | 540 |
| gagcaggccg agccctggct ggagcccacc gccactctgg tcgcgttctc cgtgcacggc | 600 |
| ggctcccgcg ggggcgaagt gtcggcgaac ctgcccgccg tcgcccgcct cgccaaggaa | 660 |
| cgcggcgccg ccgtggtcgc ggtcaccggc ttcgacggcg cgccctcgg cgacctcgcg | 720 |
| gacgtccaca tcaacatccc gcacgccacc gagcccgtgg cgacccgct gatcgagtcg | 780 |
| ctgcacgtcc tcgtccacca cgccctgtgc gtcggcgcac gcgccctgat cctggagaag | 840 |
| gcgggggagc cggcatga | 858 |

<210> SEQ ID NO 9
<211> LENGTH: 1284
<212> TYPE: DNA
<213> ORGANISM: Streptomyces lincolnens

<400> SEQUENCE: 9

| | |
|---|---|
| atgaccgcca cggcgagcgg cgcgcagacc gccgcaccgg aacggctcac cgacgacggc | 60 |
| tggctgatcc ggcgcacatc cgtcgacacc gtccgcccct cgacgaccc gagcgcccag | 120 |
| tggatgctgg accgcgccca ggcccgtctg ccgctgtacc tgctgcacgt cgccgaccac | 180 |
| gcggaggcca cgccgcccgg actgcgcgag ccctgcacg cccaggacgc ggcccctgc | 240 |
| gacggcctgc tgttctccca gtacggcctg ccggagctgc gccggcggct cgacgcctgg | 300 |
| ctcgccgccg acgaggagtg ggacaccgcg cggagccgc tcgtcagcgt cgcgtggtcg | 360 |
| ggcaccggcg cggccatctt cgacctgctg cgcatgctca aggacggccg cccgggcccc | 420 |
| agcgccgtgc tgctgccgcg ccccgggtgg ggatatgaca tgtcggtgcg cgacaccgga | 480 |
| cacgtaccgg tgagttacga ggtgccccc gagtccccgc acggcccgga ccccgcgcac | 540 |
| ctggaggagg cgtggcagcg gtgccgcagc gagggcctcg acgtcgcctg catcctcatc | 600 |
| aacccgcagc acaacccgtg gggcggcaac tggacccccg agttcctcgc cgccgtcgcc | 660 |
| gccctcgccg aacgtgagcg agtgcccgtc ctggtggaca acgccttcta cgggctgacc | 720 |
| gccgaggacg tgcgcccccac cagcgcggtc cggctcctcg gccatctcgt cggccaggaa | 780 |
| ctcctggtgt cggtgcgcag cctgagcaag cagttcgcgt gcagcggctg ggccctggga | 840 |
| gccgtcgcgg gcagcccggg tctggtctcg gcgtactccg gccgctggcg ctgtctgcgg | 900 |
| gagccgaccg cgggcttccg cgcccaggcg gcgatggcgg cctggctcgg gggcgccgaa | 960 |
| cccgagcgct tcacccggcg ccgccgatcc gaggccaccc ggcacgccag gctcctgcgc | 1020 |
| accacactgc gcgcggcggg gctgcccgac gacgccgtcc tgcaccacgg cggcgccccc | 1080 |
| ttcaccctgc tgcggccccc gggcggcagc acgtcgagg aggtgcgcga gcagaccgtc | 1140 |
| gtgcggcacg gcgtcctgct cggcctggag cgggacgcgc gcgaacggcc gtggttcaag | 1200 |
| gtctggctgg gccgggacag cagcgtcttc gaacccgcgg cgcgggccct cggcgacgcc | 1260 |
| gcggccgagt ggcggtaccg gtga | 1284 |

<210> SEQ ID NO 10
<211> LENGTH: 31
<212> TYPE: DNA
<213> ORGANISM: Artificial sequence
<220> FEATURE:
<223> OTHER INFORMATION: Polynucleotide

<400> SEQUENCE: 10
tatgaattcc accttcacca cgcagcagtc c                                31

<210> SEQ ID NO 11
<211> LENGTH: 31
<212> TYPE: DNA
<213> ORGANISM: Artificial sequence
<220> FEATURE:
<223> OTHER INFORMATION: Polynucleotide

<400> SEQUENCE: 11
tattctagac cttcccgtac gaggagtaca c                                31

<210> SEQ ID NO 12
<211> LENGTH: 31
<212> TYPE: DNA
<213> ORGANISM: Artificial sequence
<220> FEATURE:
<223> OTHER INFORMATION: Polynucleotide

<400> SEQUENCE: 12
tattctagac gaaccgttcg ggggtgaagt c                                31

<210> SEQ ID NO 13
<211> LENGTH: 31
<212> TYPE: DNA
<213> ORGANISM: Artificial sequence
<220> FEATURE:
<223> OTHER INFORMATION: Polynucleotide

<400> SEQUENCE: 13
tataagcttc ccgttgcaca cgacgtttca c                                31

<210> SEQ ID NO 14
<211> LENGTH: 30
<212> TYPE: DNA
<213> ORGANISM: Artificial sequence
<220> FEATURE:
<223> OTHER INFORMATION: Polynucleotide

<400> SEQUENCE: 14
tatgaattcc tgttcacctc ctacggcgac                                  30

<210> SEQ ID NO 15
<211> LENGTH: 30
<212> TYPE: DNA
<213> ORGANISM: Artificial sequence
<220> FEATURE:
<223> OTHER INFORMATION: Polynucleotide

<400> SEQUENCE: 15
tattctagaa tccgcgacaa ggccctgatc                                  30

<210> SEQ ID NO 16
<211> LENGTH: 30
<212> TYPE: DNA
<213> ORGANISM: Artificial sequence
<220> FEATURE:
<223> OTHER INFORMATION: Polynucleotide

<400> SEQUENCE: 16
tattctagag cggatcttct tcaccagctc                                30

<210> SEQ ID NO 17
<211> LENGTH: 30
<212> TYPE: DNA
<213> ORGANISM: Artificial sequence
<220> FEATURE:
<223> OTHER INFORMATION: Polynucleotide

<400> SEQUENCE: 17
tataagcttc gccacatcgc cgaatggaac                                30

<210> SEQ ID NO 18
<211> LENGTH: 31
<212> TYPE: DNA
<213> ORGANISM: Artificial sequence
<220> FEATURE:
<223> OTHER INFORMATION: Polynucleotide

<400> SEQUENCE: 18
tatgaattcg acgacgctga cgtagtgcag g                              31

<210> SEQ ID NO 19
<211> LENGTH: 31
<212> TYPE: DNA
<213> ORGANISM: Artificial sequence
<220> FEATURE:
<223> OTHER INFORMATION: Polynucleotide

<400> SEQUENCE: 19
tattctagac tgacccgtga gcagttcgtg g                              31

<210> SEQ ID NO 20
<211> LENGTH: 31
<212> TYPE: DNA
<213> ORGANISM: Artificial sequence
<220> FEATURE:
<223> OTHER INFORMATION: Polynucleotide

<400> SEQUENCE: 20
tattctagag atgtcgtcgt gcacgcatgc c                              31

<210> SEQ ID NO 21
<211> LENGTH: 31
<212> TYPE: DNA
<213> ORGANISM: Artificial sequence
<220> FEATURE:
<223> OTHER INFORMATION: Polynucleotide

<400> SEQUENCE: 21
tataagcttg tcaccgcggt tgagctcgat c                              31

<210> SEQ ID NO 22
<211> LENGTH: 33
<212> TYPE: DNA
<213> ORGANISM: Artificial sequence
<220> FEATURE:
<223> OTHER INFORMATION: Polynucleotide

<400> SEQUENCE: 22
tatgaattcc ggttcgatct ccacaccgac cac                            33

<210> SEQ ID NO 23
<211> LENGTH: 33

<212> TYPE: DNA
<213> ORGANISM: Artificial sequence
<220> FEATURE:
<223> OTHER INFORMATION: Polynucleotide

<400> SEQUENCE: 23
tattctagac ttggccatgg tgtgcatggc gtg                                    33

<210> SEQ ID NO 24
<211> LENGTH: 33
<212> TYPE: DNA
<213> ORGANISM: Artificial sequence
<220> FEATURE:
<223> OTHER INFORMATION: Polynucleotide

<400> SEQUENCE: 24
tattctagac agaccggttt cctcgtacga ggg                                    33

<210> SEQ ID NO 25
<211> LENGTH: 33
<212> TYPE: DNA
<213> ORGANISM: Artificial sequence
<220> FEATURE:
<223> OTHER INFORMATION: Polynucleotide

<400> SEQUENCE: 25
tataagcttc atggtcaccc ggcaggaagt cac                                    33

<210> SEQ ID NO 26
<211> LENGTH: 30
<212> TYPE: DNA
<213> ORGANISM: Artificial sequence
<220> FEATURE:
<223> OTHER INFORMATION: Polynucleotide

<400> SEQUENCE: 26
tatgaattcg gatgtaccgt ttcctggacc                                        30

<210> SEQ ID NO 27
<211> LENGTH: 30
<212> TYPE: DNA
<213> ORGANISM: Artificial sequence
<220> FEATURE:
<223> OTHER INFORMATION: Polynucleotide

<400> SEQUENCE: 27
tattctagag gaggtggaga acgctgtacg                                        30

<210> SEQ ID NO 28
<211> LENGTH: 30
<212> TYPE: DNA
<213> ORGANISM: Artificial sequence
<220> FEATURE:
<223> OTHER INFORMATION: Polynucleotide

<400> SEQUENCE: 28
tattctagac cgaccatcca ctccaggaag                                        30

<210> SEQ ID NO 29
<211> LENGTH: 31
<212> TYPE: DNA
<213> ORGANISM: Artificial sequence
<220> FEATURE:
<223> OTHER INFORMATION: Polynucleotide

<400> SEQUENCE: 29

```
tataagcttc agtcacgtga cccaagtacc g                                31

<210> SEQ ID NO 30
<211> LENGTH: 31
<212> TYPE: DNA
<213> ORGANISM: Artificial sequence
<220> FEATURE:
<223> OTHER INFORMATION: Polynucleotide

<400> SEQUENCE: 30
tatgaattcc ctgatgctcc tgtacaccag c                                31

<210> SEQ ID NO 31
<211> LENGTH: 31
<212> TYPE: DNA
<213> ORGANISM: Artificial sequence
<220> FEATURE:
<223> OTHER INFORMATION: Polynucleotide

<400> SEQUENCE: 31
tattctagag tcctccagga acagcagact g                                31

<210> SEQ ID NO 32
<211> LENGTH: 31
<212> TYPE: DNA
<213> ORGANISM: Artificial sequence
<220> FEATURE:
<223> OTHER INFORMATION: Polynucleotide

<400> SEQUENCE: 32
tattctagac ggtatctgtt cctgggcctg g                                31

<210> SEQ ID NO 33
<211> LENGTH: 31
<212> TYPE: DNA
<213> ORGANISM: Artificial sequence
<220> FEATURE:
<223> OTHER INFORMATION: Polynucleotide

<400> SEQUENCE: 33
tataagcttg aacggtacgt gcaactcctc g                                31
```